US010195389B2

(12) United States Patent
Virr et al.

(10) Patent No.: US 10,195,389 B2
(45) Date of Patent: Feb. 5, 2019

(54) HUMIDIFIER WITH A WATER TUB WITHIN A PRESSURIZED CHAMBER

(71) Applicant: ResMed Limited, Bella Vista, New South Wales (AU)

(72) Inventors: Alexander Virr, Gosford (AU); Andrew Roderick Bath, Sydney (AU); Nathan John Row, Sydney (AU); Dan Kao, Sydney (AU); Phoebe Katherine Hill, Sydney (AU); Nicholas Andrew Earl, Essex (GB); Hargopal Verma, Sydney (AU); Junning Chen, Sydney (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 15/856,420

(22) Filed: Dec. 28, 2017

(65) Prior Publication Data

US 2018/0117273 A1  May 3, 2018

Related U.S. Application Data

(63) Continuation of application No. 15/194,634, filed on Jun. 28, 2016, which is a continuation of application
(Continued)

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0066* (2013.01); *A61M 16/0816* (2013.01);
(Continued)

(58) Field of Classification Search
CPC ............ A61M 16/1075; A61M 16/109; A61M 16/1095; A61M 16/16; F24F 6/02; F24F 6/05

See application file for complete search history.

(56) References Cited

U.S. PATENT DOCUMENTS 3,417,614 A  12/1968  Ryder
3,543,581 A  12/1970  Ryder
(Continued)

FOREIGN PATENT DOCUMENTS

CN  1809397 A  7/2006
CN  101296721 A  10/2008
(Continued)

OTHER PUBLICATIONS

Notice of Reasons for Rejection dated Feb. 15, 2016 issued in Japanese Application No. 2014-178855 with English translation (19 pages).
(Continued)

*Primary Examiner* — Kathryn E Ditmer
(74) *Attorney, Agent, or Firm* — Nixon & Vanderhye P.C.

(57) ABSTRACT

A tub is configured to contain a supply of water and is configured to be inserted into a chamber of a humidifier. The tub includes a tub base configured to contain the supply of water. The tub also includes a tub lid and a flow plate provided between the tub base and the tub lid. The flow plate includes a water level indicator configured to indicate a level of the supply of water in the tub base. In addition, the water level indicator includes a generally rectangular portion and a generally triangular portion.

30 Claims, 50 Drawing Sheets

Related U.S. Application Data

No. 14/157,639, filed on Jan. 17, 2014, now Pat. No. 9,402,970, which is a continuation of application No. 12/737,926, filed as application No. PCT/AU2009/001232 on Sep. 17, 2009, now Pat. No. 8,631,789.

(60) Provisional application No. 61/226,134, filed on Jul. 16, 2009, provisional application No. 61/097,765, filed on Sep. 17, 2008.

(51) Int. Cl.
*A61M 16/08* (2006.01)
*A61M 16/00* (2006.01)

(52) U.S. Cl.
CPC ...... *A61M 16/0875* (2013.01); *A61M 16/109* (2014.02); *A61M 16/1075* (2013.01); *A61M 16/1095* (2014.02); *A61M 2205/3368* (2013.01); *A61M 2205/3379* (2013.01); *A61M 2205/3382* (2013.01); *A61M 2205/3389* (2013.01); *A61M 2205/584* (2013.01); *A61M 2205/587* (2013.01)

(56) References Cited

U.S. PATENT DOCUMENTS

| | | | |
|---|---|---|---|
| 4,021,943 A | 5/1977 | McMullen | |
| 4,028,444 A * | 6/1977 | Brown | A61M 16/16 128/200.13 |
| 4,051,205 A | 9/1977 | Grant | |
| 4,098,853 A | 7/1978 | Brown et al. | |
| 4,201,737 A * | 5/1980 | Carden | A61M 16/16 128/200.21 |
| 4,714,078 A | 12/1987 | Paluch | |
| 4,819,625 A * | 4/1989 | Howe | A61M 16/16 128/200.14 |
| 4,941,469 A | 7/1990 | Adahan | |
| 5,529,060 A | 6/1996 | Salmon et al. | |
| 5,558,084 A | 9/1996 | Daniell et al. | |
| 5,588,423 A | 12/1996 | Smith | |
| 5,673,687 A | 10/1997 | Dobson et al. | |
| D419,658 S | 1/2000 | Matchett et al. | |
| 6,049,924 A | 4/2000 | Prows et al. | |
| 6,050,260 A | 4/2000 | Daniell et al. | |
| 6,095,505 A | 8/2000 | Miller | |
| D439,406 S | 3/2001 | Zimmerman | |
| 6,398,197 B1 | 6/2002 | Dickinson et al. | |
| 6,435,180 B1 * | 8/2002 | Hewson | A61M 16/16 128/203.12 |
| 6,669,626 B1 | 12/2003 | McDonough | |
| 6,935,337 B2 | 8/2005 | Virr et al. | |
| 7,111,624 B2 | 9/2006 | Thudor et al. | |
| 7,335,157 B2 | 2/2008 | Czupich et | |
| 7,677,246 B2 | 3/2010 | Kepler et al. | |
| 8,631,789 B2 | 1/2014 | Virr et al. | |
| 9,402,970 B2 | 8/2016 | Virr et al. | |
| 2001/0050080 A1 | 12/2001 | Seakins et al. | |
| 2002/0020930 A1 | 2/2002 | Austin et al. | |
| 2005/0247314 A1 | 11/2005 | Virr et al. | |
| 2006/0055069 A1 | 3/2006 | Dimatteo et al. | |
| 2006/0191531 A1 | 8/2006 | Mayer et al. | |
| 2006/0237005 A1 * | 10/2006 | Virr | A61M 16/16 128/200.24 |
| 2007/0035044 A1 * | 2/2007 | Chiu | F24F 6/02 261/81 |
| 2007/0169776 A1 * | 7/2007 | Kepler | A61M 16/0051 128/200.23 |
| 2007/0210462 A1 | 9/2007 | Felty et al. | |
| 2008/0022768 A1 | 1/2008 | Bell et al. | |
| 2008/0072900 A1 | 3/2008 | Kenyon et al. | |
| 2008/0105257 A1 | 5/2008 | Klasek et al. | |
| 2008/0245365 A1 | 10/2008 | Genger | |
| 2008/0302361 A1 * | 12/2008 | Snow | A61M 16/1075 128/202.27 |
| 2009/0223514 A1 | 9/2009 | Smith et al. | |
| 2011/0155132 A1 | 6/2011 | Virr et al. | |
| 2014/0130802 A1 | 5/2014 | Virr et al. | |
| 2016/0303343 A1 | 10/2016 | Virr et al. | |

FOREIGN PATENT DOCUMENTS

| | | | | |
|---|---|---|---|---|
| DE | 25 12 607 A1 | 10/1975 | | |
| DE | 100 16 005 A1 | 12/2001 | | |
| EP | 0 845 277 A2 | 6/1998 | | |
| EP | 0 885 623 A2 | 12/1998 | | |
| GB | 2 293 325 | 3/1996 | | |
| GB | 299 09 611 | 9/1999 | | |
| JP | 54-36426 | 8/1952 | | |
| JP | 56-134526 | 3/1955 | | |
| JP | 38-2902 Y | 2/1963 | | |
| JP | 42-4385 Y | 3/1967 | | |
| JP | 57-101952 | 6/1982 | | |
| JP | 5-71790 A | 3/1993 | | |
| JP | 5-228214 | 9/1993 | | |
| JP | 9-10088 | 1/1997 | | |
| JP | 9-60932 A | 3/1997 | | |
| JP | 10-179746 A | 7/1998 | | |
| JP | 11-57009 A | 3/1999 | | |
| JP | 2004-524088 | 8/2004 | | |
| JP | 2004-359274 | 12/2004 | | |
| JP | 2008-518640 | 6/2008 | | |
| JP | 2008-518640 A | 6/2008 | | |
| WO | WO 01/97894 A1 | 12/2001 | | |
| WO | 02/066107 | 8/2002 | | |
| WO | WO 2004/112873 A1 | 12/2004 | | |
| WO | WO 2004112873 A1 * | 12/2004 | ........ A61M 16/0051 | |
| WO | 2006/012877 A1 | 2/2006 | | |
| WO | WO 2007/038152 A2 | 4/2007 | | |
| WO | WO 2007/045017 A2 | 4/2007 | | |
| WO | 2008/056993 A2 | 5/2008 | | |
| WO | WO 2008056993 A2 * | 5/2008 | ........ A61M 16/0066 | |
| WO | WO 2009/156921 A1 | 12/2009 | | |

OTHER PUBLICATIONS

Statutory Declaration of Ahmed Al-Jumaily filed Mar. 1, 2016 in New Zealand Application No. 590924 (47 pages).
Statutory Declaration of Ian Douglas Makinson filed Mar. 1, 2016 in New Zealand Application No. 590924 (10 pages).
Statutory Declaration of Yi-Cheng Sun filed Mar. 1, 2016 in New Zealand Application No. 590924 (2 pages).
Proceeding Correspondence dated Mar. 14, 2016 issued in New Zealand Application No. 590924 confirming filing of Statutory Declarations on Mar. 1, 2016.
Examination Report dated Nov. 6, 2015 issued in European Application No. 09813893.6 (6 pages).
Notice of Reasons for Rejection dated Aug. 31, 2015 issued in Japanese Application No. 2014-178855 with English translation (22 pages).
Notification of the Fifth Office Action dated Aug. 6, 2015 in Chinese Application No. 200980136567.9 with English translation (8 pages).
Amended Notice of Opposition to Grant of Patent and Statement of Case filed May 20, 2014 in New Zealand Application No. 590924 (10 pages).
Notification of the Second Office Action dated Jan. 24, 2014 in Chinese Application No. 200980136567.9, with English translation (17 pages).
Extended European Search Report dated Feb. 5, 2014 in European Application No. 09813893.6 (7 pages).
First Examination Report dated Feb. 24, 2014 in New Zealand Application No. 620739 (2 pages).
Notification of the Third Office Action dated Jul. 18, 2014 in Chinese Application No. 200980136567.9, with English translation (17 pages).
Statutory Declaration of Yi-Cheng Sun filed on Dec. 24, 2014 in New Zealand Application 590924.
Statutory Declaration of Stephen William McPhee filed on Dec. 24, 2014 in New Zealand Application 590924.

(56) References Cited

OTHER PUBLICATIONS

Statutory Declaration of Philip John Dickinson filed on Dec. 24, 2014 in New Zealand Application 590924.
Statutory Declaration of Kieran James Hatcher filed on Dec. 24, 2014 in New Zealand Application 590924.
Affirmation of Andrew Michael Baker filed on Dec. 24, 2014 in New Zealand Application 590924.
Proceeding Correspondence dated Jan. 6, 2015 in New Zealand Application No. 590924 (2 pages).
Statutory Declaration of Yi-Cheng Sun filed on Feb. 4, 2015 in New Zealand Application 590924.
First Examination Report dated Jun. 30, 2015 issued in Australian Application No. 2014203009 (3 pages).
First Examination Report dated Aug. 3, 2015 issued in New Zealand Application No. 710351 (2 pages).
Notice of Reasons for Rejection dated Jun. 23, 2014 issued in corresponding Japanese Application No. 2011-527153 (4 pages).
International Search Report for PCT/AU2009/001232, dated Dec. 24, 2009.
Examination Report dated Mar. 23, 2012 in New Zealand Appln. No. 590924 (3 pages).
Patent Examination Report No. 1 dated Jun. 21, 2013 in Australian Application No. 2009295268 (3 pages).
Notice of Reasons for Rejection dated Sep. 3, 2013 in Japanese Application No. 2011-527153, with English translation (6 pages).
Notice of Reasons for Rejection dated Oct. 17, 2016 issued in Japanese Application No. 2014-178855 with English translation (16 pages).
First Examination Report dated Jan. 19, 2017 issued in New Zealand Application No. 727472 (3 pages).
Virr et al., U.S. Appl. No. 15/194,634, filed Jun. 28, 2016, for "Humidifier with a Water Tub Within a Pressurized Chamber," (parent case).
Proceeding Correspondence dated Sep. 12, 2017 issued in New Zealand Application No. 710351 (2 pages).
Statement of Case dated Aug. 25, 2017, filed by Fisher & Paykel Healthcare Limited in New Zealand Application No. 710351 (10 pages).
Amended Notice of Opposition to Grant of Patent (Section 21), with no markups, dated Aug. 25, 2017, filed by Fisher & Paykel Healthcare Limited in New Zealand Application No. 710351 (2 pages).
Amended Notice of Opposition to Grant of Patent (Section 21), with markups, dated Aug. 25, 2017, filed by Fisher & Paykel Healthcare Limited in New Zealand Application No. 710351 (2 pages).
ResMed Sullivan® HumidAire™ User's Manual, 2001 (136 pages).
Notice of Reasons for Rejection dated Feb. 5, 2018 in Japanese Application No. 2017-027684, with English translation (10 pages).
Notice of Reasons for Rejection dated Feb. 9, 2018 in Japanese Application No. 2014-178855 (Appeal No. 2017-2304), with English translation (5 pages).
First Examination Report dated May 4, 2018 in New Zealand Application No. 741547 (2 pages).
Notification of the First Office Action dated Dec. 5, 2017 in Chinese Application No. 201610248130.6, with English translation (26 pages).
Brochure for "BREAS® Luftbefeuchter HA 50—Schafft die Perfekte Atmosphäre," with English Translation (BREAS® Humidifier HA 50—Create the Perfect Atmosphere) (4 pages), date not available.
Fisher & Paykel Healthcare, "HC200 Series Nasal CPAP Blower & Heated Humidifier User's Manual," May 1998, 17 pages.
First Examination Report dated Aug. 1, 2018 in New Zealand Application No. 744305 (1 page).
Extended European Search Report dated Aug. 3, 2018 in European Application No. 18152801.9 (11 pages).
Virr et al., Office Action dated Jun. 6, 2018 in U.S. Appl. No. 15/194,634 (17 pages).
IPONZ Communication dated May 28, 2018 re Extension of Time Granted in NZ Application No. 736958 (1 page) with Application Under Regulation 168 for Extension of Time (1 page) and Notice of Opposition to Grant of Patent (Section 121) (2 pages) filed by Fisher & Paykel Healthcare Limited on May 25, 2018.
Statement of Case Dated Jul. 26, 2018 and filed by Fisher & Paykel in New Zealand Application No. 736958 (25 pages).
Amended Notice of Opposition filed Jul. 26, 2018 by Fisher & Paykel in New Zealand Application No. 736958, clean and track changes versions (4 pages).
Amended Statement of Case (tracked and clean versions) filed by Dentons New Zealand Limited on behalf of the Opponent Fisher & Paykel Healthcare Limited in New Zealand Application No. 736958 (52 pages).

\* cited by examiner

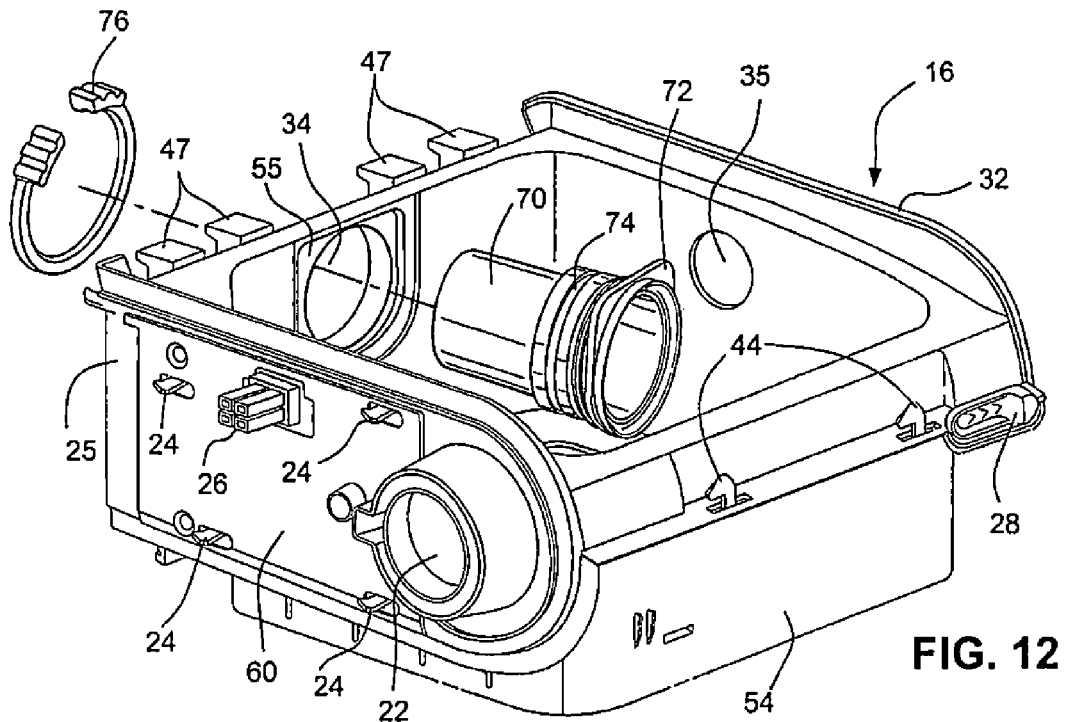
FIG. 12
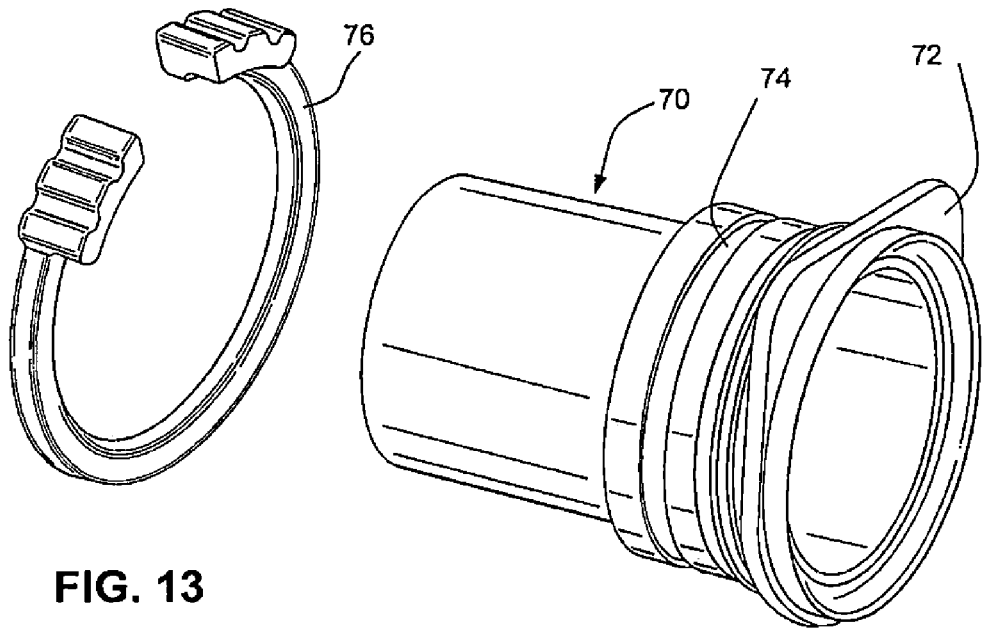
FIG. 13
FIG. 14

HUMIDIFIER WITH A WATER TUB WITHIN A PRESSURIZED CHAMBER

CROSS REFERENCE TO RELATED APPLICATIONS

This application is a continuation of U.S. application Ser. No. 15/194,634, filed Jun. 28, 2016, now pending, which is a continuation of U.S. application Ser. No. 14/157,639, filed Jan. 17, 2014, now U.S. Pat. No. 9,402,970, which is a continuation of U.S. application Ser. No. 12/737,926, filed Mar. 1, 2011, now U.S. Pat. No. 8,631,789, which is the U.S. National Phase of International Application No. PCT/AU2009/001232 filed on Sep. 17, 2009 and which claims priority to U.S. Applications 61/097,765, filed Sep. 17, 2008 and 61/226,134, filed Jul. 16, 2009, the entire contents of each being incorporated herein by reference.

The entire contents of U.S. application Ser. No. 12/397,850, filed Mar. 4, 2009, are incorporated herein by reference.

FIELD OF THE INVENTION

The present invention relates to systems and method to control the humidity of breathable gases used in all forms of respiratory apparatus ventilation systems including invasive and non-invasive ventilation, Continuous Positive Airway Pressure (CPAP), Bi-Level therapy and treatment for sleep disordered breathing (SDB) conditions such as Obstructive Sleep Apnea (OSA), and for various other respiratory disorders and diseases.

BACKGROUND OF THE INVENTION

Respiratory apparatuses commonly have the ability to alter the humidity of the breathable gas in order to reduce drying of the patient's airway and consequent patient discomfort and associated complications. The use of a humidifier placed between the flow generator and the patient mask produces humidified gas that minimizes drying of the nasal mucosa and increases patient airway comfort. In addition in cooler climates, warm air applied generally to the face area in and about the mask is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that the patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a patient conduit that delivers the humidified gas to the patient's mask.

Typically, the heating element is incorporated in a heater plate which sits under, and is in thermal contact with, the water tub.

SUMMARY OF THE INVENTION

One aspect of the invention is a respiratory apparatus that comprises a humidifier for humidifying a flow of breathable gas to be delivered to a patient in which a tub of the humidifier is insulated to reduce the temperature of the water and the power consumed by the apparatus.

Another aspect of the invention is a humidifier for a respiratory apparatus that includes a chamber that is pressurizable to reduce the pressure on joints of the humidifier tub to reduce leaks.

A further aspect of the invention is a humidifier for a respiratory apparatus that includes a chamber that is pressurizable to reduce tolerances for insertion of a tub with respect to seals on an inlet and an outlet tube of the humidifier chamber.

A still further aspect of the invention is a humidifier for a respiratory apparatus that directs air over the surface of a supply of water contained in a tub to humidify a flow of breathable gas regardless of the water level.

Another aspect of the invention is a humidifier for a respiratory apparatus that includes seals that are not under the supply of water, thus reducing a risk of leakage.

A still further aspect of the invention is a humidifier for a respiratory apparatus that prevents water from spilling back into a flow generator, or blower, that generates a flow of breathable gas.

Yet another aspect of the invention is a humidifier for a respiratory apparatus that includes a tub that is disposable.

Another aspect of the invention is a humidifier for a respiratory apparatus that includes a tub that is cleanable and/or reusable.

Still another aspect of the invention is a humidifier for a respiratory apparatus that includes a tub that comprises a water level indicator, for example a water level indicator that indicates a maximum fill level. Yet another aspect of the invention relates to a water level indicator that may be removable from the tub. A still further aspect of the invention relates to a water level indicator in a tub that may be viewed through a window of the humidifier. An even further aspect of the invention relates to a water level indicator that appears to change color as the water level changes, for example appears to be a darker color or mixture of colors.

Another aspect of the invention is a humidifier for a respiratory apparatus that is connectable to a heated or non-heated tube for delivery of the humidified flow to a patient.

A further aspect of the invention relates to a tub that is removable from the humidifier and is configured to prevent any water flowing out of the tub from flowing back into the flow generator.

According to a sample embodiment, a humidifier for humidifying a flow of breathable gas to be delivered to a patient comprises a chamber configured to receive the flow of breathable gas; a tub configured to contain a supply of water, the tub being configured to be inserted into the chamber; a lid provided on the chamber and being movable between an open position and a closed position; and a seal provided on the lid, the seal being configured to seal the chamber such that the flow of breathable gas pressurizes the chamber.

According to yet another sample embodiment, a tub for insertion into a humidifier chamber comprises a tub base configured to contain a supply of water; a tub lid; a flow plate; and a seal connected to the flow plate, wherein the flow plate is positioned between the tub base and the tub lid via the engagement of the seal with side wall edges of the tub base and side wall edges of the tub lid.

According to a further sample embodiment, a respiratory apparatus for providing a humidified flow of breathable gas to a patient comprises a flow generator to generate a flow of breathable gas and a humidifier and/or a tub as described above.

According to another sample embodiment, a humidifier for humidifying a flow of breathable gas to be delivered to a patient comprises a chamber configured to receive the flow of breathable gas; a tub configured to contain a supply of water, the tub being configured to be inserted into the chamber; and a lid provided on the chamber and being movable between an open position and a closed position. The tub comprises a tub base configured to contain a supply of water; a tub lid; and a flow plate provided between the tub base and the tub lid, wherein the flow plate comprises a water level indicator configured to indicate a level of the supply of water in the tub base.

According to a still further sample embodiment, a tub is configured to contain a supply of water and to be inserted into a chamber of a humidifier. The tub comprises a tub base configured to contain a supply of water; a tub lid; and a flow plate provided between the tub base and the tub lid, wherein the flow plate comprises a water level indicator configured to indicate a level of the supply of water in the tub base. The water level indicator comprises a generally rectangular portion and a generally triangular portion. The generally triangular portion comprises an angled wall that extends at least partially below the flow plate and the angled wall comprises a drain hole and indicia.

BRIEF DESCRIPTION OF THE DRAWINGS

Embodiments of the invention will now be described with reference to the accompanying drawings, in which:

FIG. 12 schematically depicts the humidifier of FIG. 1 including an outlet tube;

FIG. 13 schematically depicts a sealing ring for the humidifier outlet tube of FIG. 12;

FIG. 14 schematically depicts the outlet tube of the humidifier of FIG. 12;

DETAILED DESCRIPTION OF ILLUSTRATED EMBODIMENTS

Respiratory Apparatus

Figure 1:
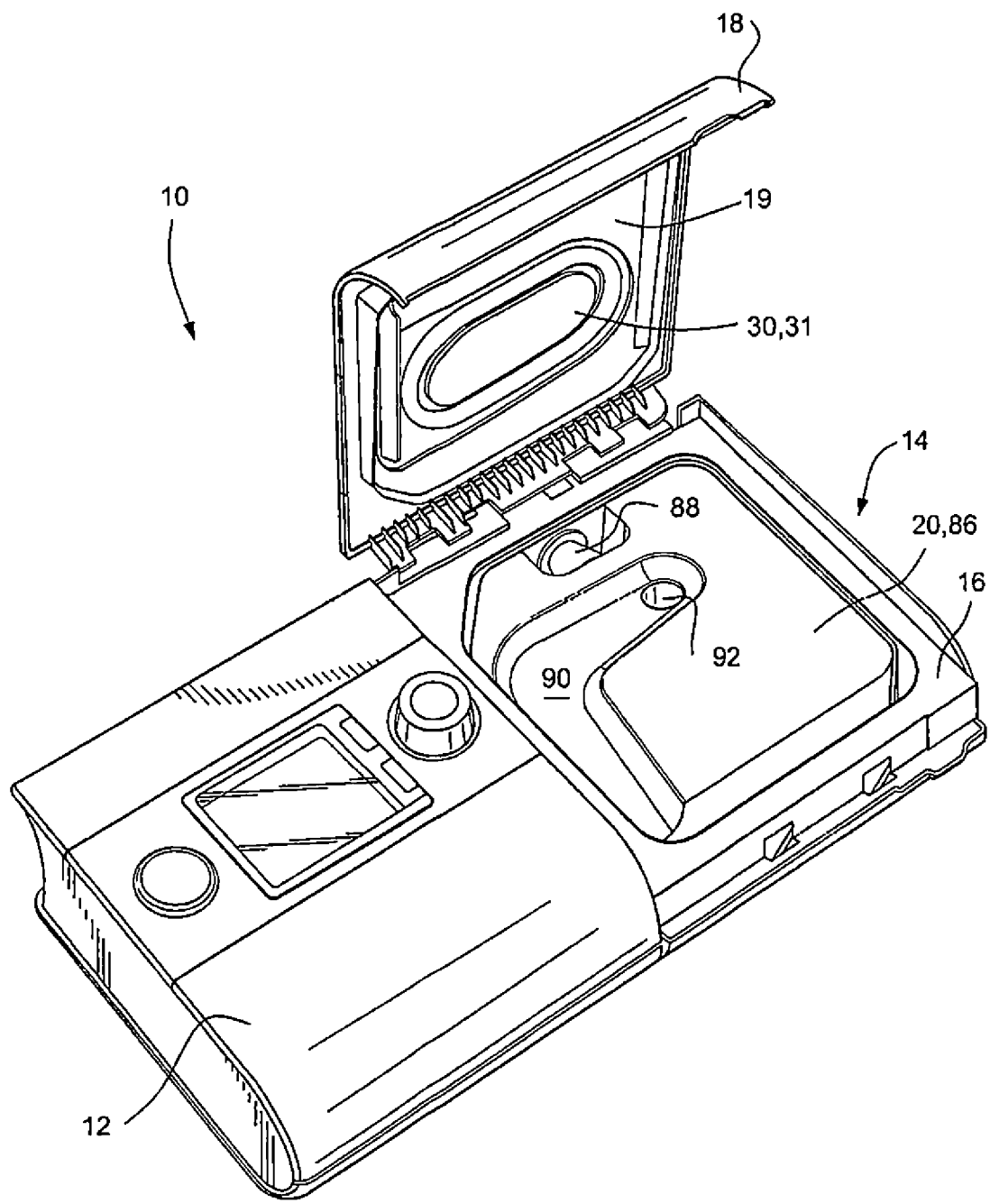
FIG. 1 schematically depicts of a respiratory apparatus including a flow generator and humidifier according to a sample embodiment of the invention.

Referring to FIG. 1, a respiratory apparatus 10 comprises a flow generator, or blower, 12 and a humidifier 14. The humidifier 14 comprises a humidifier chamber 16 and a lid 18 which is pivotable between an open and a closed position. A water chamber, or tub, 20 is provided in the humidifier chamber 16 and is covered by the lid 18 when the lid 18 is in the closed position. A seal 19 is provided to the lid 18, as shown in more detail in FIG. 15. The lid 18 includes a window 30 to allow visual inspection of the contents of the humidifier tub 20. The seal 19 includes an aperture 31 that corresponds to the position of the window 30 of the lid 18.

The tub 20 comprises a tub lid 86 that is configured to direct a flow of breathable gas generated by the flow generator 12 along a channel 90 and through an outlet 92 of the channel 90 into the tub 20, as described in more detail below. The tub 20 includes an outlet 88 for the humidified flow of breathable gas to a tube configured to deliver the humidified flow to a patient interface, e.g. a mask.

Humidifier

Figure 2:
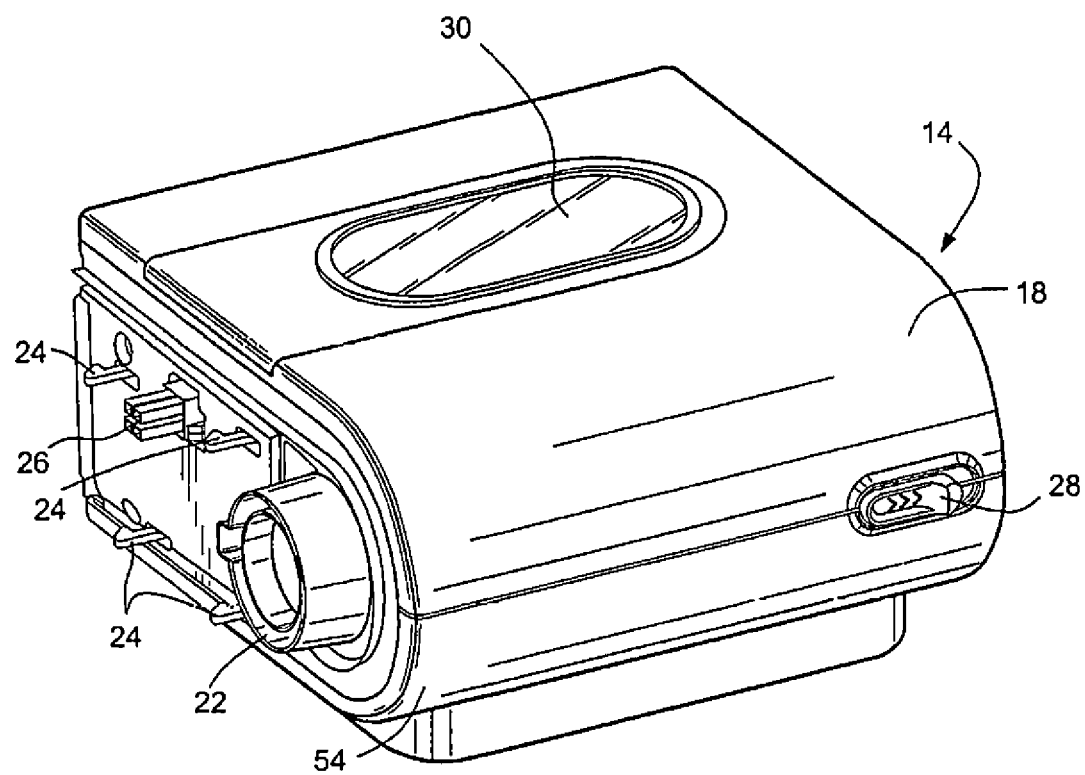
FIG. 2 schematically depicts the humidifier of FIG. 1 with the lid in the closed position.

As shown in FIG. 2, the humidifier 14 is connectable to the flow generator 12 by connectors, or latches, 24. The latches 24 may be, for example, spring biased latches that engage corresponding recesses (not shown) in the flow generator 12. An electrical connector 26 is provided to electrically connect the flow generator 12 to the humidifier 14. Electrical power may be provided from the flow generator 12 to the humidifier 14, although it should be appreciated that the humidifier may be provided with its own power source. Control signals may also be provided from the flow generator 12 to the humidifier 14 through the electrical connector 26.

Figure 4:
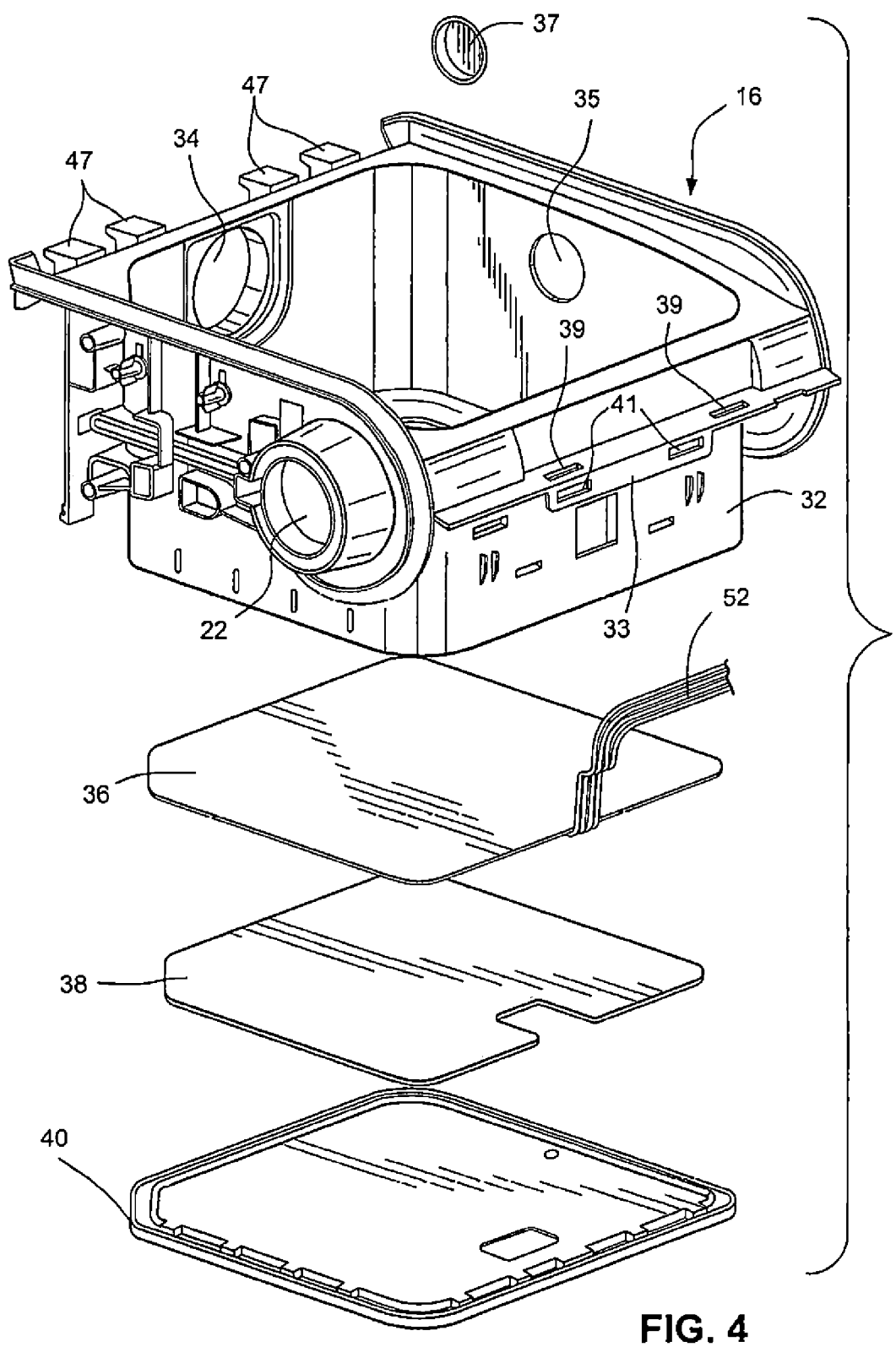
FIG. 4 schematically depicts a partial exploded assembly view of the humidifier of FIG. 1.

It should be appreciated that the humidifier 14 may include its own control system, for example, a microprocessor provided on a printed circuit board (PCB). The PCB may be located in the wall of the humidifier chamber 16 and may include a light, e.g. an LED, to illuminate the contents of the tub 20 to permit visual inspection of the water level. Referring to FIG. 4, an aperture 35 may be provided in the wall of the humidifier chamber 16 to allow the light on the PCB to illuminate the humidifier chamber 16. The aperture 35 is covered with a cover 37 to prevent access to the PCB and the light (e.g. LED) from the humidifier chamber 16. The cover 37 may be transparent or colored to provide a colored light, such as a green light to appear within the humidifier chamber 16. The light is provided to shine into the humidifier chamber 16 to allow the water level in the water tub 20 to be seen. Alternatively, multiple lights may be located on the PCB to provide different indications regarding the heating of the humidifier, for example an amber light may be provided to indicate that the humidifier is heating up to a required temperature and a blue light may be provided to identify when the humidifier is at the required temperature.

Figure 3:
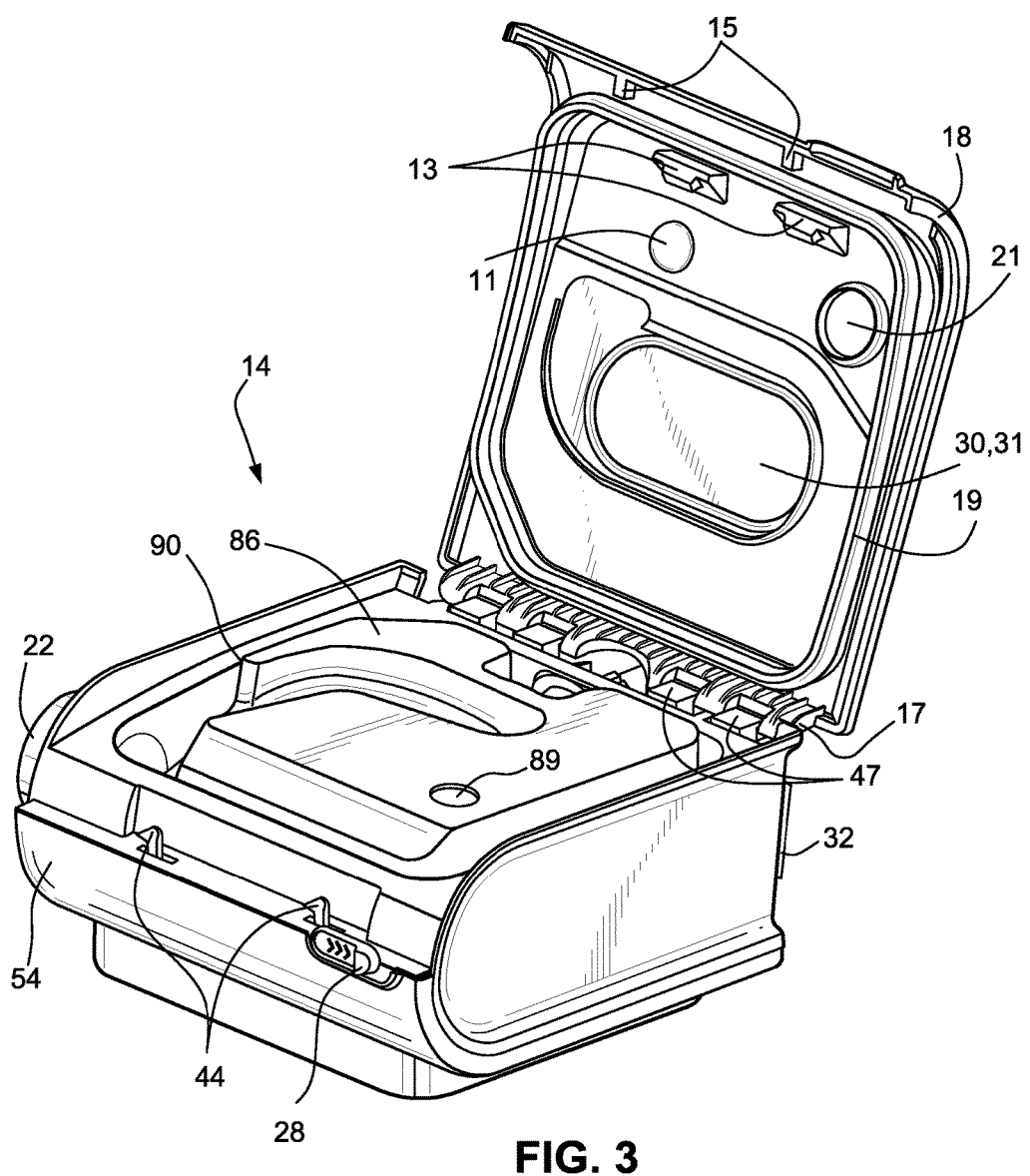
FIG. 3 schematically depicts the humidifier of FIG. 1 with the lid in the open position.

The humidifier 14 comprises the humidifier chamber 16 and the lid 18 which is pivotally connected to the humidifier chamber 16. As shown in FIGS. 3 and 4, the lid 18 comprises a hinge portion 17 that is hinged to hinge portions 47 provided on the humidifier chamber 16. Referring to FIG. 3, a humidifier bottom 54 is provided to the humidifier chamber 16, as shown in more detail in FIG. 8. An opening member 28 is provided for releasing the lid 18 to allow the lid to be pivoted to the open position as described in more detail below.

Referring again to FIGS. 3 and 4, the lid 18 comprises catches 15 that are configured to be engaged by the latches 44 to maintain the lid in the closed position. The seal 19 also comprises wedge-shaped protrusions 13 that are configured to engage the water tub 20, for example the tub lid 86, when the lid 18 is in the closed position to push the tub 20 in a direction (e.g. laterally) toward an outlet 34 of the humidifier chamber 16 to assist in forming a seal between the water tub outlet 88 and the humidifier chamber outlet 34. A domed portion 11 is also provided on the seal 19 to push the water tub 20 against a heating plate 36 when the lid 18 is in the closed position. A circular seal section, or sealing ring, 21 is also provided to the seal 19 to seal, when the lid 18 is in the closed position, a tub emptying aperture 89 provided in the tub lid 86.

Referring again to FIGS. 2 and 4, the humidifier chamber 16 also includes an air inlet 22 configured to receive the flow of breathable gas generated by the flow generator 12 when the humidifier 14 is connected to the flow generator 12 by the latches 24. The inlet 22 directs the flow into the channel 90 (see FIGS. 1, 3 and 21-24) in the tub lid 86 of the water tub 20. The flow is directed by the channel 90 to the outlet 92 into the water tub 20.

Figure 5:
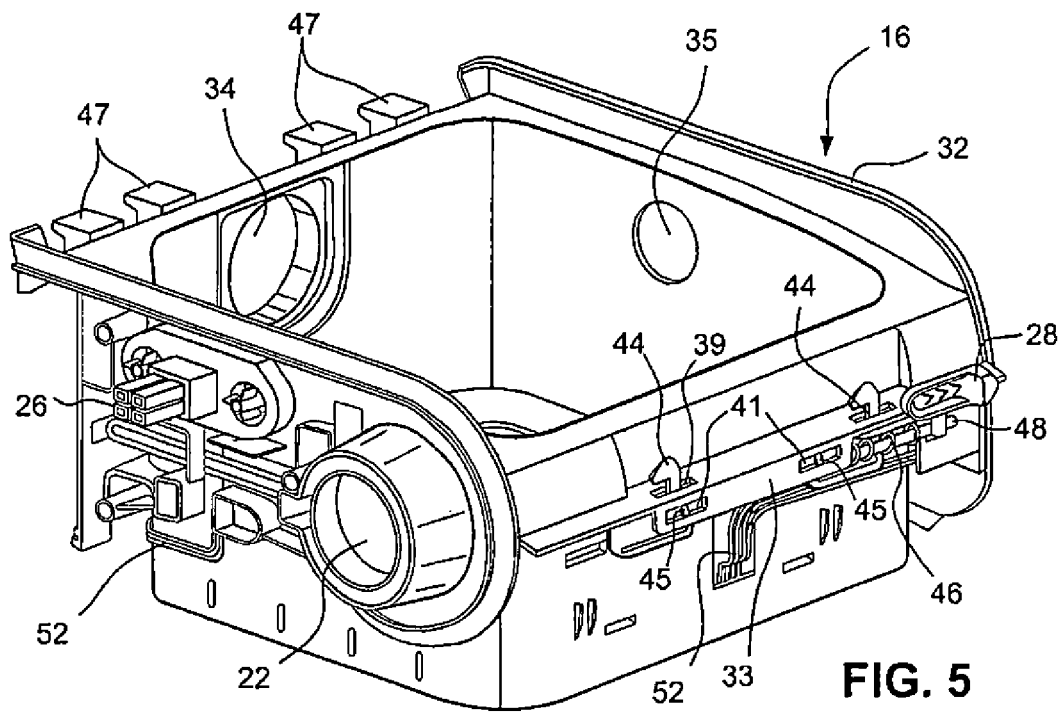
FIG. 5 schematically depicts a cradle of the humidifier of FIG. 4.

As shown in FIGS. 4 and 5, the humidifier chamber 16 comprises a humidifier cradle 32 that includes the air inlet 22. The humidifier cradle 32 also includes the humidifier chamber outlet 34 to allow the humidified flow to be delivered to a delivery hose, tube, or conduit that is configured to be connected to the humidifier to deliver the humidified flow to a patient. The outlet 34 is provided in a back side of the humidifier cradle 32. It should be appreciated that the outlet 34 may be provided on a side of the humidifier cradle 32. Such a modification would also entail modifying the water tub 20 to align the outlet 88 of the tub 20 with the outlet 34 of the humidifier cradle 32.

Referring to FIG. 4, the heating plate 36 is provided to heat the water supply contained in the humidifier chamber 16. A cradle bottom 40 is provided beneath the heating plate 36 and an insulation layer 38 is provided between the heating plate 36 and the cradle bottom 40. The heating plate 36 may be formed, for example, of a nickel chrome alloy or anodized aluminum that allows the heating plate 36 to be formed thinner than currently available heating plates and with a larger surface area. The heating plate 36 may also include a thermistor that is controlled by a control circuit, for example, provided on the PCB.

Figure 6:
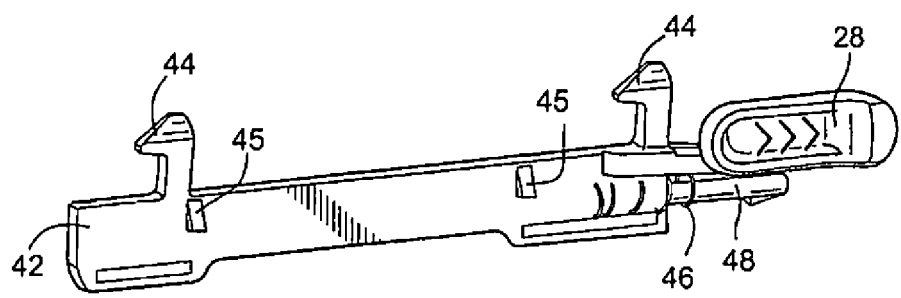
FIG. 6 schematically depicts a lid closure member of the humidifier.

Referring to FIGS. 4-6, the humidifier cradle 32 supports a lid closure member 42 that is movable between an open position and a closed position. The lid opening member 28 is provided at an end of the lid closure member 42 as shown in FIG. 6. The lid closure member 42 comprises latches 44 that are configured to engage catches 15 of the lid 18 and retain the lid 18 in the closed position. The lid closure member 42 comprises a rod, or post, 48 that supports a spring 46 that biases the lid closure member 42 into the closed position. To open the lid 18, the opening member 28 is pushed by the user against the bias of the spring 46, to the right in FIG. 5, to move the latches 44, and the lid closure member 42, to the open position. When the user releases the lid opening member 28, the bias of the spring 46 returns the lid closure member 42 and the latches 44 to the closed position.

The lid closure member 42 is supported by a front retaining wall 33 of the cradle 32. The lid closure member 42 includes tabs 45 that engage slots 41 formed in the front retaining wall 33. The front retaining wall 33 also comprises slots 39 through which the latches 44 protrude. The slots 39, 41 accommodate sliding movement of the lid closure member 42 and the latches 44 and the tabs 45, respectively, engaged with the slots 39, 41.

Figure 7:
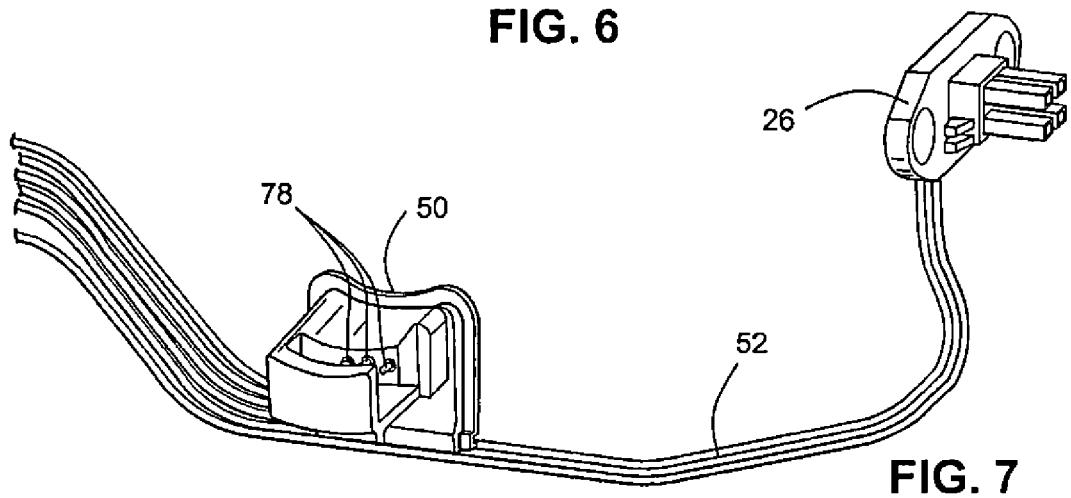
FIG. 7 schematically depicts an electrical connector and tube connector of the humidifier of FIG. 1.
Figure 15:
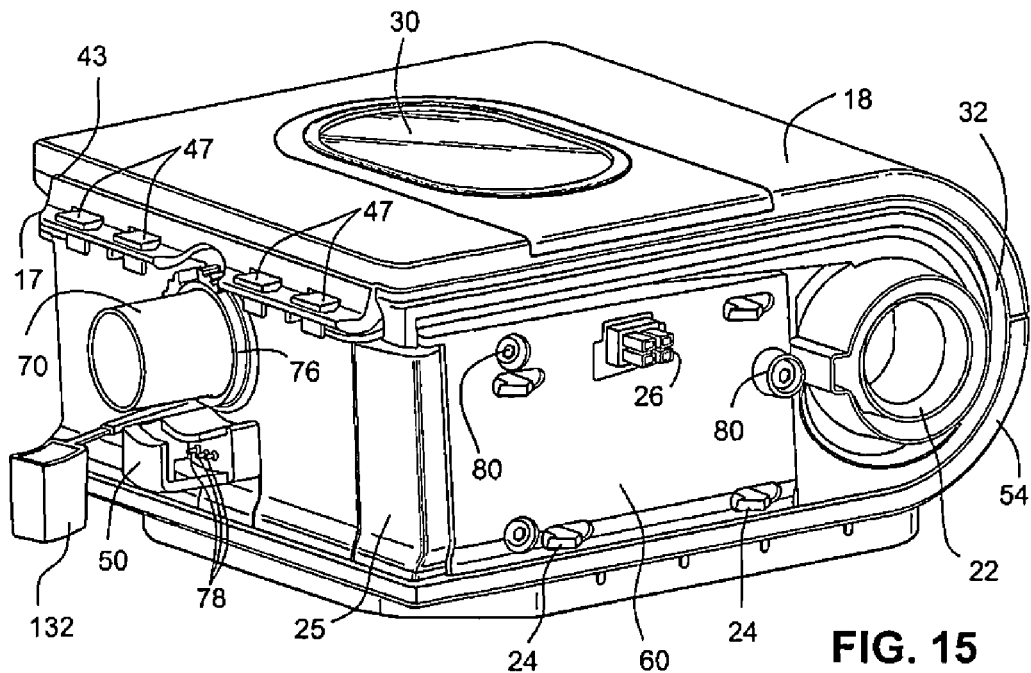
FIG. 15 schematically depicts the humidifier of FIG. 1 including the inner plate, the outlet tube, and the tube connector.

As shown in FIG. 7, the electrical connector 26 is connected to a plurality of wires 52, for example, three wires, that are connected to a tube connector 50 that is shown in FIG. 15 and described in more detail hereinafter. The tube connector 50 comprises a plurality of contacts 78 that correspond in number to a number of wires 52 and are each connected to a respective wire. Although three wires 52 and three contacts 78 are shown in the drawings, it should be appreciated that a different number of wires and contacts may be provided, for example, two wires and two contacts. The tube connector 50 allows for the connection of a heated tube, for example, such as disclosed in U.S. patent application Ser. No. 11/936,822, filed Nov. 8, 2007, the entire contents of which are incorporated herein by reference.

Figure 8:
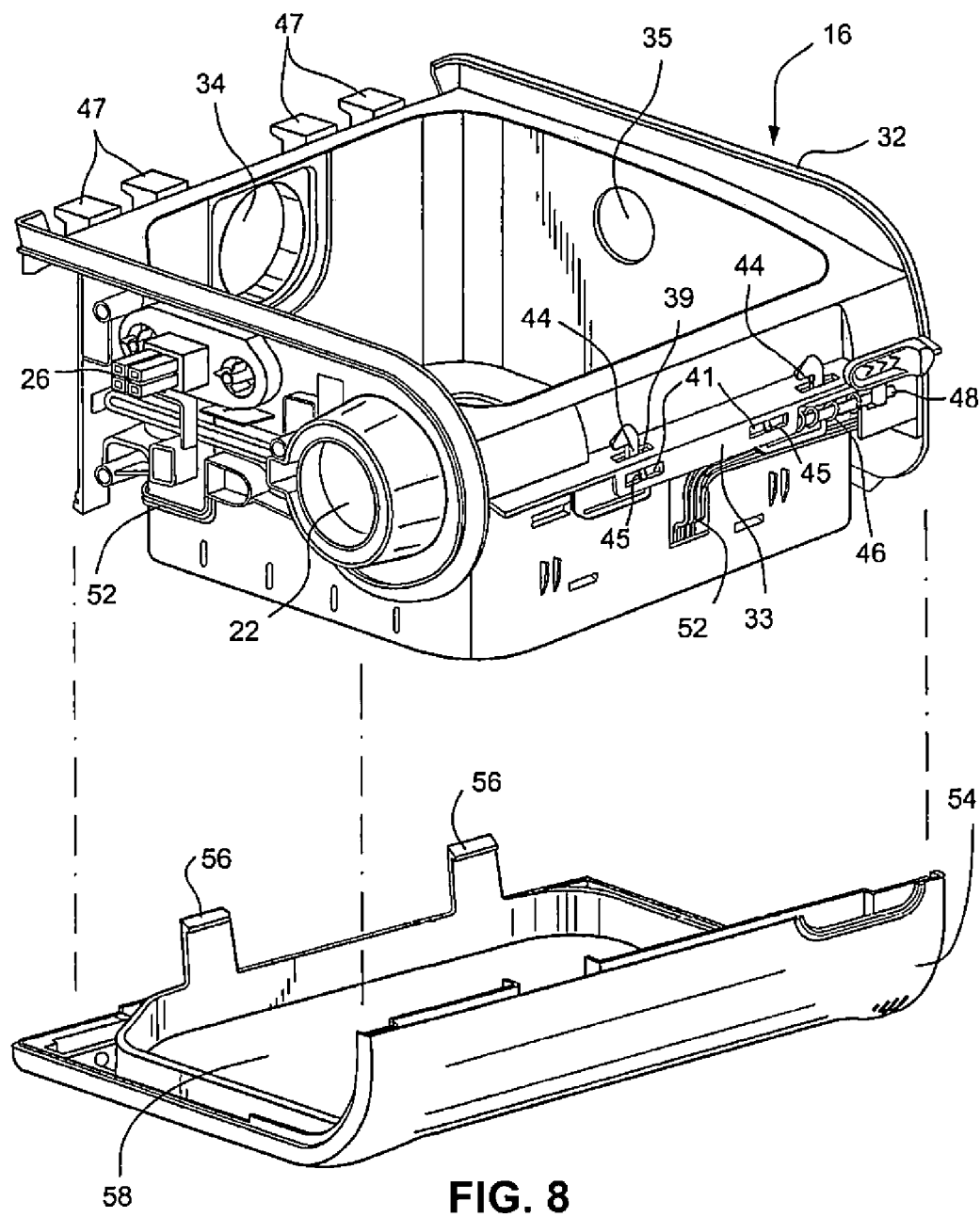
FIG. 8 schematically depicts the cradle and humidifier bottom of the humidifier of FIG. 1.
Figure 9:
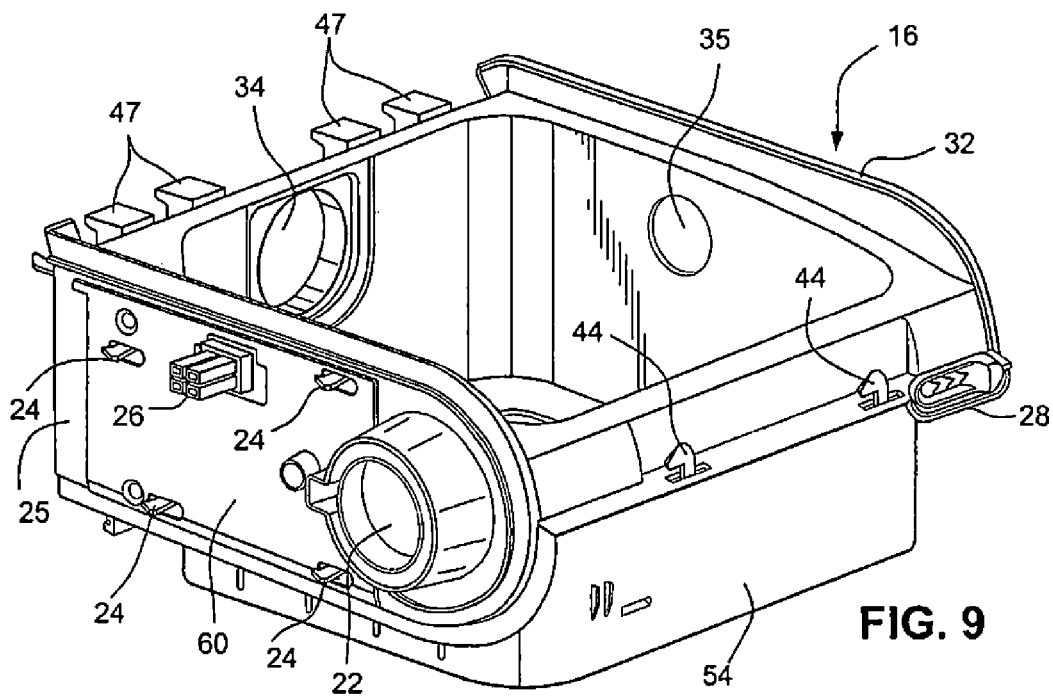
FIG. 9 schematically depicts the humidifier cradle and humidifier bottom of FIG. 8 in an assembled configuration.

As shown in FIGS. 8 and 9, the humidifier cradle 32 is supported by a chamber bottom 54 of the humidifier chamber 16. The chamber bottom 54 comprises a pair of latches 56 that are configured to engage corresponding catches (not shown) on the back of the humidifier cradle 32 to secure the humidifier cradle 32 to the chamber bottom 54. The chamber bottom 54 also includes a bottom opening 58 through which the bottom of the humidifier cradle 32 extends. The chamber bottom 54 is configured to cover the wires 52 and the lid closure member 42 when connected to the cradle 32, as shown in FIG. 8.

Figure 10:
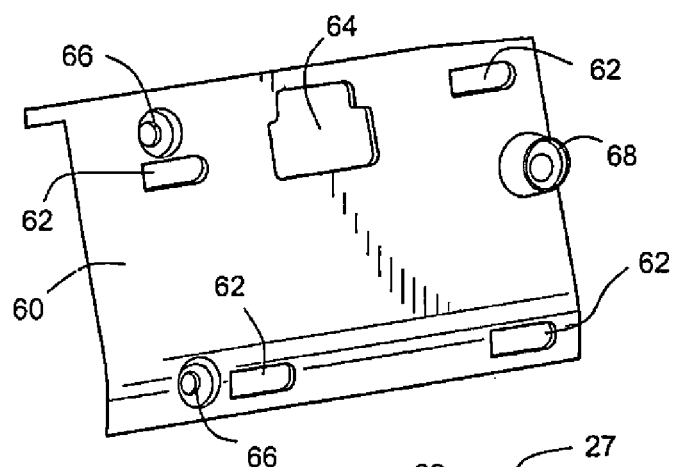
FIG. 10 schematically depicts an inner plate of the humidifier of FIG. 1.
Figure 11:
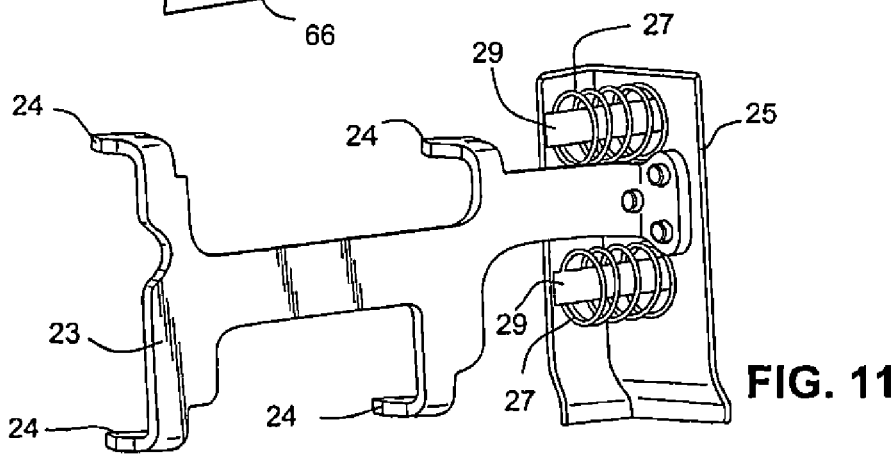
FIG. 11 schematically depicts a latch plate of the humidifier of FIG. 1.

Referring to FIGS. 9-11, an inner plate 60 may be secured to the humidifier cradle 32 over the latches 24 and the electrical connection 26. As shown in FIG. 10 the inner plate 60 includes a plurality of apertures 62 that are configured to allow the latches 24 to extend therethrough and an aperture 64 configured to allow the electrical connector 26 to extend therethrough. The inner plate 60 also comprises a pair of apertures 66 that are configured to receive fasteners, for example, threaded fasteners 80 (FIG. 15), to secure the inner plate 60 to the humidifier cradle 32. A boss 68 may also be provided on the inner plate 60 to receive a fastener, for example, a threaded fastener 80 for securing the inner plate 60 to the humidifier cradle 32. The inner plate 60 provides spillback protection to prevent water spilling back from the humidifier 14 to the flow generator 12.

As shown in FIG. 11, the latches 24 are provided on a latch plate 23 that is provided between the humidifier cradle 32 and the inner plate 60. An end of the latch plate 23 is secured to a plate 25 that is also provided between the humidifier cradle 32 and the inner plate 60. The plate 25 comprises posts 29 that support springs 27 that are configured to bias the latch plate 23 so that the latches 24 extend through the apertures 62 of the inner plate 60 in the positions shown in FIG. 9. When the humidifier 14 is connected to the flow generator 12 the latches 24 engage catches (not shown) provided on the flow generator 12 and the latches 24, and subsequently the latch plate 23, are pushed against the bias of the springs 27 (to the right in FIG. 9). Once the latches 24 fully engage the catches, the springs 27 bias the latch plate 23 and the catches 24 back to their starting position shown in FIG. 9 with the latches 24 engaged with the catches of the flow generator 12. When the humidifier 14 is connected to the flow generator 12, the electrical connector 26 connects with a corresponding electrical connector (not shown) in the flow generator 12 to permit the flow generator 12 to provide power and/or control signals to the humidifier 14. As shown in the figures, the electrical connector 26 may comprise a terminal, or terminals, although it should be appreciated that the electrical connector 26 may comprise a contact, or contacts, that are received in terminals in the flow generator 12.

Referring to FIGS. 12-14, the humidifier cradle 32 may comprise an outlet tube 70 provided through the outlet 34. As shown in FIG. 14, the outlet tube 70 may comprise a flange 72 that is configured to engage the back wall 55 of the humidifier cradle 32 and a groove 74 that is configured to receive a sealing ring 76 shown in FIG. 13. The outlet tube 70 may be removed to allow replacement of all wet area parts of the humidifier, for example, the tub 20 and the outlet tube 70. The outlet tube 70 may also be made out of a material that can be sterilized. It should be appreciated that the outlet tube 70 may also be disposable.

Figure 16:
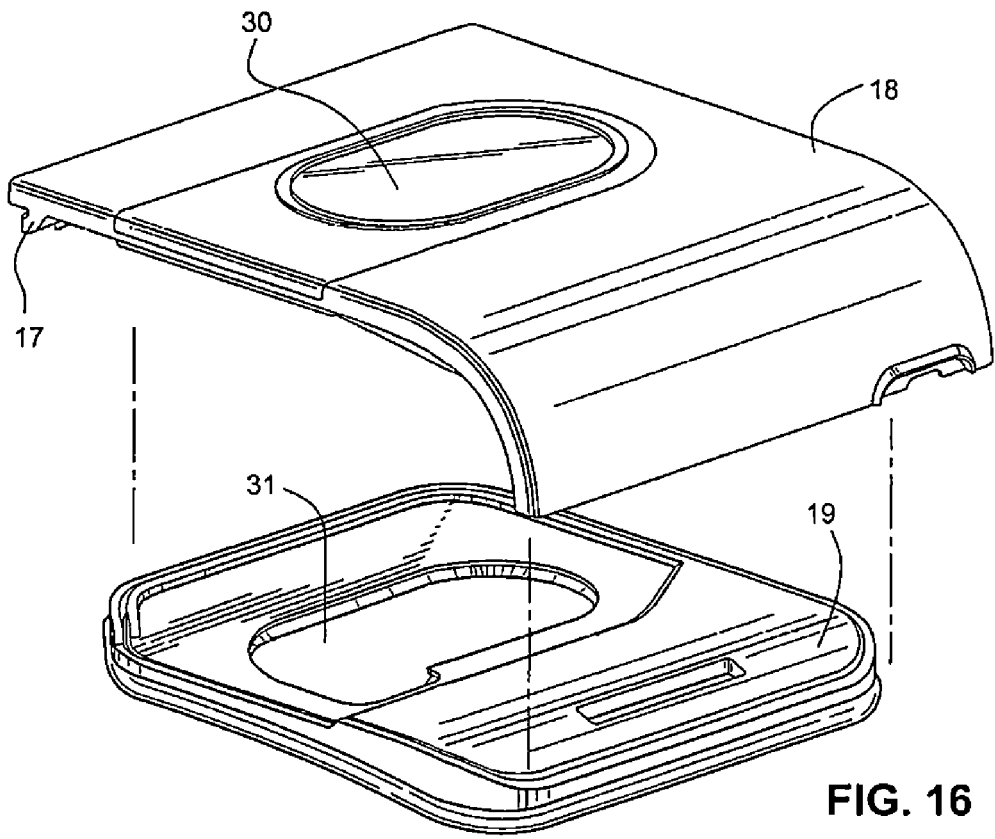
FIG. 16 schematically depicts the lid and the seal of the humidifier of FIG. 1.

Referring to FIGS. 15 and 16, in the closed position the lid 18 provided with the seal 19 allows the humidifier chamber 16 to be sealed and become pressurized by the flow generator 12 when the flow generator generates a flow of air through the inlet 22 of the humidifier 14. Pressurizing the humidifier chamber 16 reduces the pressure on the joints on the tub 20 to reduce leaks. Pressurizing the humidifier chamber 16 also reduces tolerances for insertion of the tub 20 with respect to seals on the inlet 22 and the outlet tube 70 of the humidifier chamber 16. The humidifier chamber 16 also insulates the tub 20 to provide enhanced thermal properties and reduce power consumption. Insulating the tub 20 also reduces heat loss to the surroundings. The humidity output of the humidifier is determined directly from the water temperature. As the heat loss from the tub to the surroundings is reduced due to insulating the tub, less power is needed to reach the water temperature corresponding to a desired humidity output. In addition, incoming air is pre-heated as it passes the outside walls of the tub, before it enters the tub, which also reduces the power required to reach the water temperature corresponding to the desired humidity output.

As also shown in FIG. 15, the inner plate 60 is secured to the humidifier cradle 32 by the threaded fasteners 80, although it should be appreciated that other fastening members or methods may be used to secure the inner plate 60 to the humidifier cradle 32. It should be appreciated that other latching structures and systems may be used to releasably secure the lid. For example, push to close and button to open operation systems may be used. Other examples include, but are not limited to, a rod latching system, a rotating latch or a hooking latch.

Figure 31:
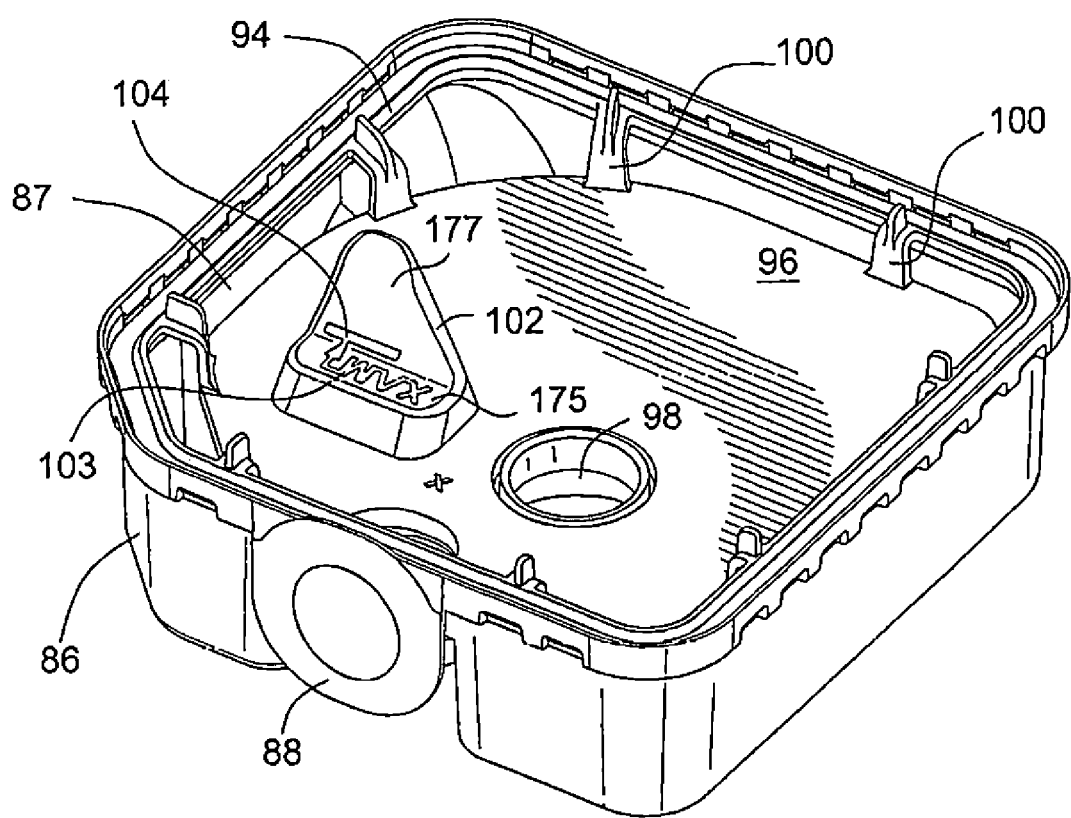
FIG. 31 schematically depicts a bottom perspective of the flow plate and the tub lid in an assembled condition.
Figure 32:
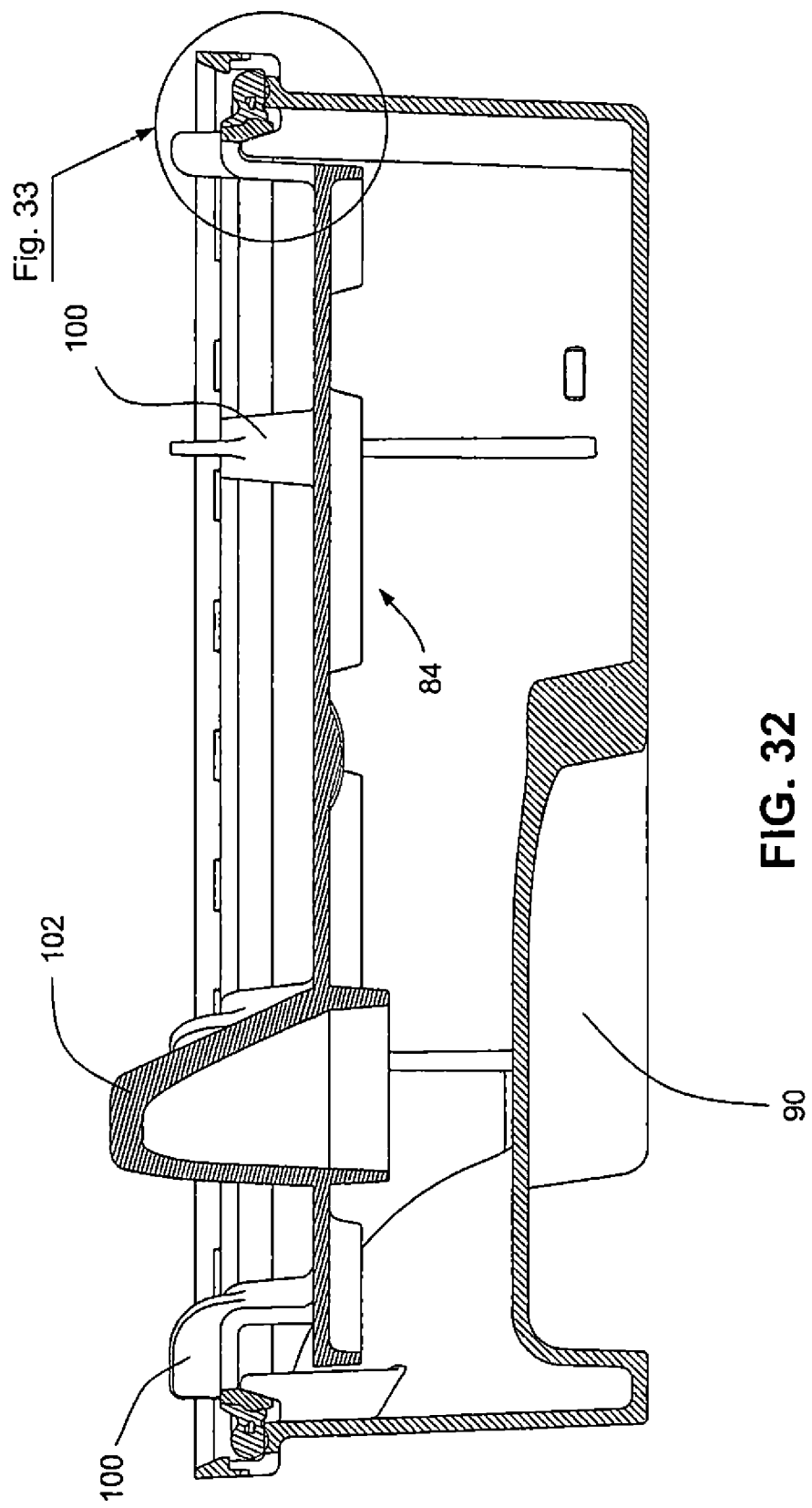
FIG. 32 schematically depicts a cross section of the flow plate and the tub lid of FIG. 31.
Figure 33:
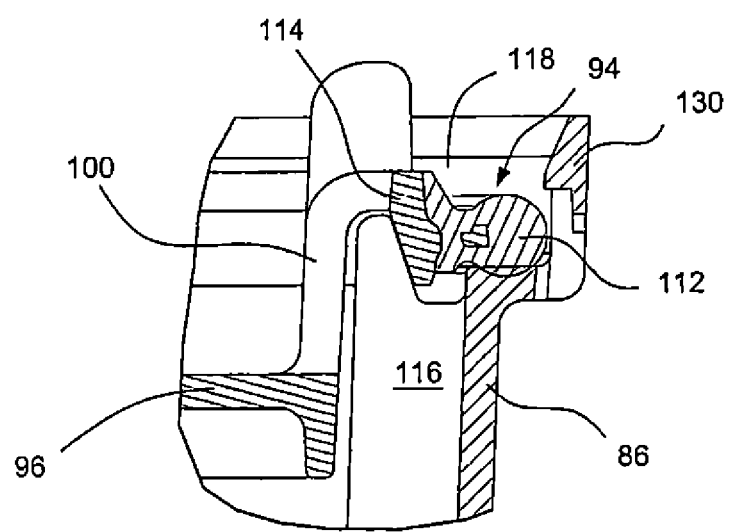
FIG. 33 schematically depicts a detailed view of the connection of the flow plate to the tub lid.
Figure 34:
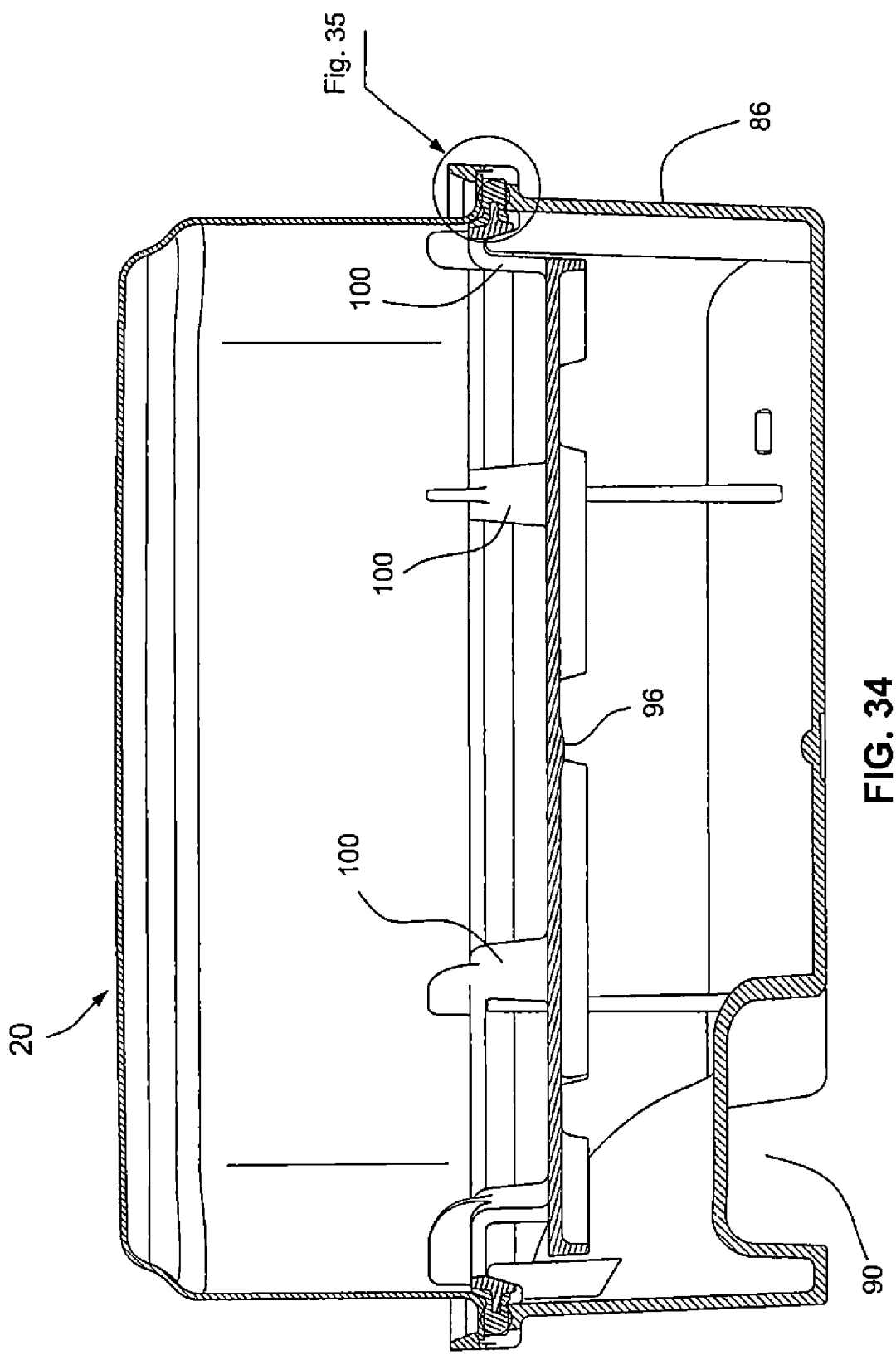
FIG. 34 schematically depicts a cross section of the tub in the assembled condition, including the tub base.
Figure 35:
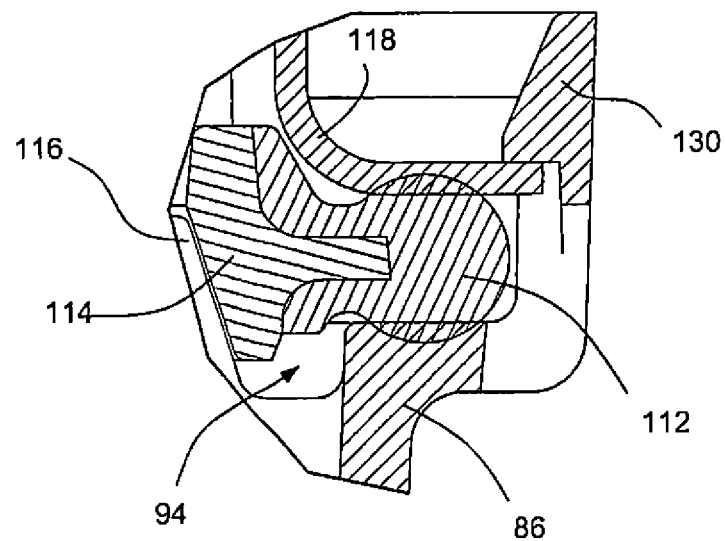
FIG. 35 schematically depicts a connection of the tub base, the flow plate, and the tub lid.
Figure 36:
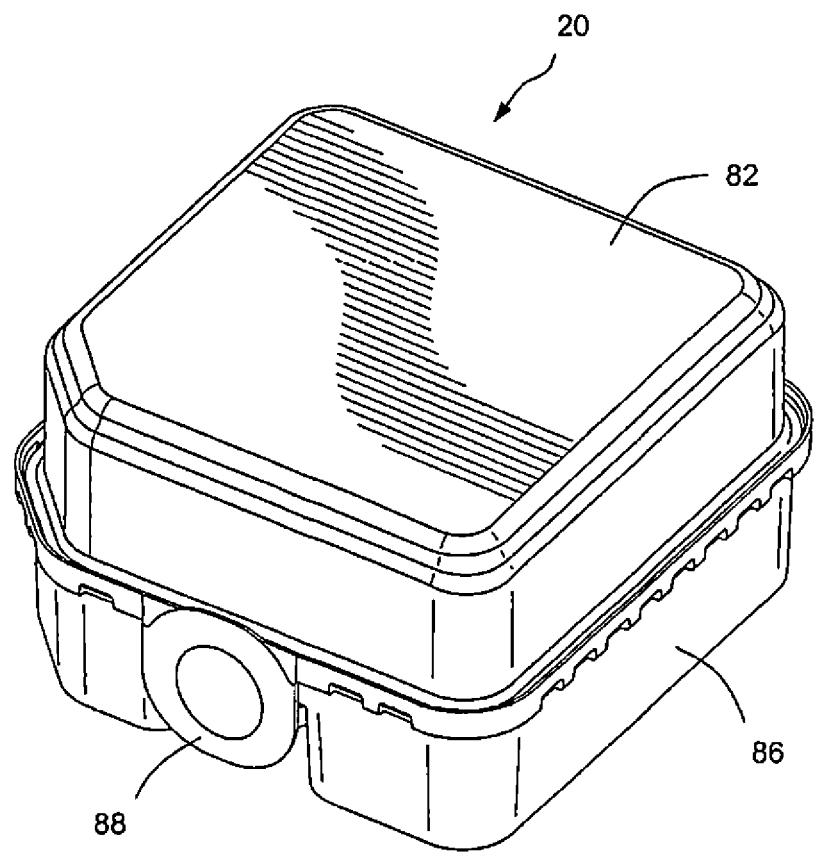
FIG. 36 schematically depicts a perspective of the tub in the assembled condition.

The outlet tube 70 and the tube connector 50 provide the ability to connect both a standard tube and a heated tube. As shown in FIG. 15, the tube connector 50 and the contacts 78 are provided separately from the outlet tube 70. A heated tube having corresponding electrical connections, e.g. terminals, may be provided in a rotational snap fit with the tube connection 50. This type of connection provides ease of connection and reduces the tolerance stack of the respiratory apparatus 10. A heated tube 134 suitable for connection to and use with the humidifier 14 is described in more detail with reference to FIG. 31. As shown in FIG. 15, a cover 132 may be connected to the back wall of the humidifier to cover the tube connector 50, and the contacts 78, when a non-heated tube is connected to the outlet tube 70. The cover 132 may be formed of a pliable rubber or other suitable flexible material. Alternatively the cover 132 may be a separate component not attached to the humidifier that may be inserted over the connector 50.

Figure 17:
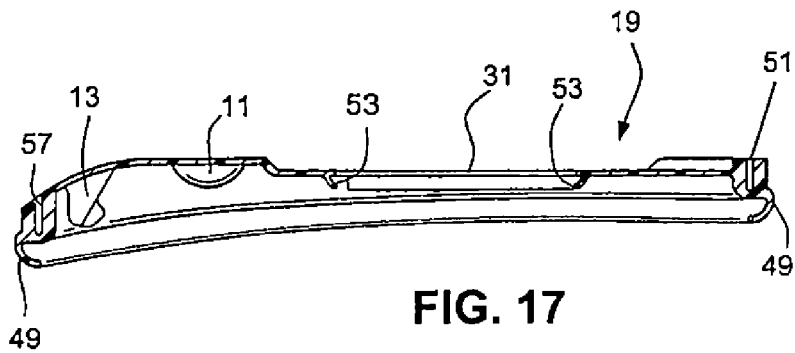
FIG. 17 schematically depicts the seal of FIG. 16.
Figure 18:
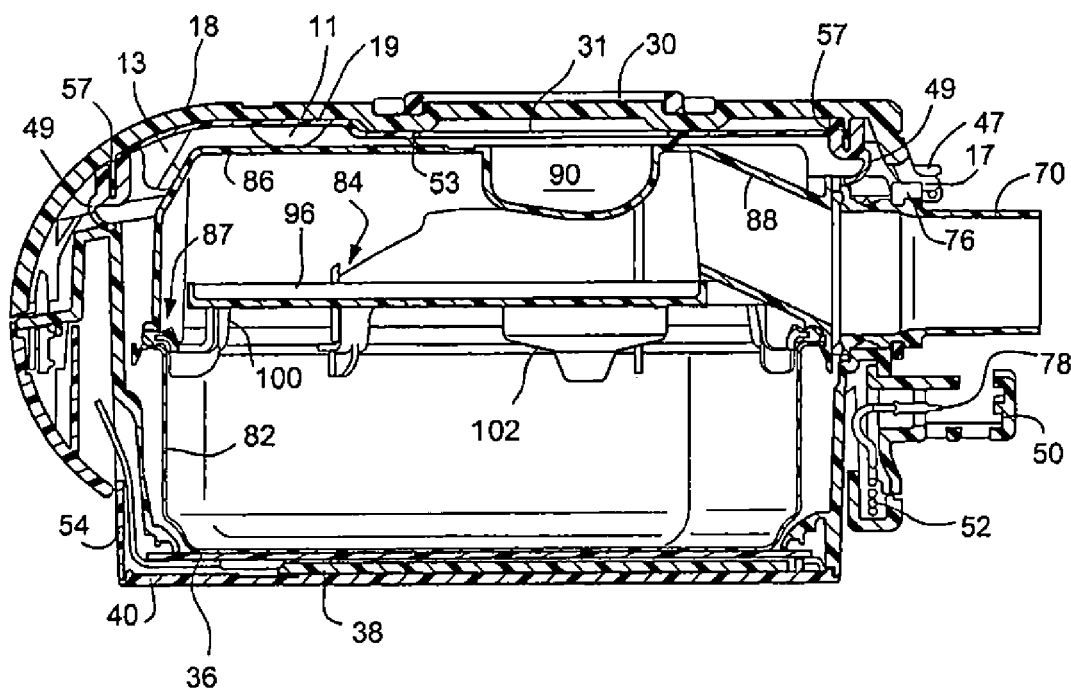
FIG. 18 schematically depicts a side view cross section of the humidifier of FIG. 1.

Referring to FIGS. 17 and 18, the seal 19 comprises a groove 51 configured to receive a corresponding edge, or rim, 57 of the lid 18 to connect the seal 19 to the lid 18. The wedge-shaped protrusions 13 (see also FIG. 3) are configured to engage the tub lid 86 when the lid 18 is in the closed position to bias the water tub 20 toward the back wall of the humidifier chamber 16 so that the outlet 88 is in sealing engagement with the outlet tube 70. The seal 19 also comprises a sealing rim 49 that extends around the perimeter of the seal 19 and is configured to seal the perimeter of the lid 18 when the lid is in the closed position. An inner sealing rim 53 is provided around the aperture 31 of the seal 19 to seal around the window 30 of the lid 18.

Humidifier Tub-Disposable-First Embodiment

Figure 19:
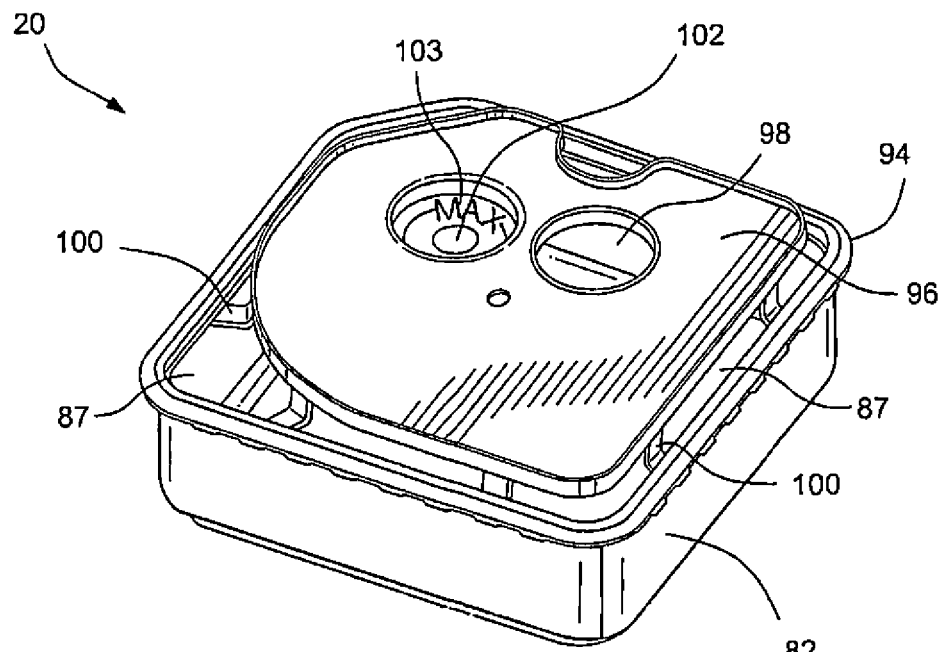
FIG. 19 schematically depicts a water tub including a tub base and a flow plate of the humidifier of FIG. 1.
Figure 20:
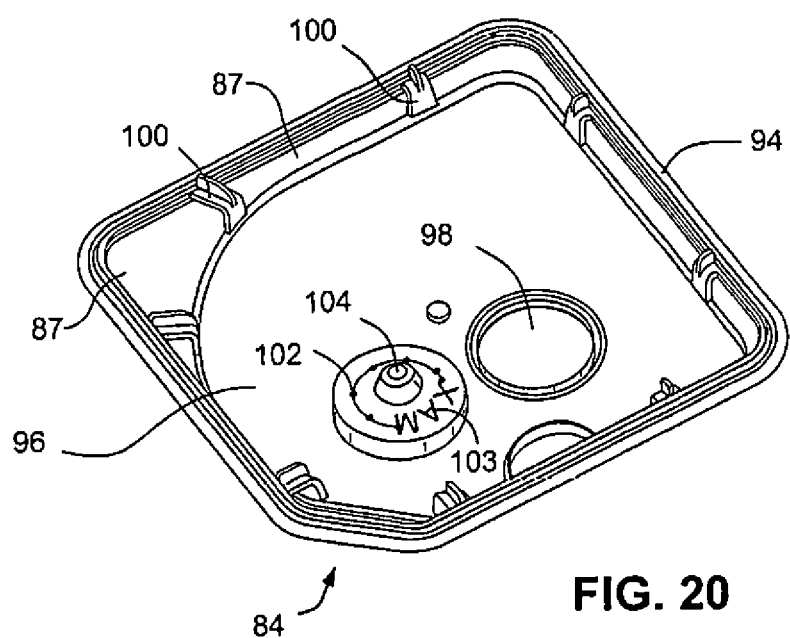
FIG. 20 schematically depicts a bottom perspective view of the flow plate of FIG. 19.
Figure 21:
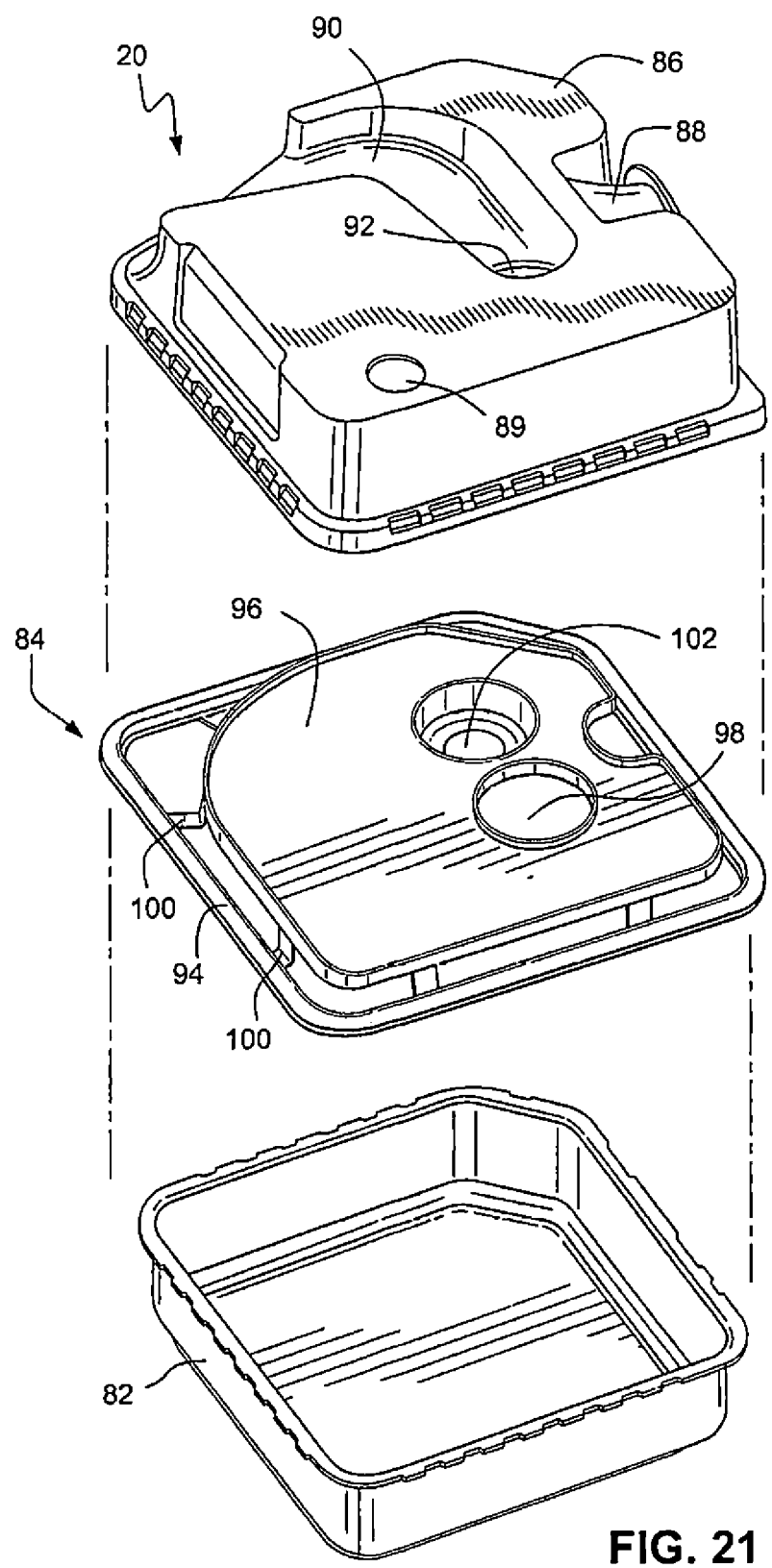
FIG. 21 schematically depicts an exploded assembly of a tub, including the tub base and flow plate of FIG. 19, according to one sample embodiment.
Figure 22:
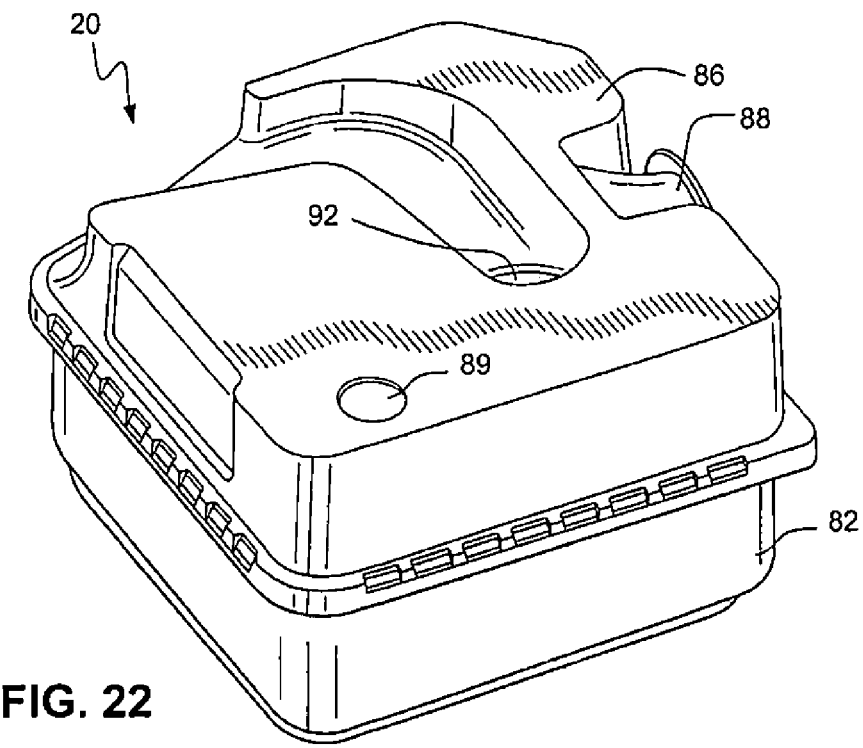
FIG. 22 schematically depicts the assembled tub of FIG. 21.

Referring to FIGS. 19 and 20, the water tub 20 comprises a tub base 82 and a flow plate 84. The flow plate 84 comprises a dividing plate 96 that comprises an inlet 98 that is configured to receive the flow of breathable gas directed by the channel 90 of the tub lid 86. The outlet 92 of the channel 90 is configured to direct the flow into the inlet 98 of the dividing plate 96 when the tub lid 86 is secured to the tub base 82 as described in more detail below.

The flow plate 84 also comprises a frame or tub seal 94 that is configured to seal the perimeter of the tub base 82 when the tub lid 86 is connected to the tub base 82. The frame seal 94 is connected to the dividing plate 96 by a plurality of supports, or bridges, 100. A gap 87 is provided between the dividing plate 96 and the frame seal 94 by the bridges 100.

Figure 23:
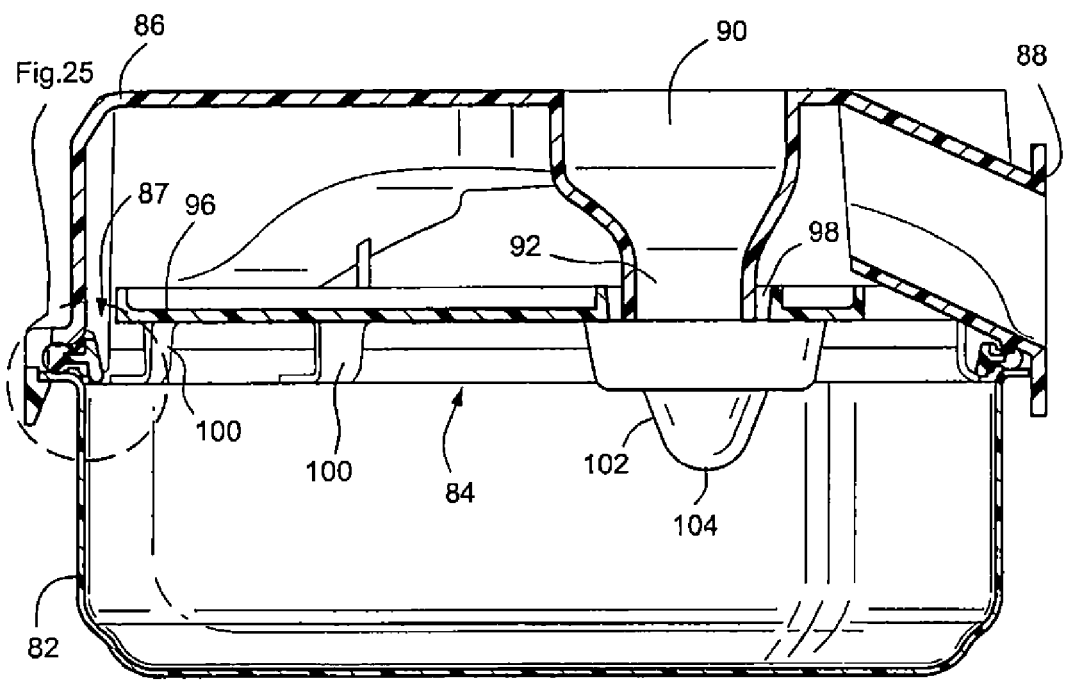
FIG. 23 schematically depicts a cross section of the tub of FIG. 22.

A water level indicator 102 is provided on the dividing plate 96 of the flow plate 84 to provide an indication of the water level. As shown in FIGS. 18-20, the water level indicator 102 may include a frusto-conical portion. As shown in FIG. 23, the water level indicator 102 may be cone shaped. A small drain hole 104 is located in the bottom of the water level indicator 102 to allow the water to fill up the water level indicator 102 and then drain out of the bottom of the water level indicator 102 to the tub base 82 as the water level decreases in the tub base 82. The water level indicator 102 provides an indication of the water level in the tub 20 by the water level indicator 102 being filled with water once the water level in the tub base 82 reaches the level of the small drain hole 102, which then allows the water level in the tub base 82 to be filled until the water in the water level indicator 102 reaches the desired level such as that indicated by indicia 103. Although the water level indicator 102 provides an indication of the water level, as the flow of breathable gas is directed to the surface of the water contained in the tub base 82, the water level is not critical as the flow is in good contact with the surface of the water. The water level indicator 102 may be provided with indicia 103 to indicate a maximum water level of the water tub 20. The light emitted from the PCB through the aperture 35 allows the water level in the water level indicator 102 to be seen.

Referring to FIGS. 21-25, according to a sample embodiment of the invention, the water tub 20 is configured to be disposable. The tub 20 comprises the tub base 82 configured to contain a supply of water. The tub lid 86 is provided on the tub base 82. The tub lid 86 may be secured to the tub base 82 by, for example, welding. The tub 20 may be formed, for example, of plastic material, metal or a combination of metal and plastic.

Figure 24:
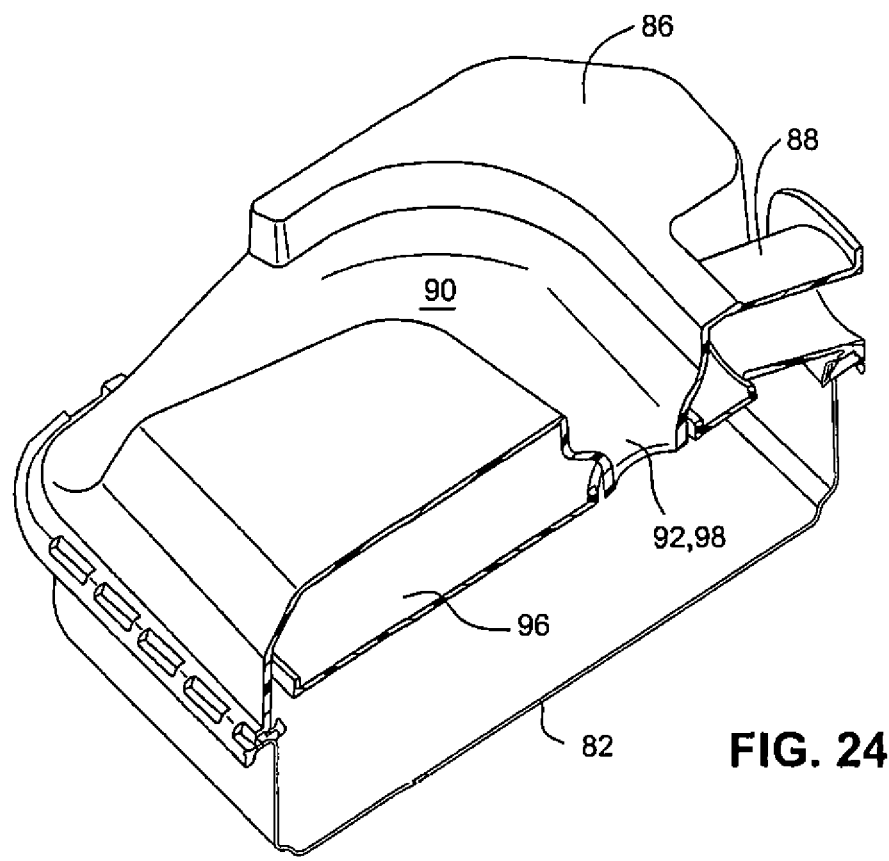
FIG. 24 schematically depicts a section view of the tub of FIG. 22.

As shown in FIGS. 23 and 24, the flow plate 84 is provided on the tub base 82. The tub lid 86 comprises the channel 90 that receives the flow of breathable gas generated by the flow generator 12 that enters the humidifier 14 through the air inlet 22. As shown in FIG. 23, the channel 90 comprises the channel outlet 92 that is received in the inlet 98 in the dividing plate 96. The dividing plate 96 ensures that the flow of breathable gas flows across the whole tub as air enters into the center and flows to the outside of the tub and then up through the gap 87 between the walls of the tub base 82 and the dividing plate 96 to the outlet 88 of the tub lid 86.

Figure 25:
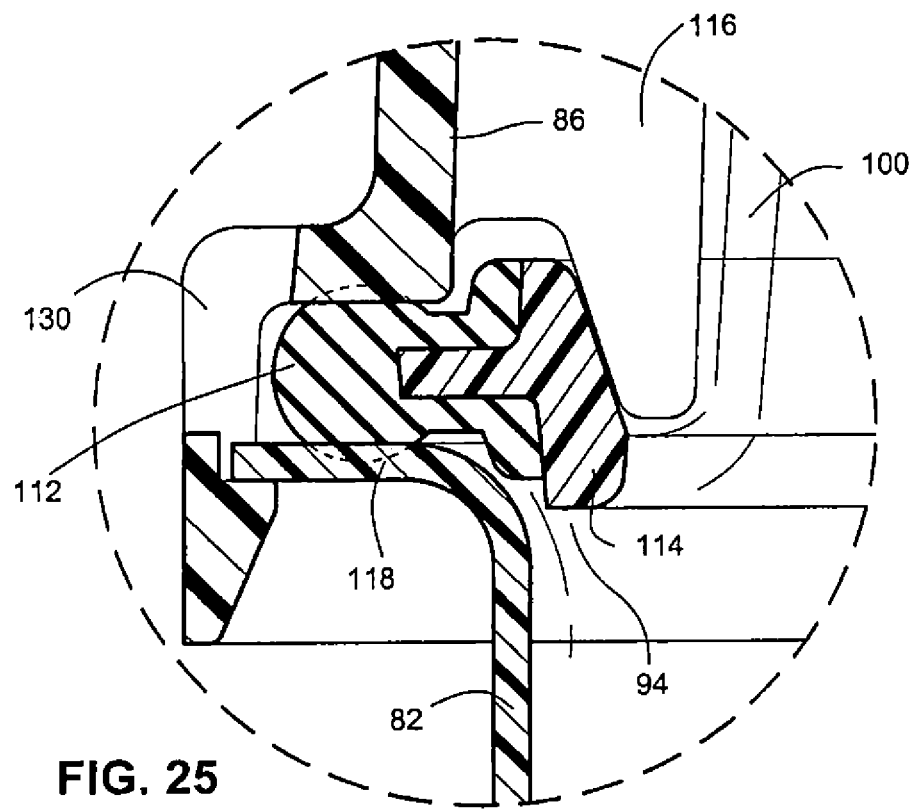
FIG. 25 schematically depicts a seal between the flow plate and the tub base of the tub of FIG. 21.
Figure 26:
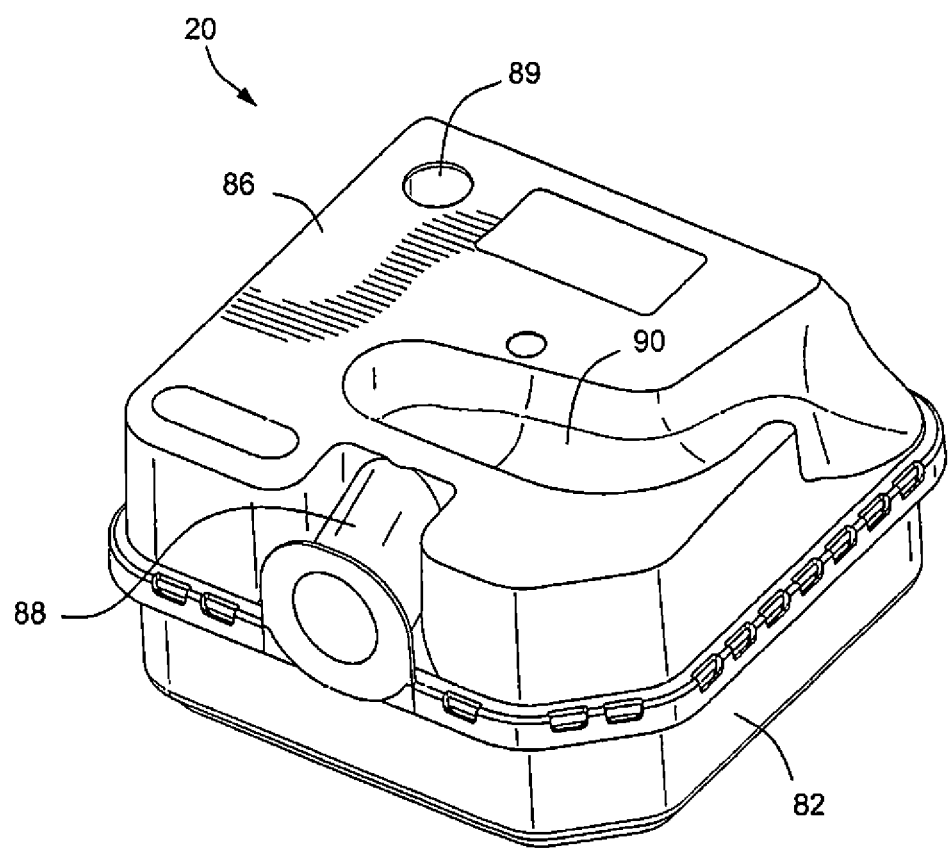
FIG. 26 schematically depicts a tub according to another sample embodiment.

Referring to FIG. 25, the tub base 82 comprises a tub base rim 118 that is engaged by a latch 130 of the tub lid 86 to connect the tub base 82 and the tub lid 86. The frame seal 94 comprises a seal 112 that is provided between the latch 130 of the tub lid 86 and the rim 118 at the tub base 82. A wedge 114 is provided on each bridge 100 and connected to the seal 112 to force the seal 112 into a sealing engagement between the rim 118 and a latch 130. The wedge 114 is engaged by a wedge 116 of the tub lid 86 to force the seal 112 into sealing engagement between the rim 118 and the latch 130.

Humidifier Tub-Disposable-Second Embodiment

Referring to FIGS. 26-49, a humidifier tub that is configured to be disposable according to another sample embodiment is illustrated. The humidifier tub 20 may comprise a tub base 82, a tub lid 86 having a channel 90. The tub lid 86 may also comprise a tub outlet 80 for delivering a humidified flow of breathable gas. A tub emptying aperture 89 may also be provided in the tub lid 86.

Figure 27:
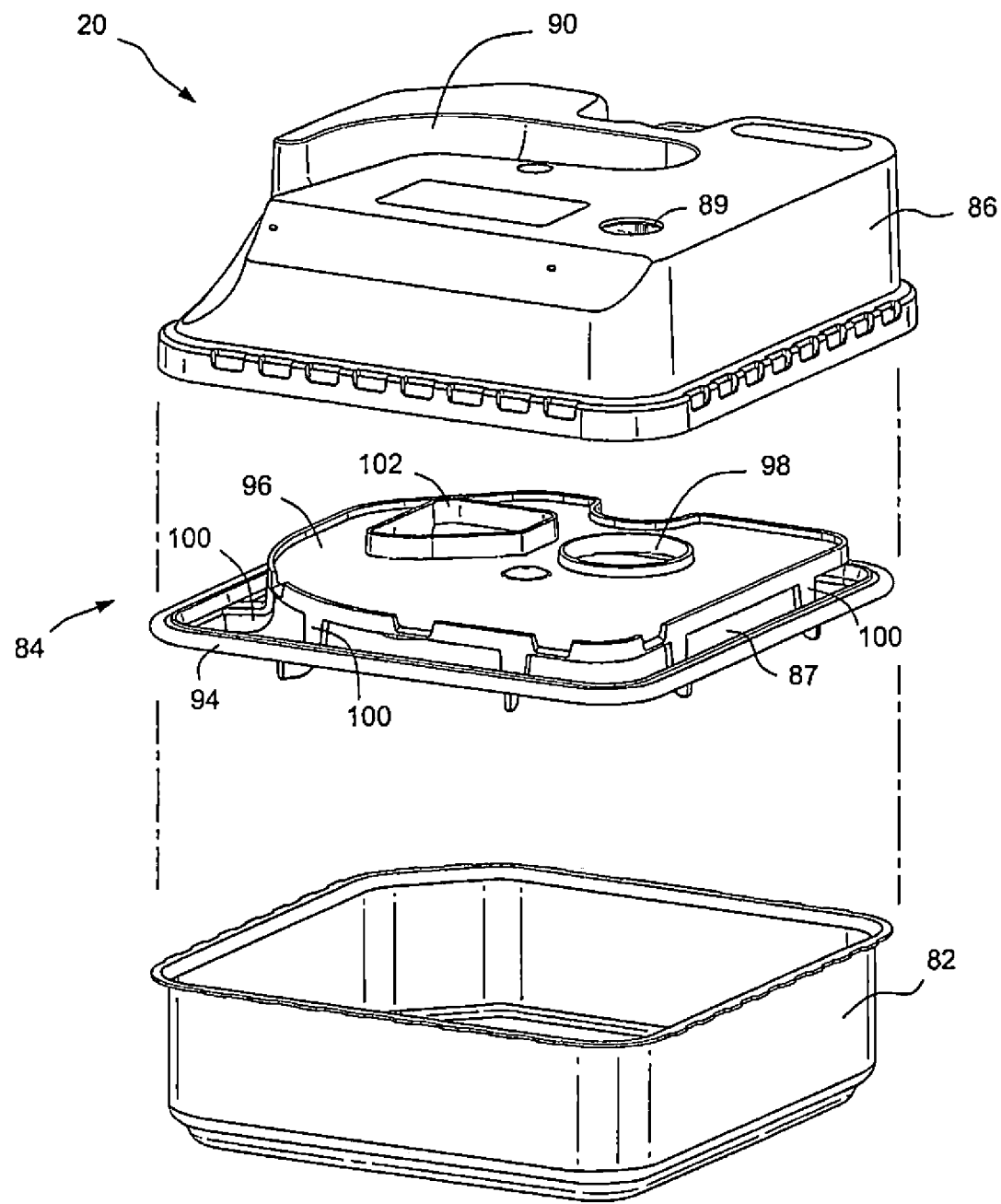
FIG. 27 schematically depicts an exploded assembly view of the tub of FIG. 26.
Figure 28:
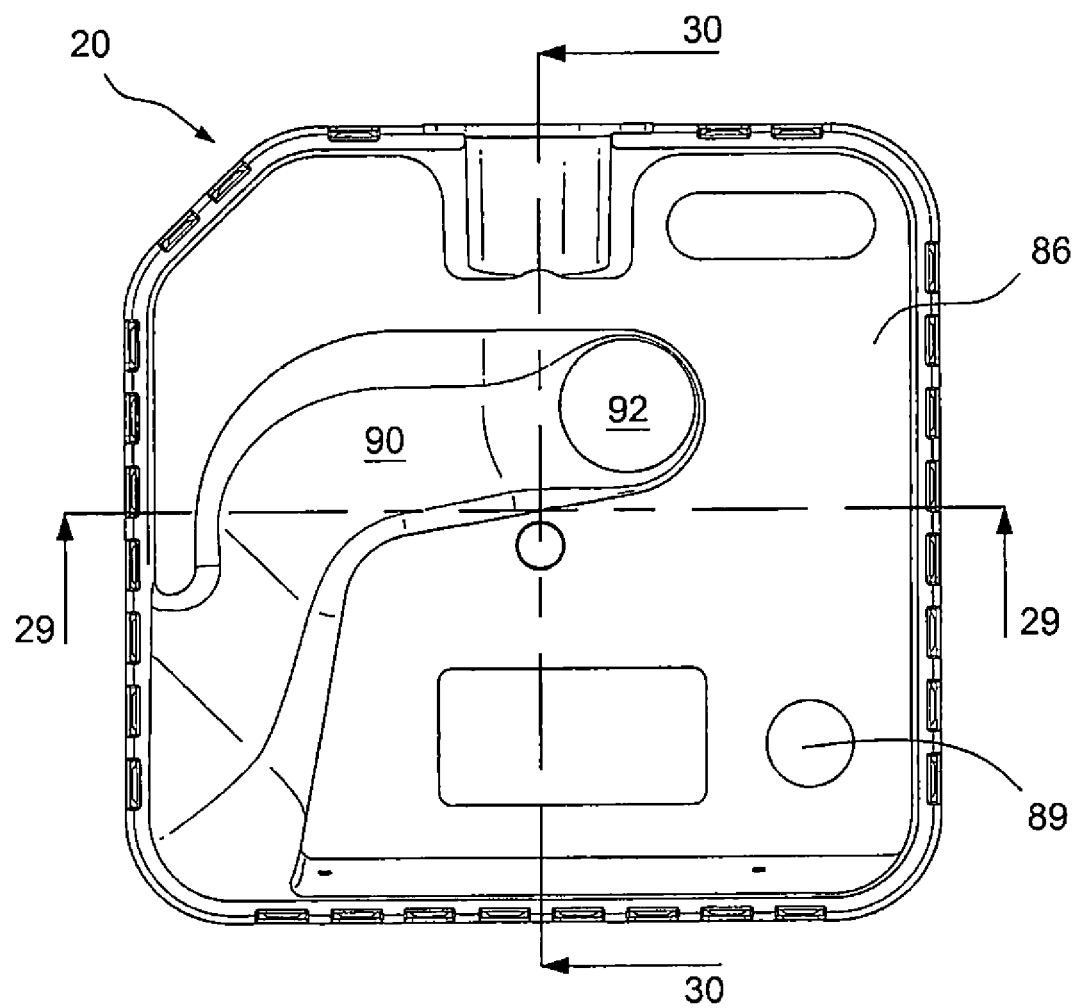
FIG. 28 schematically depicts a plan view of the tub of FIGS. 26 and 27.
Figure 29:
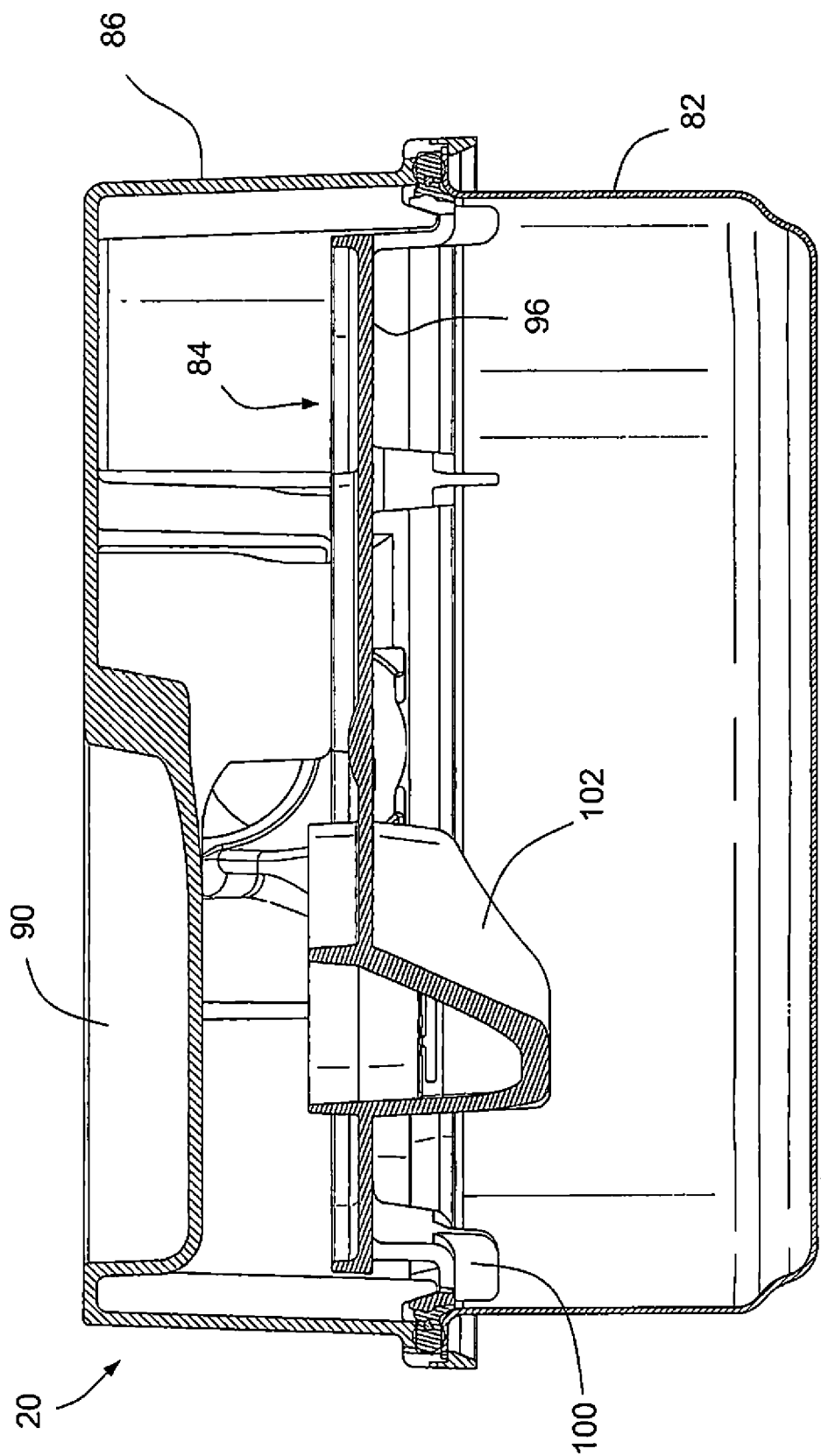
FIG. 29 schematically depicts a cross section along line 29-29.
Figure 30:
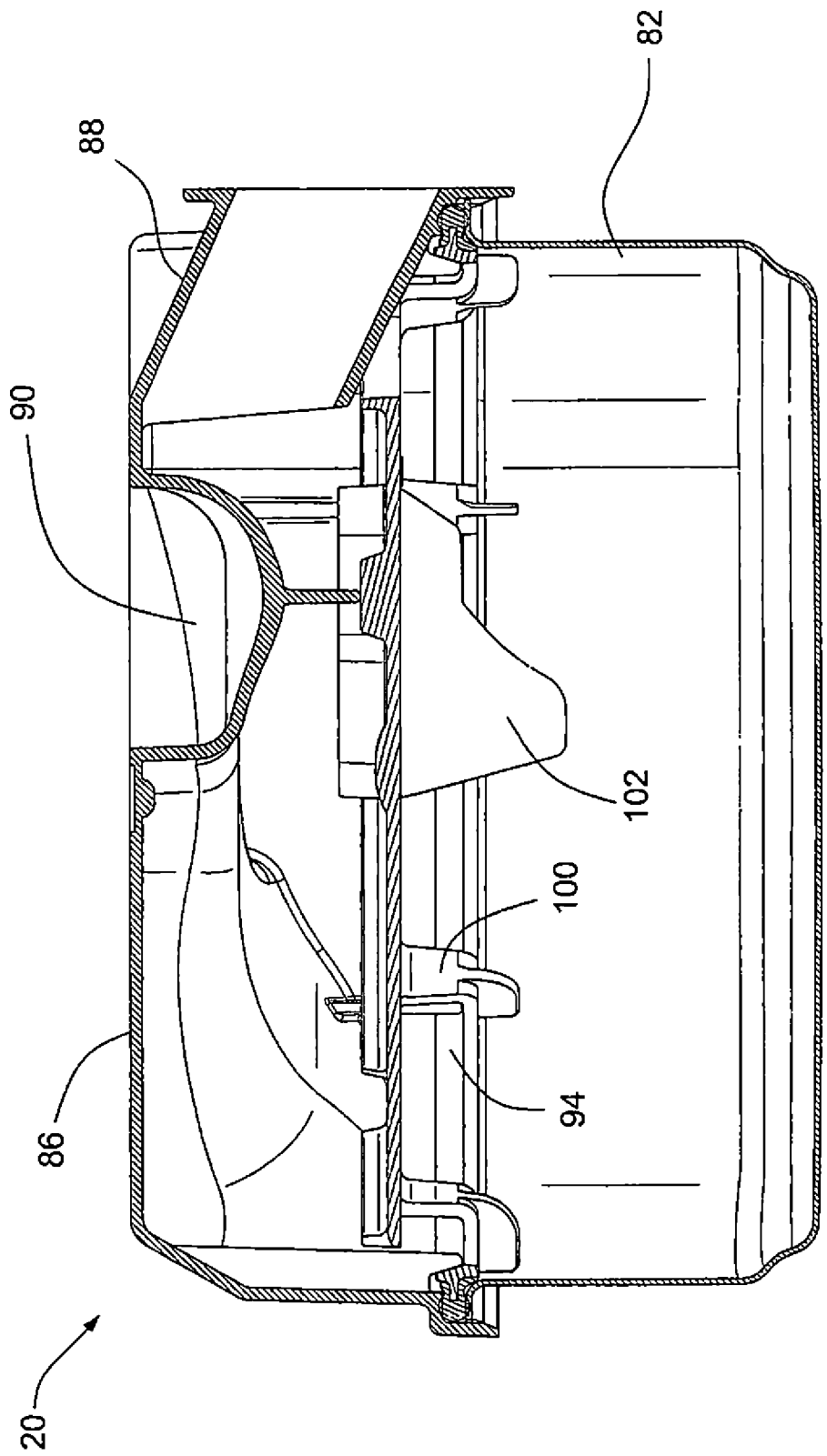
FIG. 30 schematically depicts a cross section along line 30-30.

Referring to FIG. 27, the humidifier tub 20 may also comprise a flow plate 84 having a dividing plate 96. An inlet 98 is provided on the dividing plate 96 that corresponds to the outlet 92 (FIG. 28) of the channel 90 of the tub lid 86. The dividing plate 96 of the flow plate 84 is connected to a frame seal 94 by a plurality of bridges 100. A gap 87 is provided between the frame seal 94 and the dividing plate 96.

Referring to FIGS. 27, 29, 30-32, 37-41, and 43-49, the humidifier tub 20 may also include a water level indicator 102. The water level indicator 102 may be provided on the dividing plate 96 of the flow plate 84. As shown, for example, in FIG. 39, the water level indicator 102 may have a generally polygonal perimeter, including a generally rectangular portion 175 and a generally triangular portion 177. It should be appreciated, however, that other perimeter shapes may be provided for the water level indicator 102, including regular polygonal shapes (e.g. square, rectangular, pentagonal), or polygonal shapes that are combinations of regular polygonal shapes, or polygonal shapes combined with curvilinear surfaces.

Figure 37:
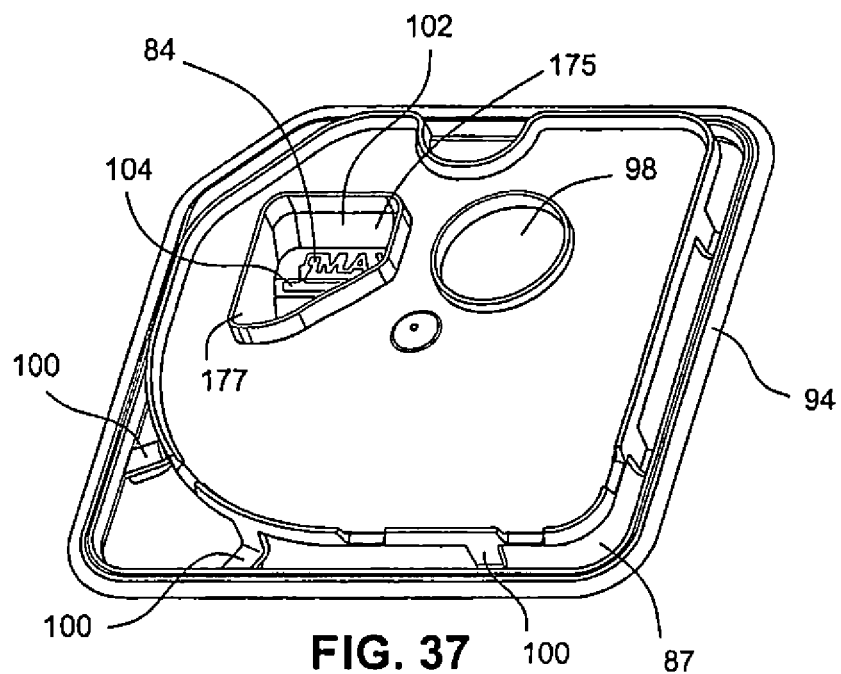
FIG. 37 schematically depicts a top perspective of the flow plate.
Figure 38:
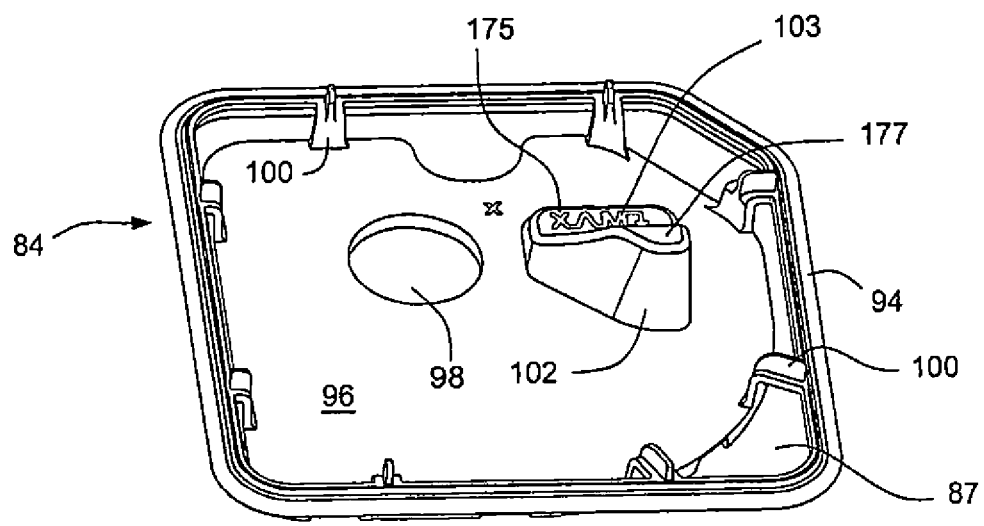
FIG. 38 schematically depicts a bottom perspective of the flow plate.
Figure 39:
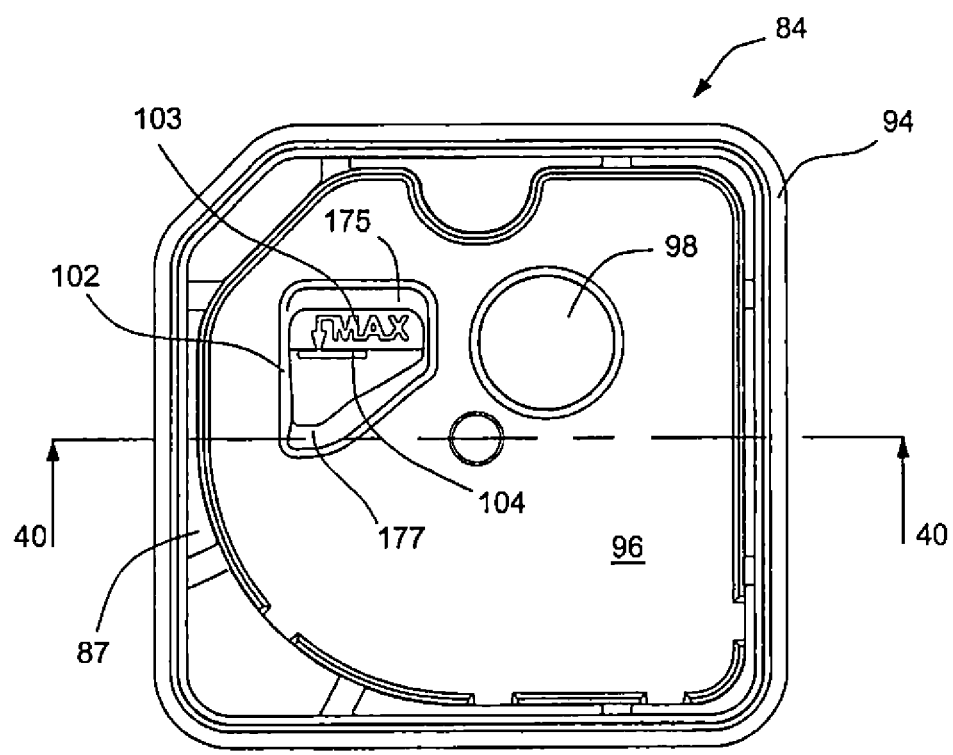
FIG. 39 schematically depicts a plan view of the flow plate.
Figure 40:
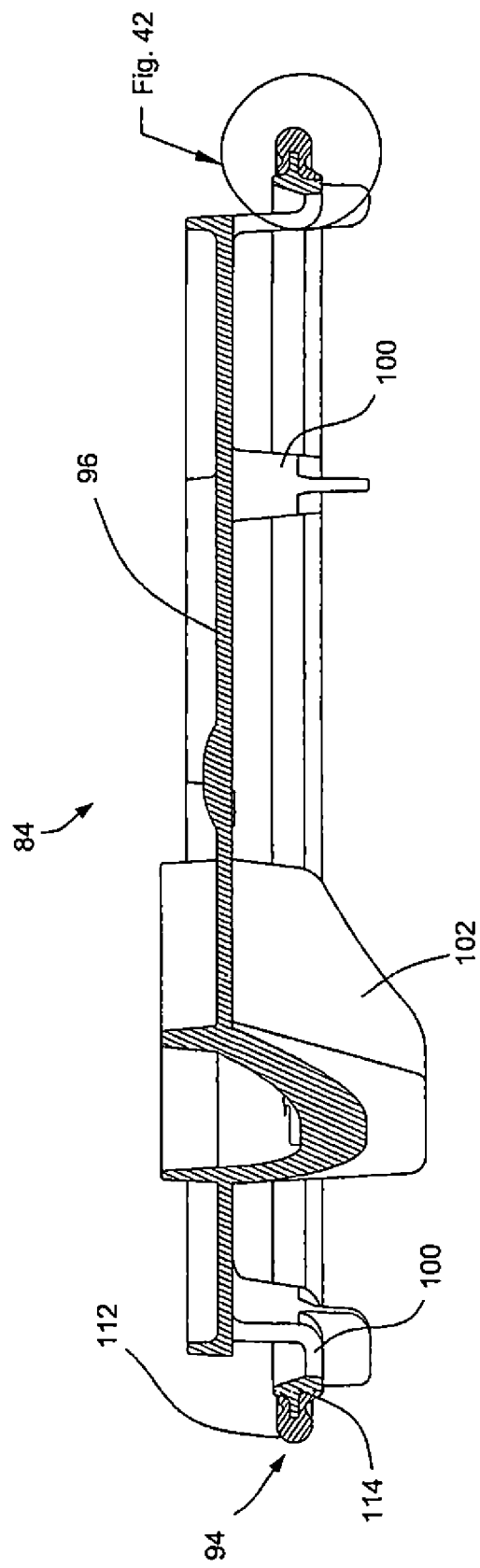
FIG. 40 schematically depicts a cross section along line 40-40.
Figure 41:
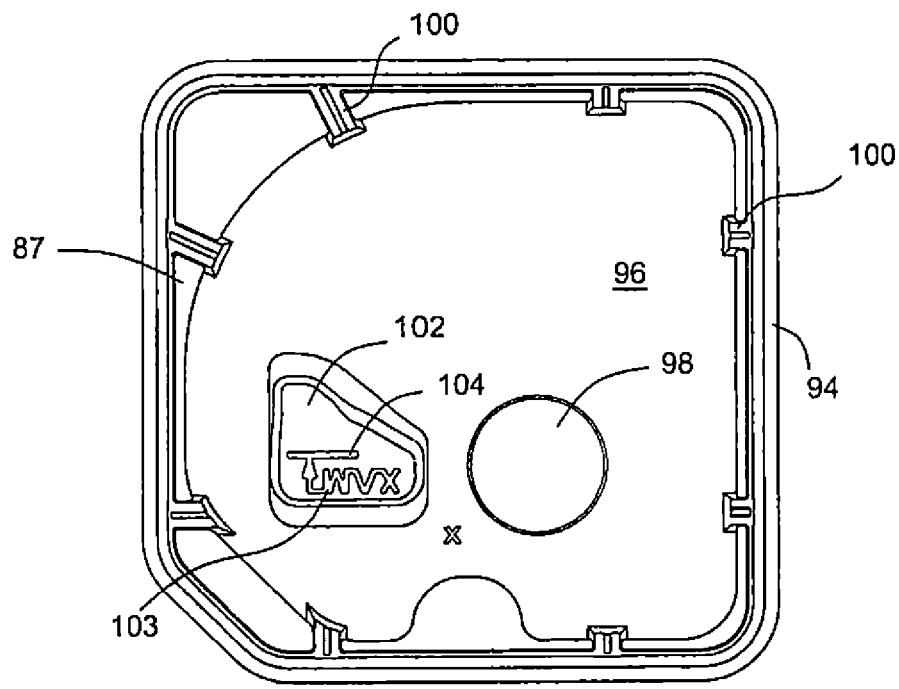
FIG. 41 schematically depicts a bottom view of the flow plate.
Figure 42:
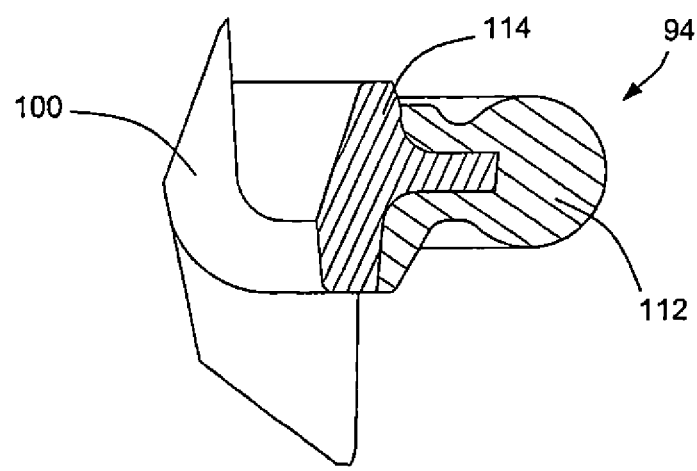
FIG. 42 schematically depicts an assembly of the flow plate and seal.
Figure 43:
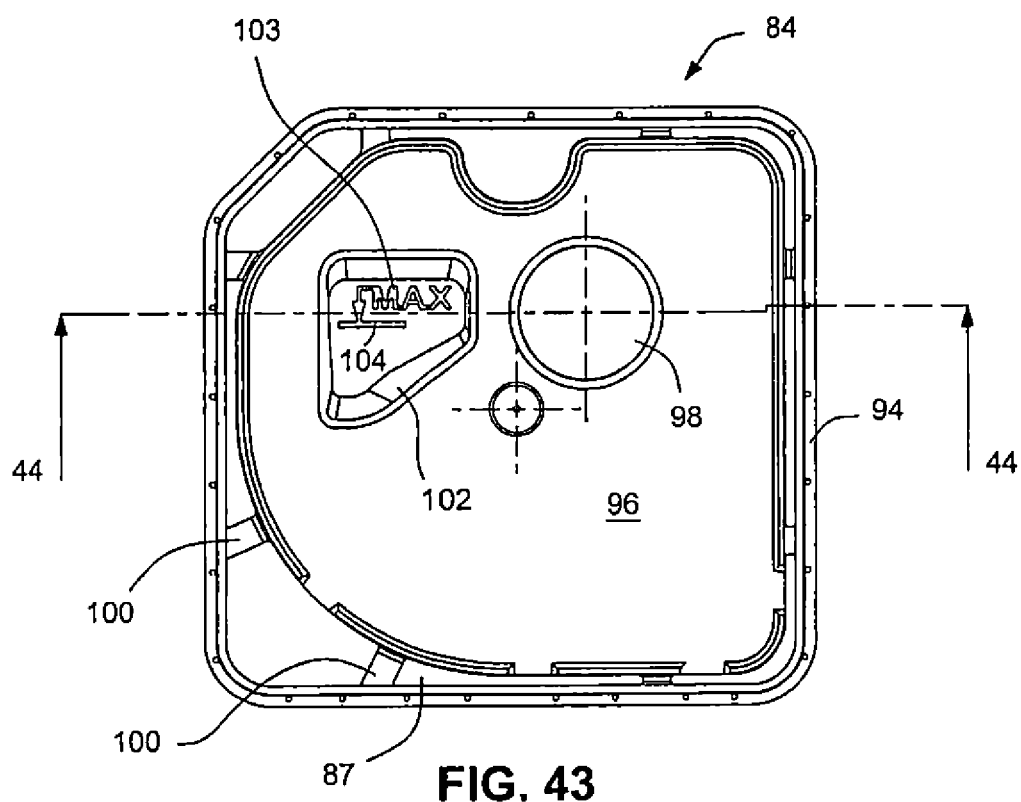
FIG. 43 schematically depicts a plan view of the flow plate.
Figure 44:
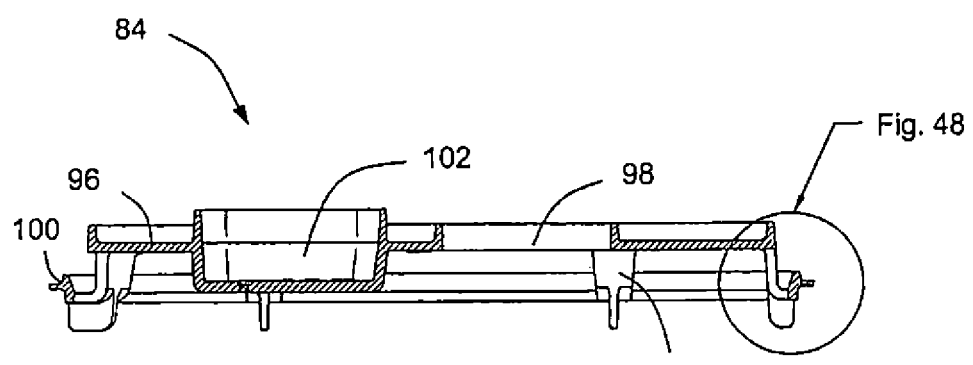
FIG. 44 schematically depicts a cross section along line 44-44.
Figure 45:
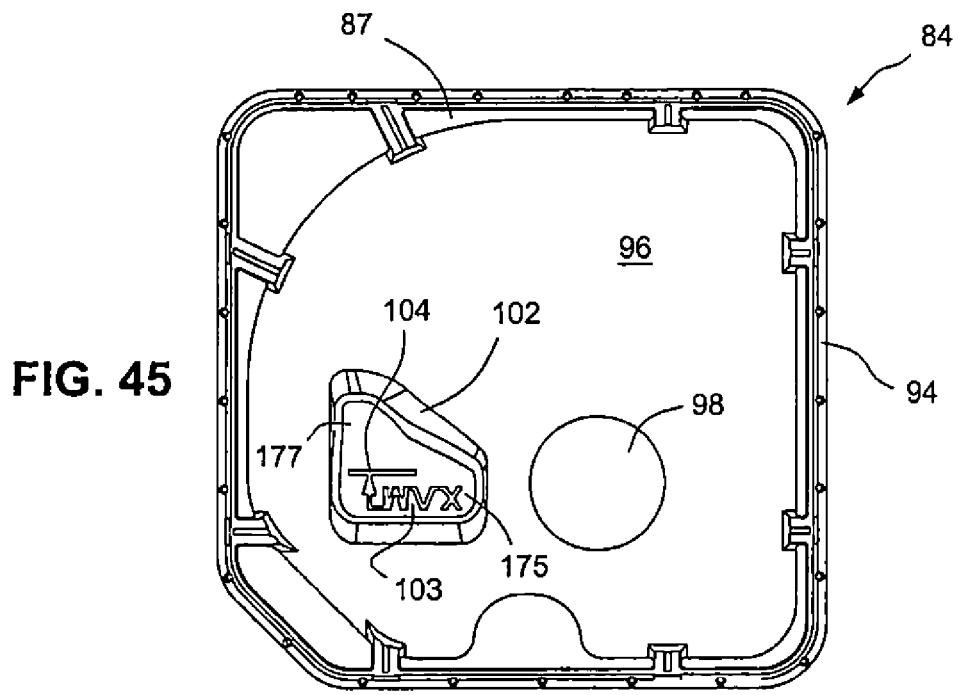
FIG. 45 schematically depicts a bottom view of the flow plate.
Figure 46:
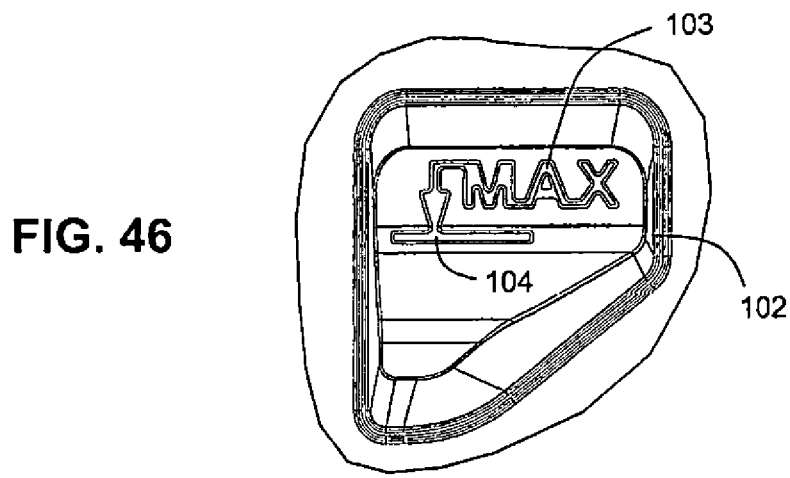
FIG. 46 schematically depicts the maximum water level indicator of the flow plate.
Figure 47:
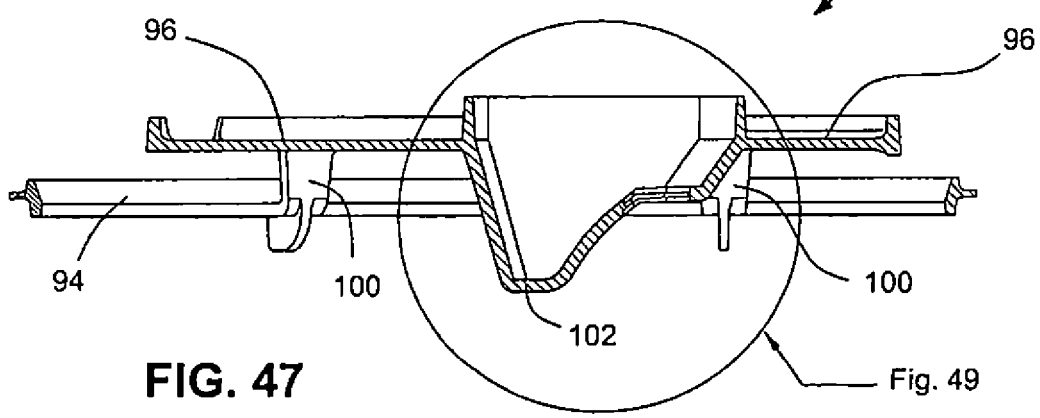
FIG. 47 schematically depicts a cross section of the maximum water level indicator on the flow plate.

As shown in FIGS. 31, 37, 39, 41, 43, 45, 46 and 49, the water level indicator 102 comprises a drain hole 104 to allow the water to drain out of the bottom of the water level indicator 102 to the tub base 82. As shown, for example, in FIG. 49, the drain hole 104 is not provided at the bottom of the water level indicator 2, but is located at an intermediate position between the bottom and the top of the water level indicator 102 to allow any pooled water to drain away from the intermediate position. In this embodiment the water level indicator 102 is not filled with water but the water level is indicated against the sloping surface of the water level indicator as described in more detail below. As shown in FIG. 37, the drain hole 104 is located at a position generally corresponding to the plane of the dividing plate 96 of the flow plate 84. As also shown in FIG. 37, and FIGS. 31, 38, 39, 41, 43, 45 and 46, the water level indicator 102 may include indicia 103 that indicates a maximum fill level of the humidifier tub 20. As shown in the figures, the indicia 103 may be provided at the same level of the water level indicator 102 as the drain hole 104.

Figure 49:
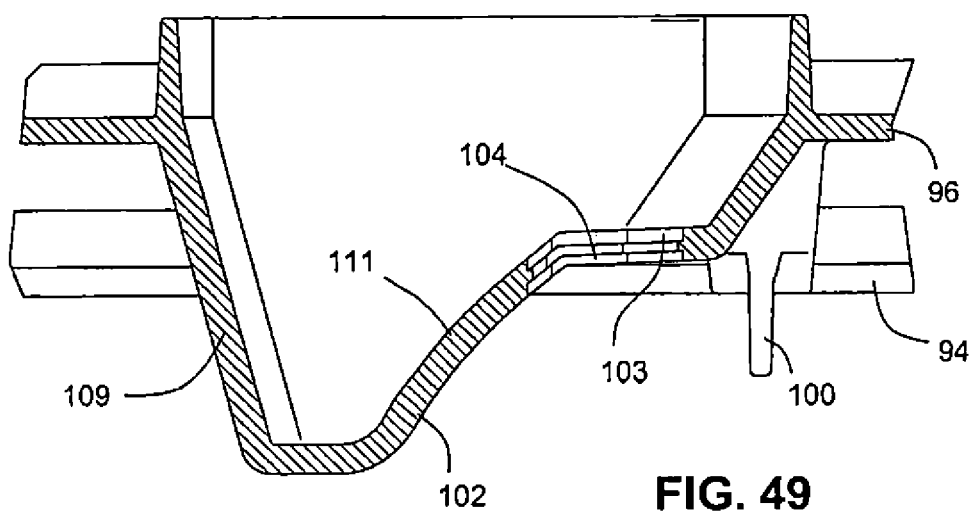
FIG. 49 schematically depicts a detailed view of the maximum water level indicator.
Figure 50:
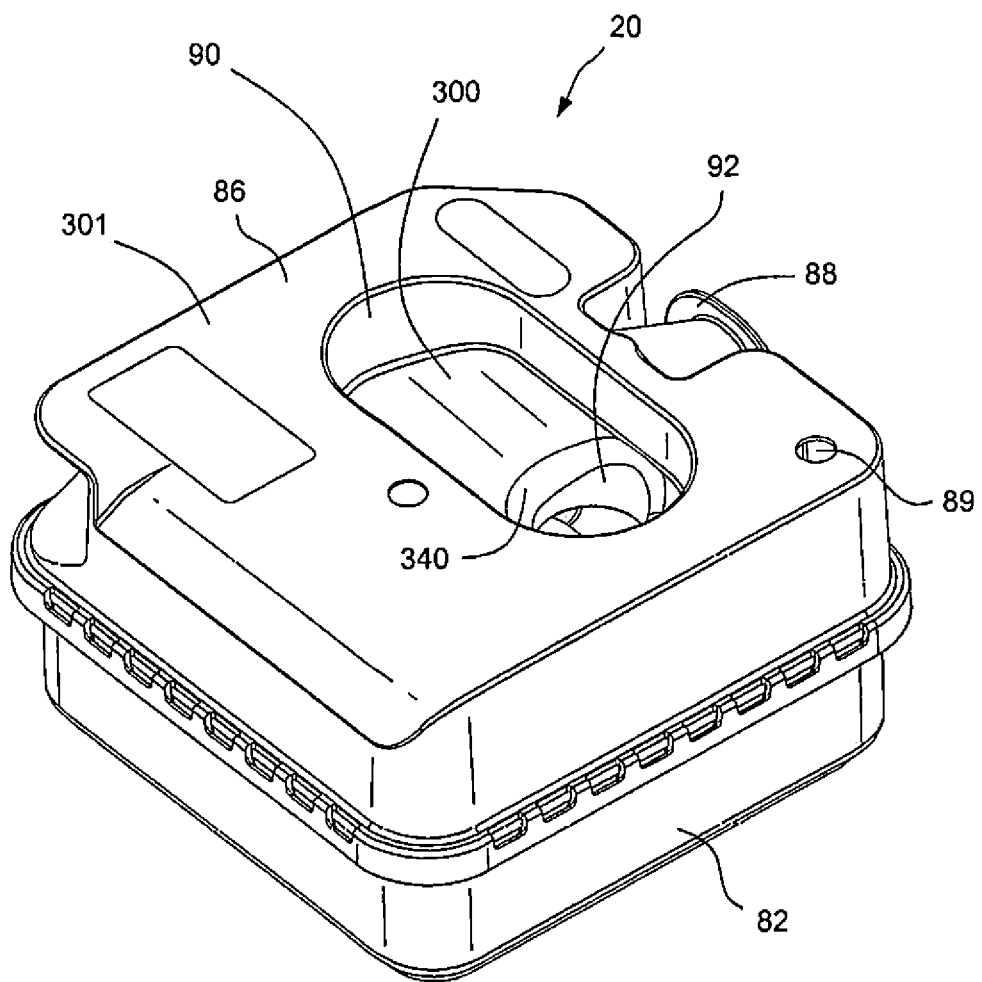
FIG. 50 schematically depicts a perspective view of a tub according to another sample embodiment.
Figure 51:
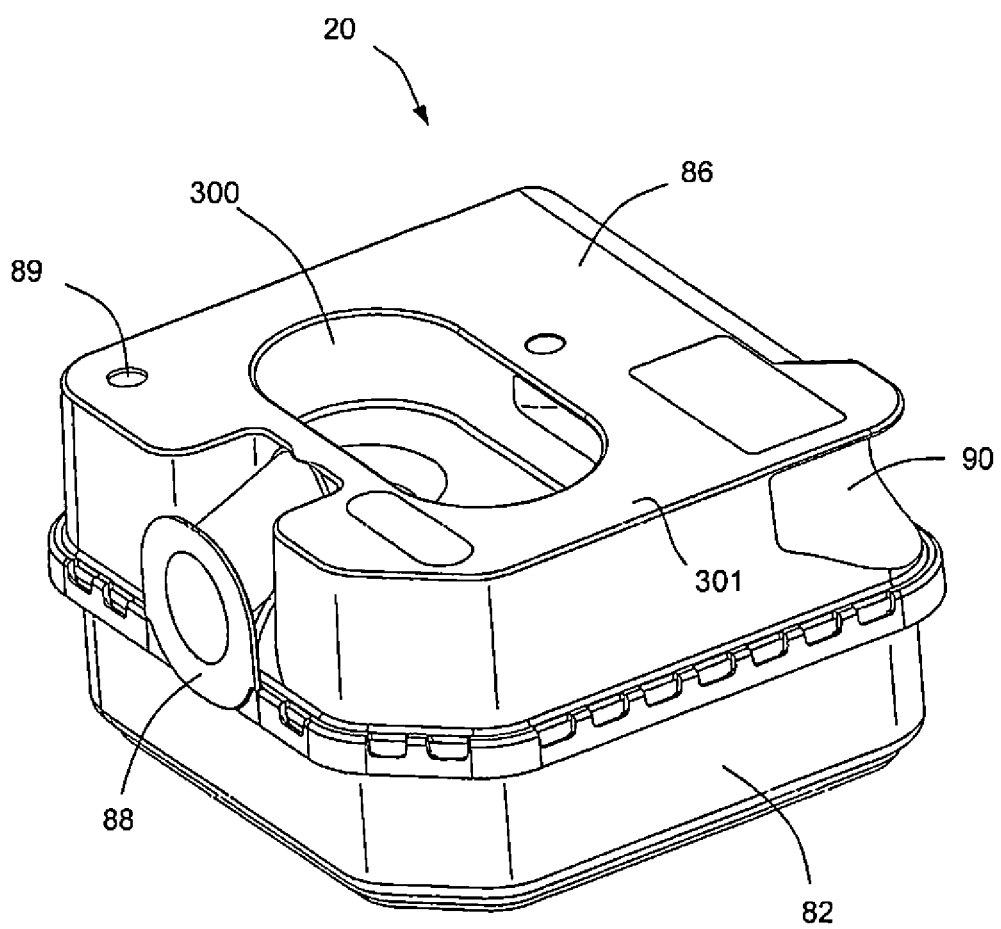
FIG. 51 schematically depicts another perspective view of the tub of FIG. 50.
Figure 52:
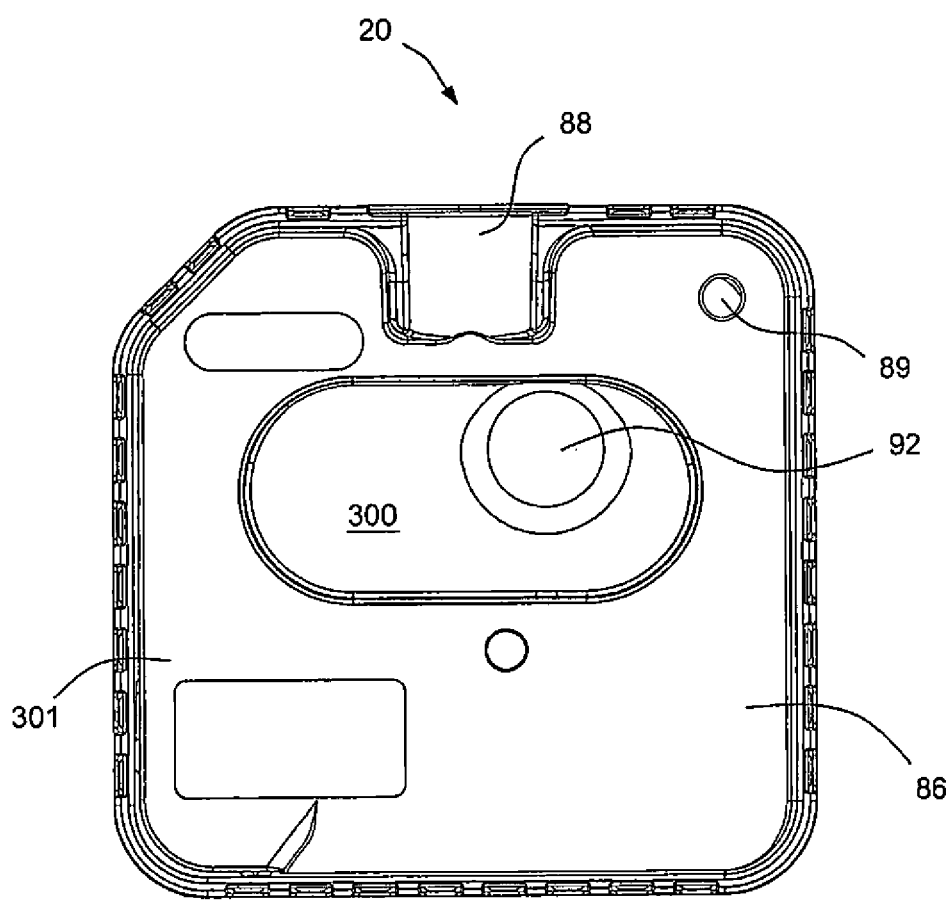
FIG. 52 schematically depicts a top view of the tub of FIG. 50.
Figure 53:
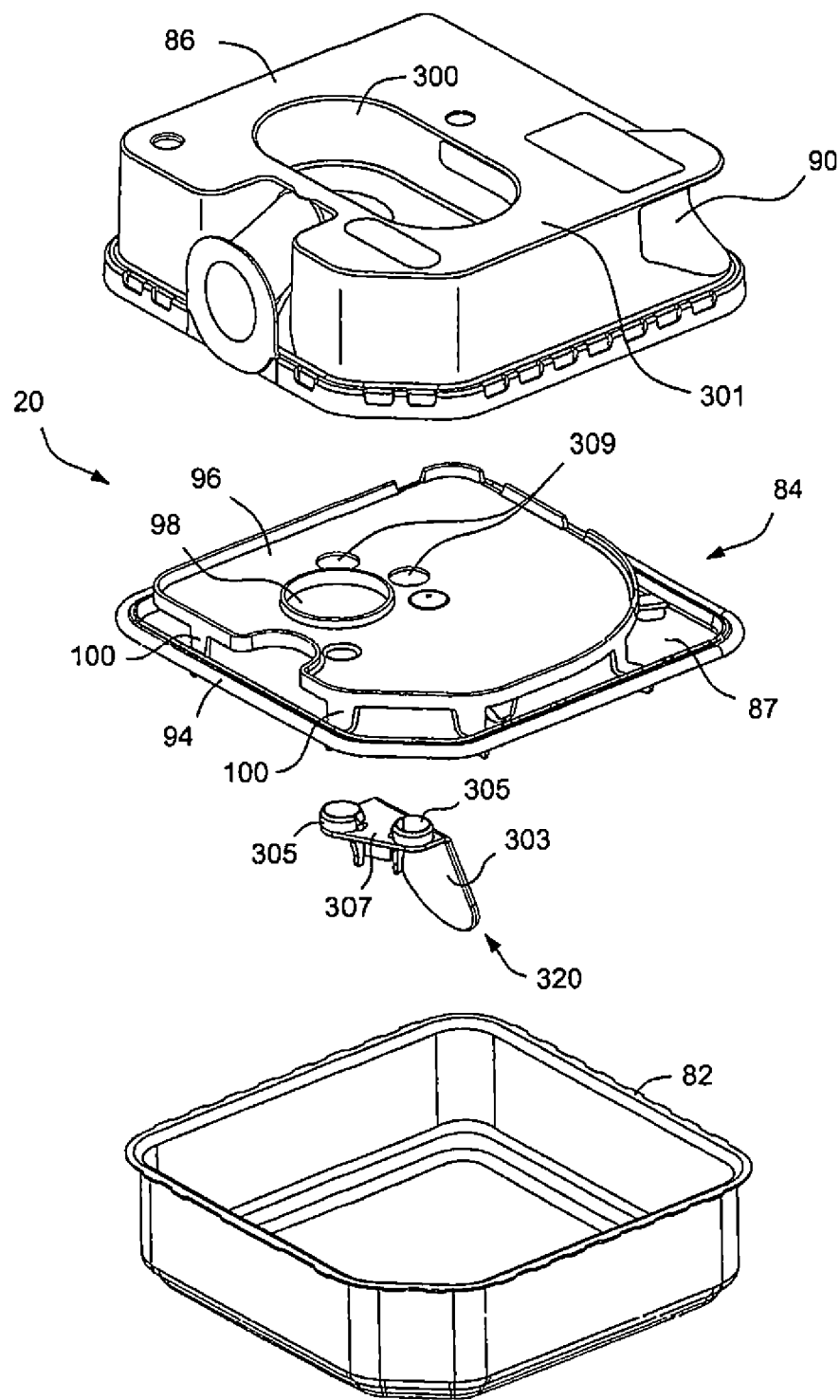
FIG. 53 schematically depicts an exploded assembly of the tub of FIG. 50.
Figure 54:
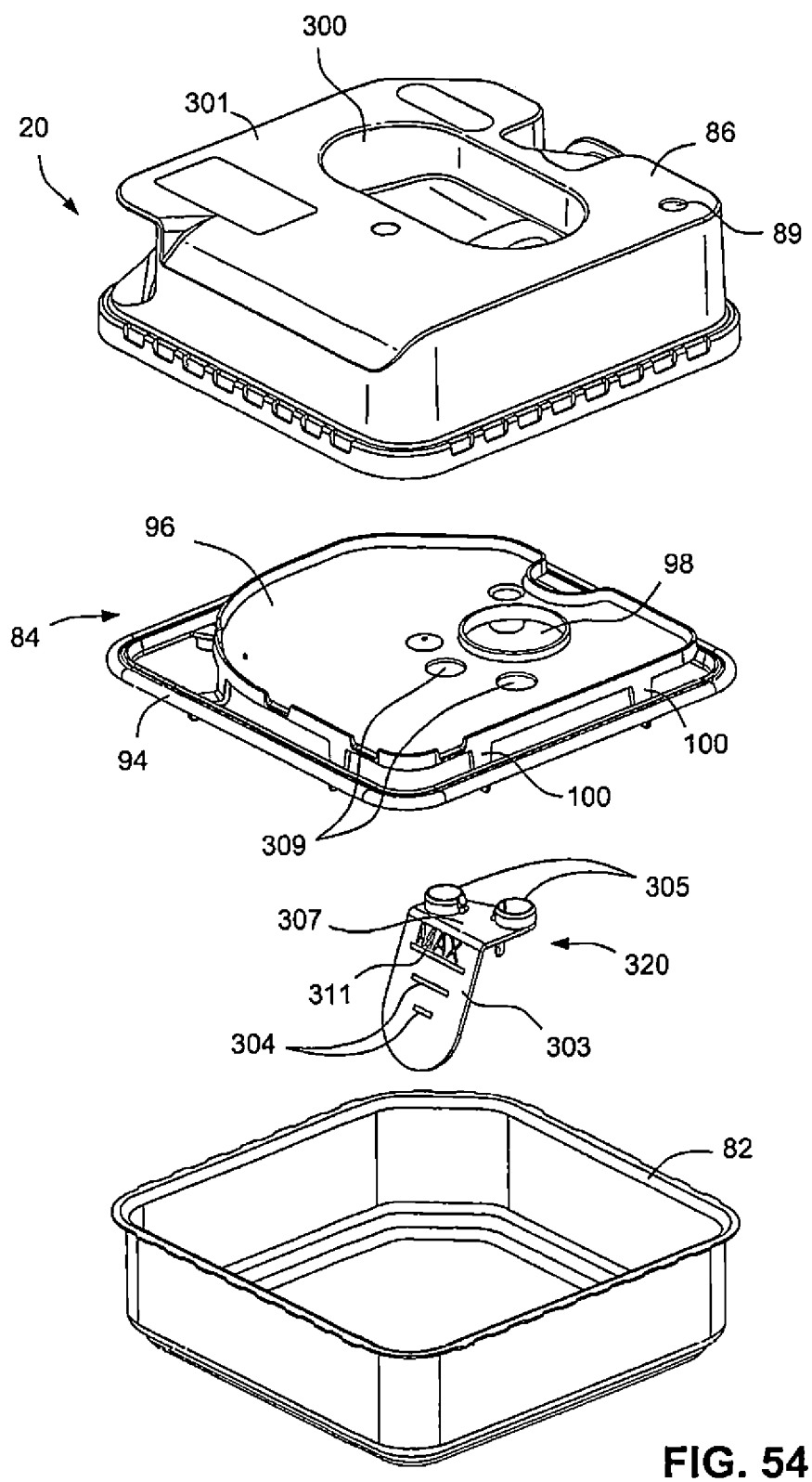
FIG. 54 schematically depicts an exploded assembly of the tub of FIG. 50 from another perspective.
Figure 55A:
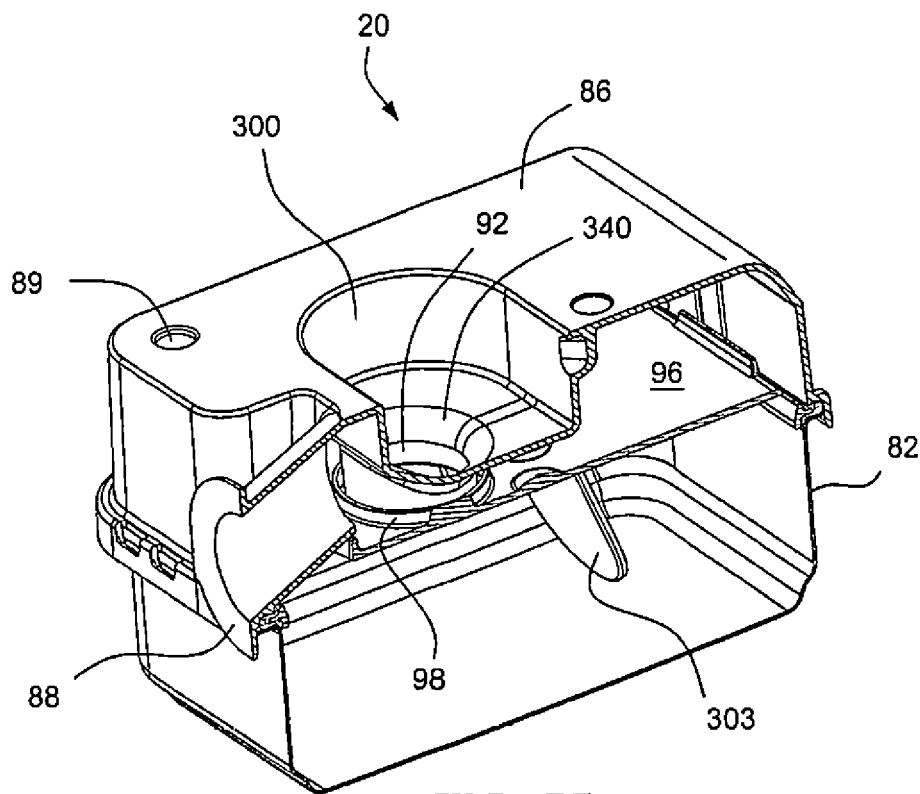
FIGS. 55a and 55b schematically depict cross sections of the tub of FIG. 50.
Figure 55B:
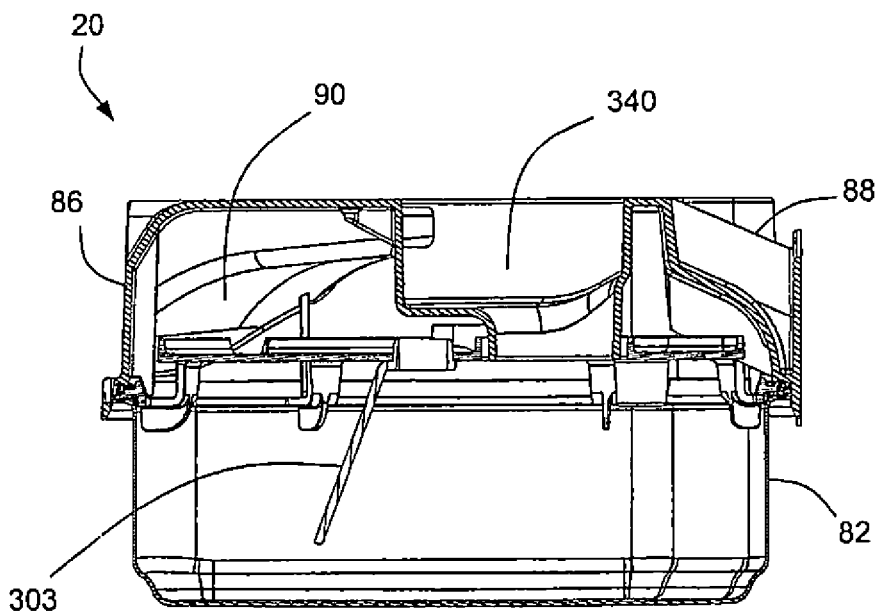
Figure 56:
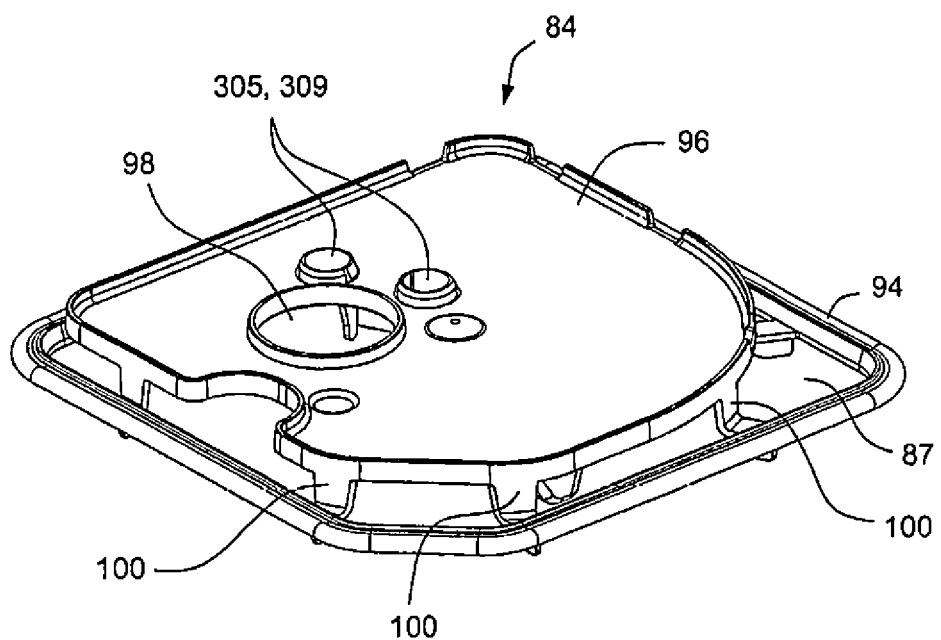
FIG. 56 schematically depicts a perspective view of a flow plate of the tub of FIG. 50.
Figure 57:
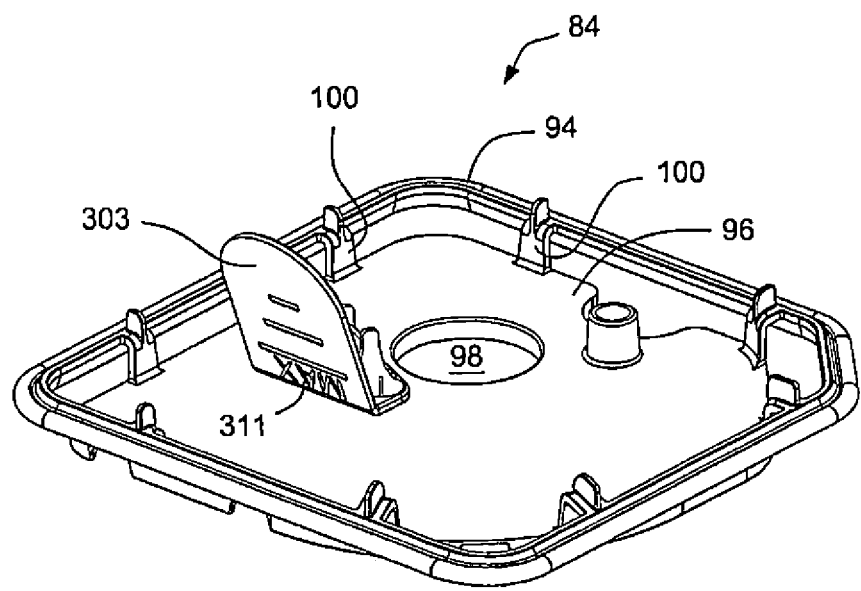
FIG. 57 schematically depicts another perspective view of the flow plate of FIG. 56.
Figure 58:
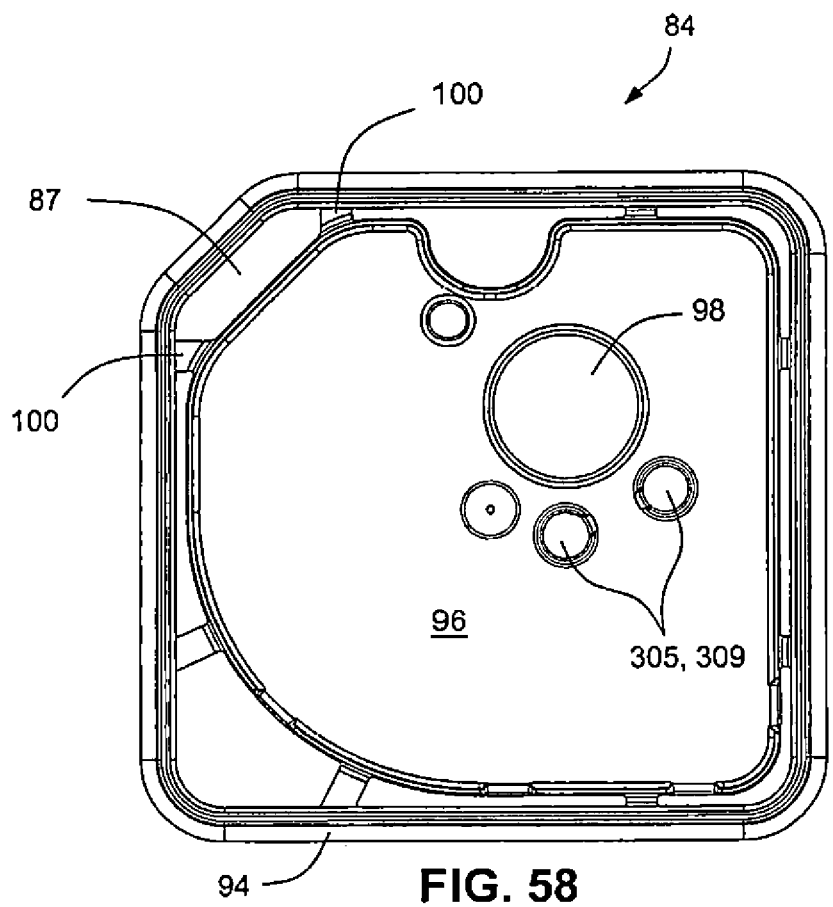
FIG. 58 schematically depicts a top view of the flow plate of FIGS. 56 and 57.

Referring to FIG. 49, the generally triangular portion of the water level indicator 102 extends below the frame seal 94 into the tub base 82 when the tub is in the assembled condition and includes a first angled wall 109 and a second angled wall 111. As the water level of the tub base 82 increases during fill up, the water level will initially contact the bottom of the water level indicator 102. As the water level continues to increase, the second angled wall 111 directs the water level toward the drain hole 104 and the indicia 103 which are provided in the angled wall 111 between the frame seal 94 and the dividing plate 96 of the flow plate. As the water level continues to increase and approaches the drain hole 104, the visibility of the water level relative to the indicia 103 increases. As the indicia 103 is provided at the same level as the drain hole 104, the maximum fill level of the tub 20 is detected when the water level reaches the level of the drain hole 104 and the indicia 103.

Figure 48:
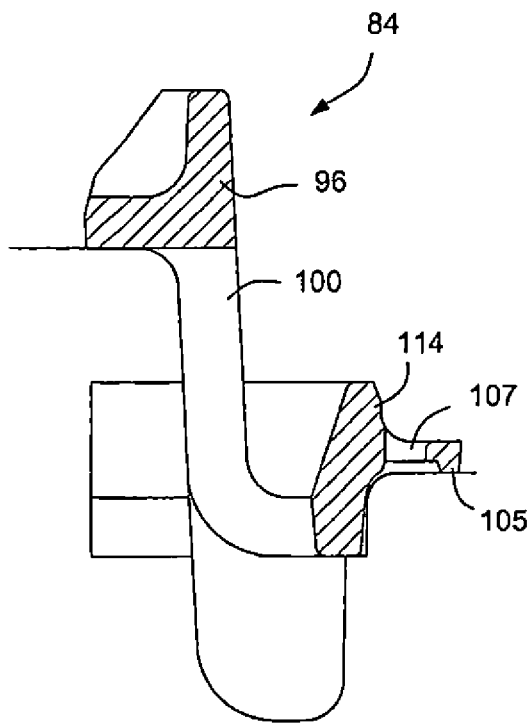
FIG. 48 schematically depicts a detailed view of a wedge of the bridge of the flow plate.

Referring to FIGS. 33, 35, 42 and 48, the seal 112 may be provided on the periphery of the wedge 114 of the bridge 100. The wedge 116 of the tub lid 86 is configured to engage the wedge 114 of the dividing plate 96 of the flow plate 84 to force the seal 112 between the rim 118 of the tub base 82 and the latch 130 of the tub lid 86. As shown in FIG. 48, the wedge 114 may comprise a flange 105 around its perimeter that includes a slot 107 that is configured to receive a portion of the seal 112, as shown, for example, in FIG. 33.

Humidifier Tub-Disposable-Third Embodiment

Referring to FIGS. 50-62, a humidifier water tub 20 is configured to be disposable according to still another sample embodiment as illustrated. The humidifier tub 20 comprises a tub base 82 and a tub lid 86. The tub lid 86 includes an oval opening 300 and a sump region 340 that surrounds the outlet 92 of the channel 90 that is formed in the tub lid 86 to direct the flow of air from the flow generator to the water contained in the tub 20. The sump region 340 facilitates filling the tub 20 by providing a larger area for entry of water than the outlet 92 of the flow channel 90.

The tub lid 86 also comprises a cover portion 301 that covers the section of the flow channel 90 from the flow generator 12 to the inlet 98 of the tub 20 that is angled down towards the flow generator 12. The cover portion 301 prevents any water from flowing back into the flow generator 12 if the tub 20 was filled with water while still connected to the flow generator 12 as water may only be poured into the tub in the region provided by the opening 300 which is designed to channel the water down towards the outlet 92.

As shown in FIGS. 53-62, a water level indicator 320 may be provided to the humidifier tub 20 that is visible through the window 30 of the lid 18. The water level indicator 320 may comprise a base portion 307 and an angled portion 303 extending from the base portion 307. The angled portion 303 may include markings 304 to indicate various water levels. The angled portion 303 may also include indicia 311 to indicate a maximum water fill level.

Figure 59:
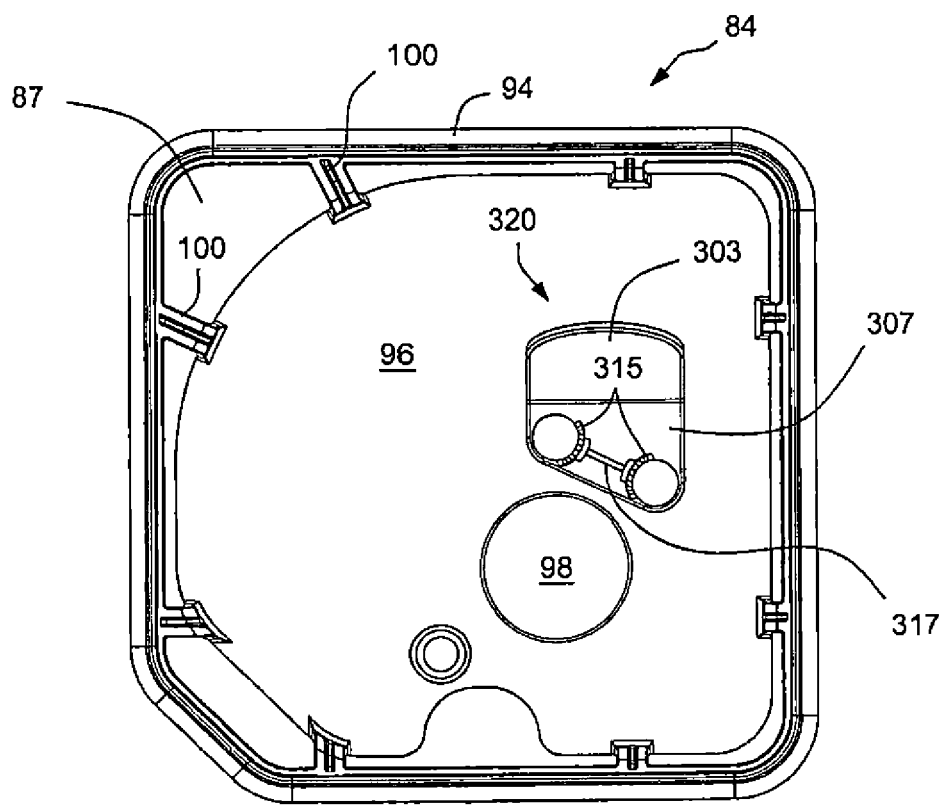
FIG. 59 schematically depicts a bottom view of the flow plate of FIGS. 56-58.
Figure 60A:
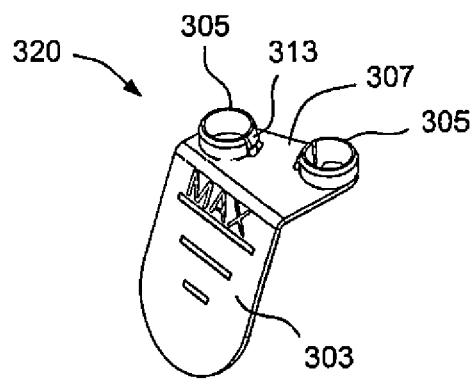
FIGS. 60a-60c schematically depict a water level indicator usable with the flow plate of FIGS. 56-59.
Figure 60B:
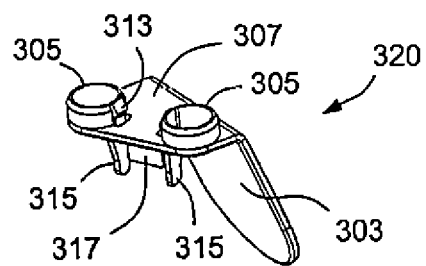
Figure 60C:
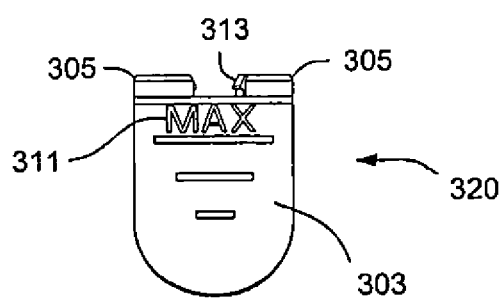
Figure 61:
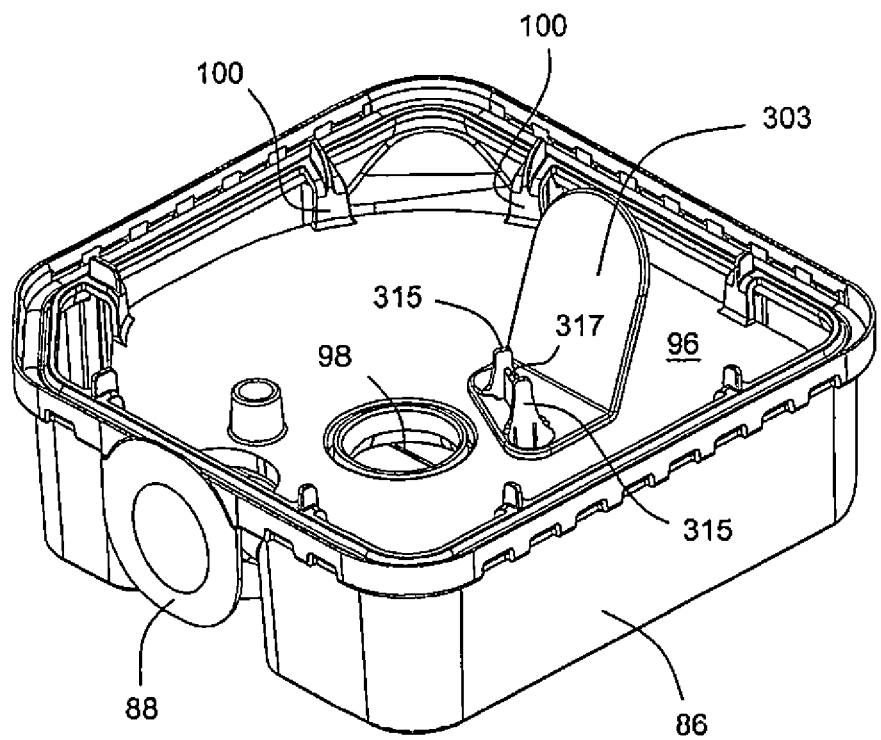
FIG. 61 schematically depicts a perspective view of the flow plate and water level indicator of FIGS. 56-60c with the tub lid of the tub of FIGS. 50-55.
Figure 62:
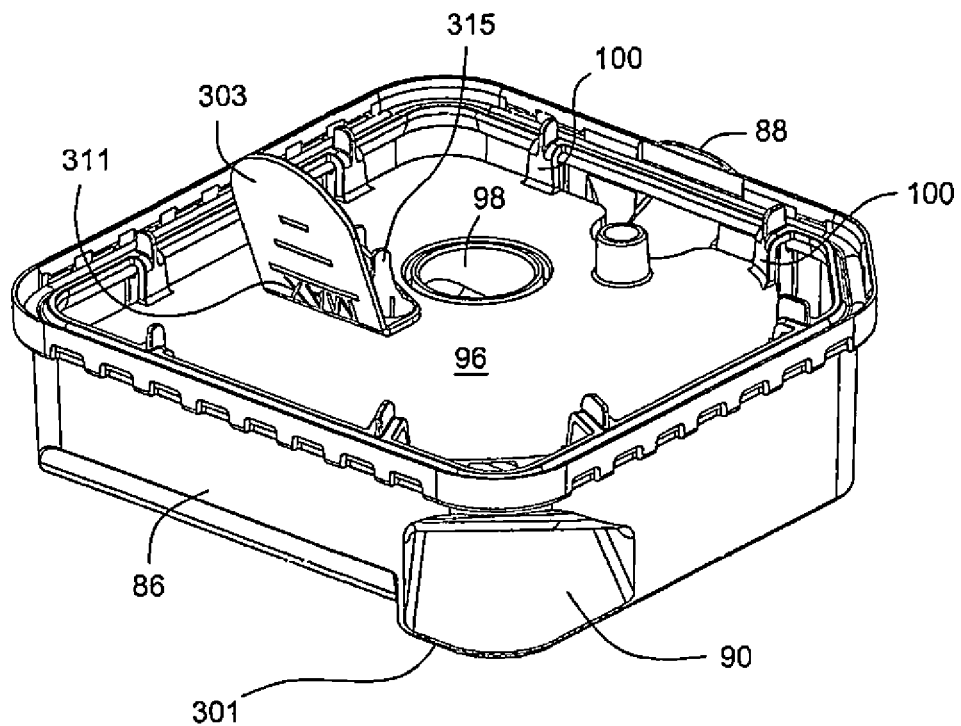
FIG. 62 schematically depicts another perspective view of the flow plate, water level indicator and tub lid of FIG. 61.

The water level indicator 320 may be removably connected to the dividing plate 96 of the flow plate 84 by posts 305. The posts 305 may be inserted into apertures 309 in the dividing plate 96 of the flow plate 84. As shown in FIGS. 60a-60c, the posts 305 may include latches 313 that are resiliently moveable with respect to the remaining portions of the posts 305. The latches 313 may be provided at the ends of leg portions 315 which are attached to the base 307 of the water level indicator 320. The leg portions 315 may be connected by a cross member 317, as shown in FIGS. 59, 60b and 61.

The water level indicator 320, for example, the angled portion 303, may be formed of a colored plastic material, for example yellow. The water level indicator 320 may be, for example, translucent. When the tub 20 is filled with water, the water level indicator 320 may appear to change color, for example appearing slightly darker or a greenish-yellowish color as the water level rises.

As shown in the figures, the water level indicator 320 may be a rounded D-shape, although it should be appreciated that other shapes may be used. It should also be appreciated that the water level indicator 320 may be attached to the dividing plate 96 of the flow plate 84 by structures other than the post 305 as shown and described in the drawings. For example, the water level indicator 320 may be adhered to the dividing plate 96, or the water level indicator 320 may be integrally formed, for example molded, with the dividing plate 96 of the flow plate 84.

Humidifier Tub-Reusable and Cleanable-First Embodiment

Figure 63:
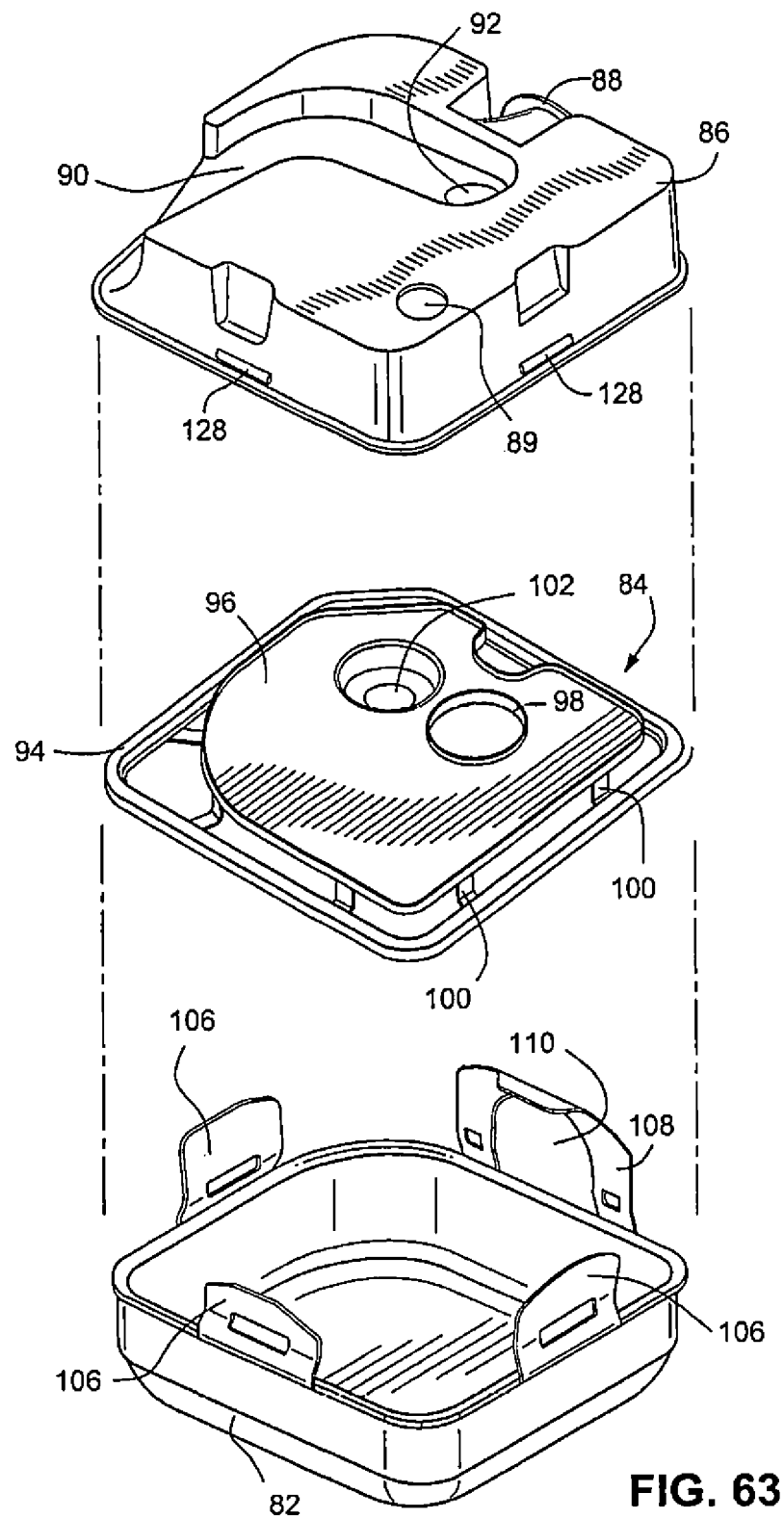
FIG. 63 schematically depicts an exploded assembly of a tub, including the tub base and flow plate of FIG. 19, according to another sample embodiment.
Figure 64:
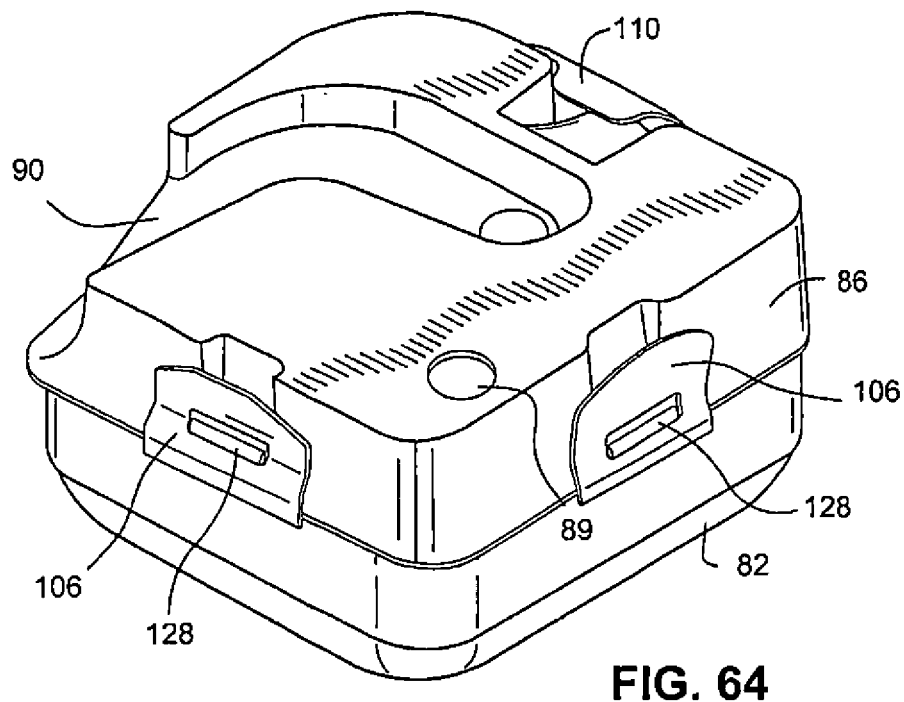
FIG. 64 schematically depicts the assembled tub of FIG. 63.

Referring to FIGS. 63-67, a tub 20 according to another embodiment of the invention is configured to be reusable, and cleanable. The tub base 82 comprises a plurality of clips 106 that are configured to engage and retain the tub lid 86 in connection with the tub base 82. A clip 108 is also provided and comprises an aperture 110 to accommodate the outlet 88 of the flow plate, as shown in FIG. 63.

Figure 65:
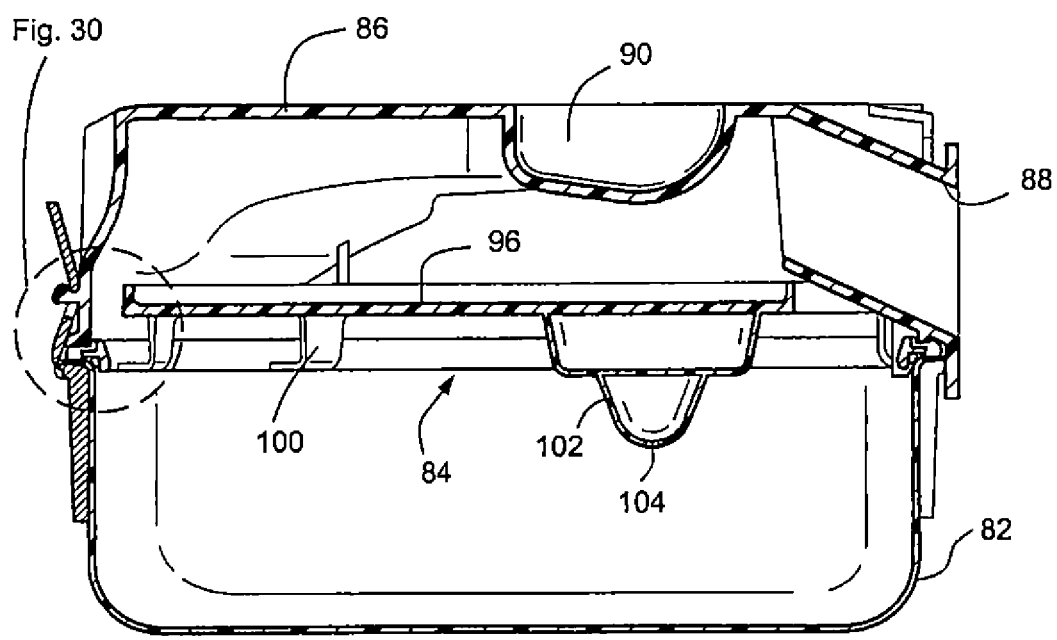
FIG. 65 schematically depicts a cross section of the tub of FIG. 64.
Figure 66:
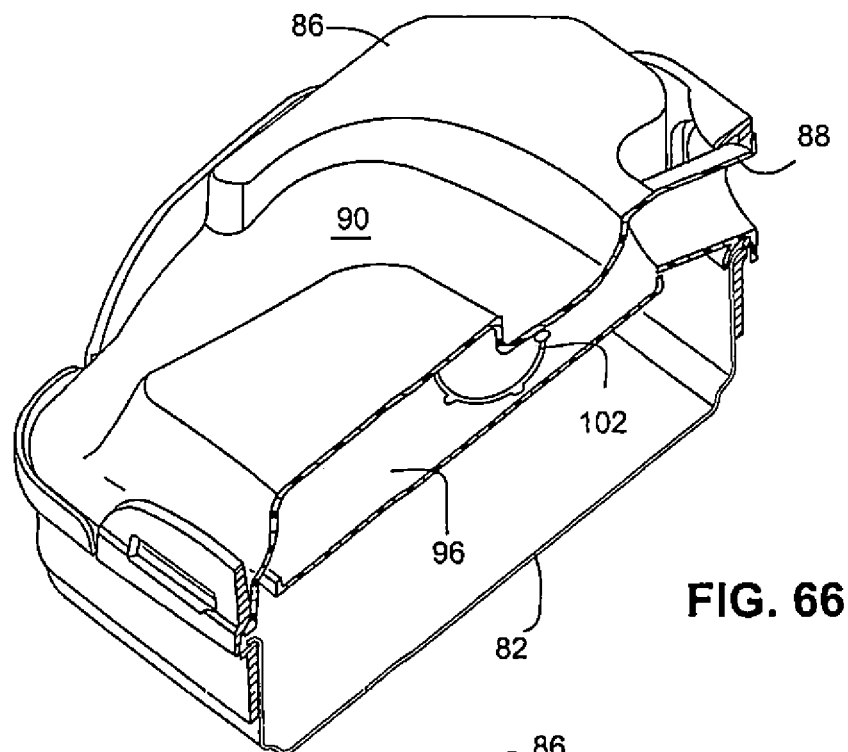
FIG. 66 schematically depicts a section view of the tub of FIG. 64.
Figure 67:
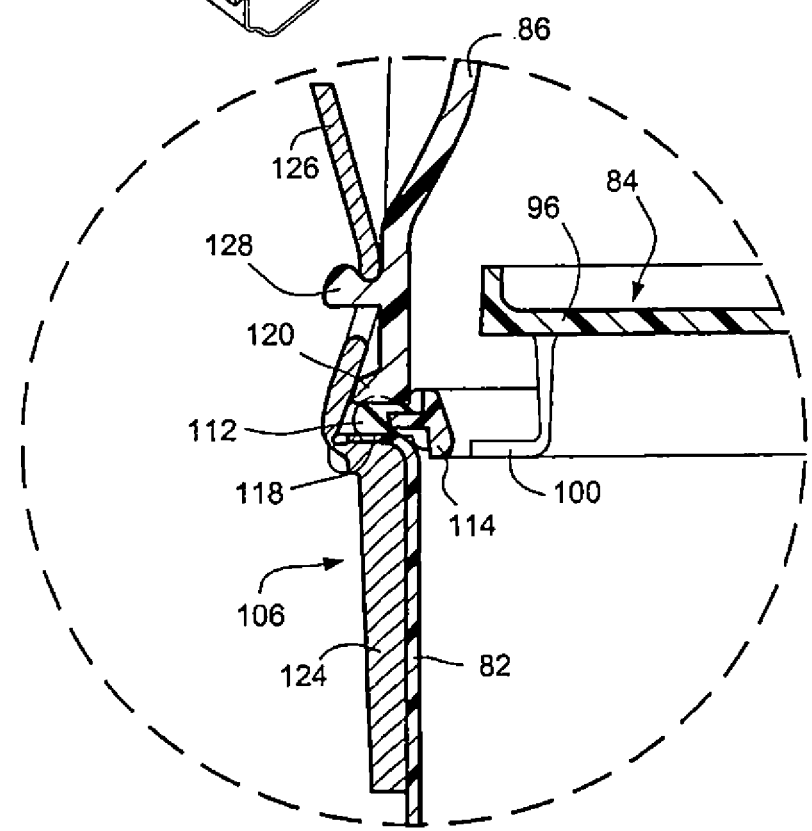
FIG. 67 schematically depicts a seal between the flow plate and the tub base of the tub of FIG. 63.
Figure 68:
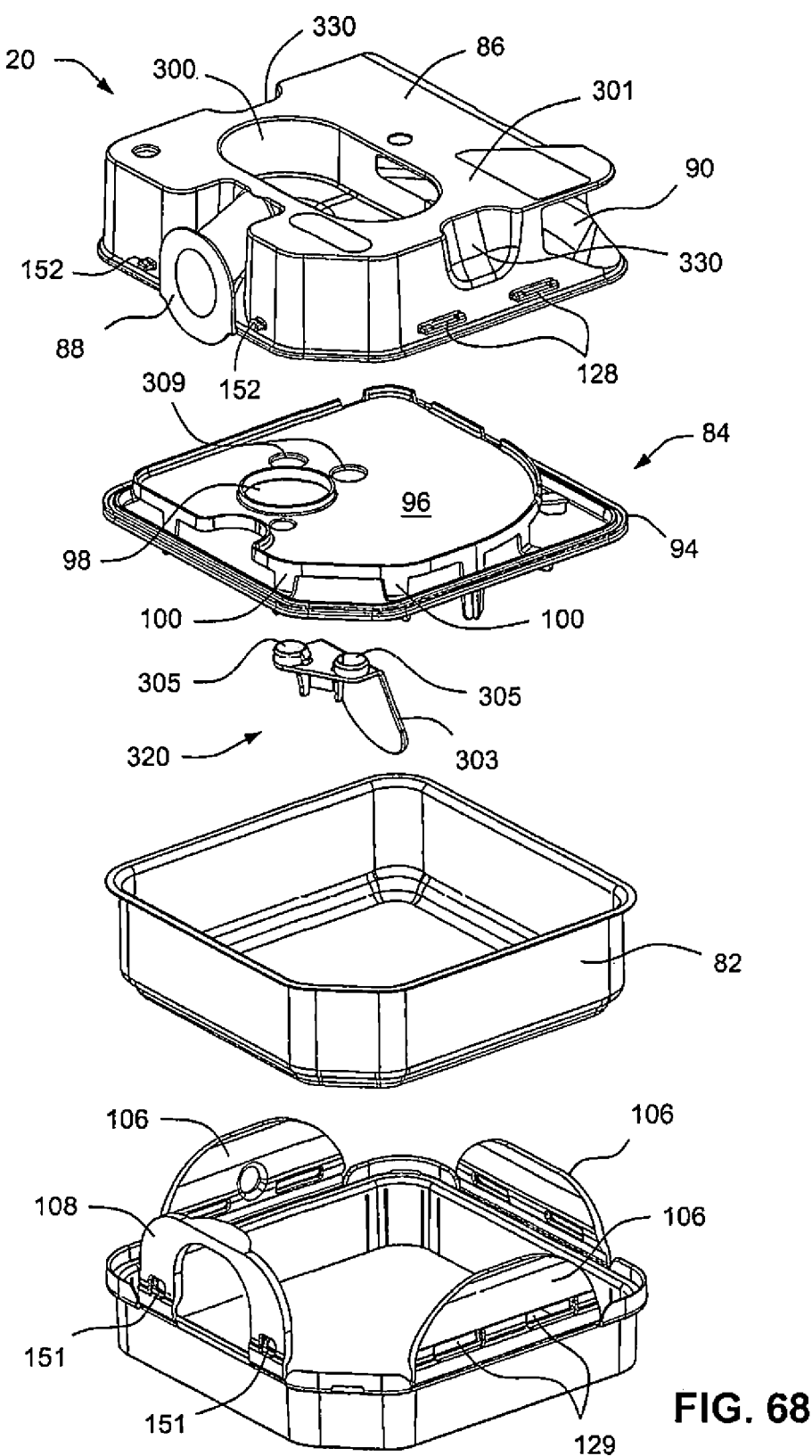
FIG. 68 schematically depicts an exploded assembly of a tub according to another sample embodiment.
Figure 69:
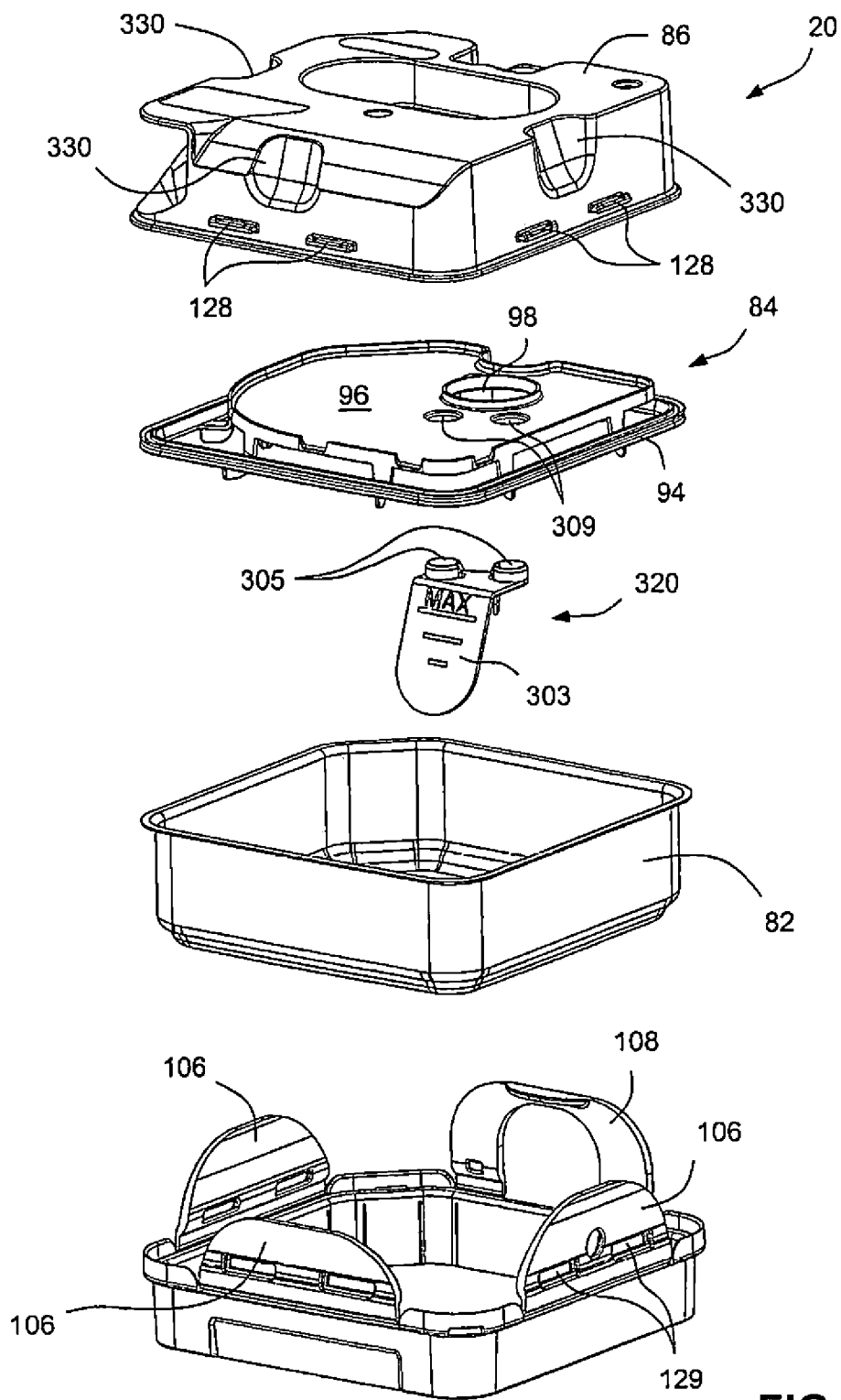
FIGS. 69 schematically depicts an exploded assembly of the tub of FIG. 68 from another perspective.
Figure 70:
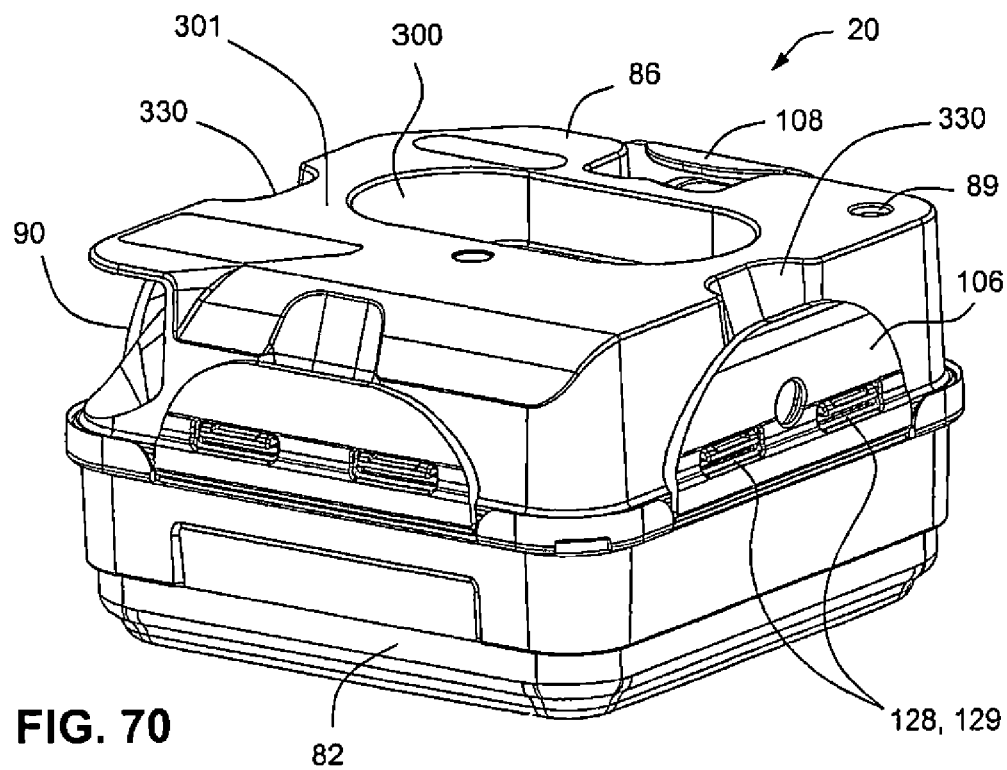
FIG. 70 schematically depicts a perspective view of the tub of FIGS. 68 and 69.
Figure 71:
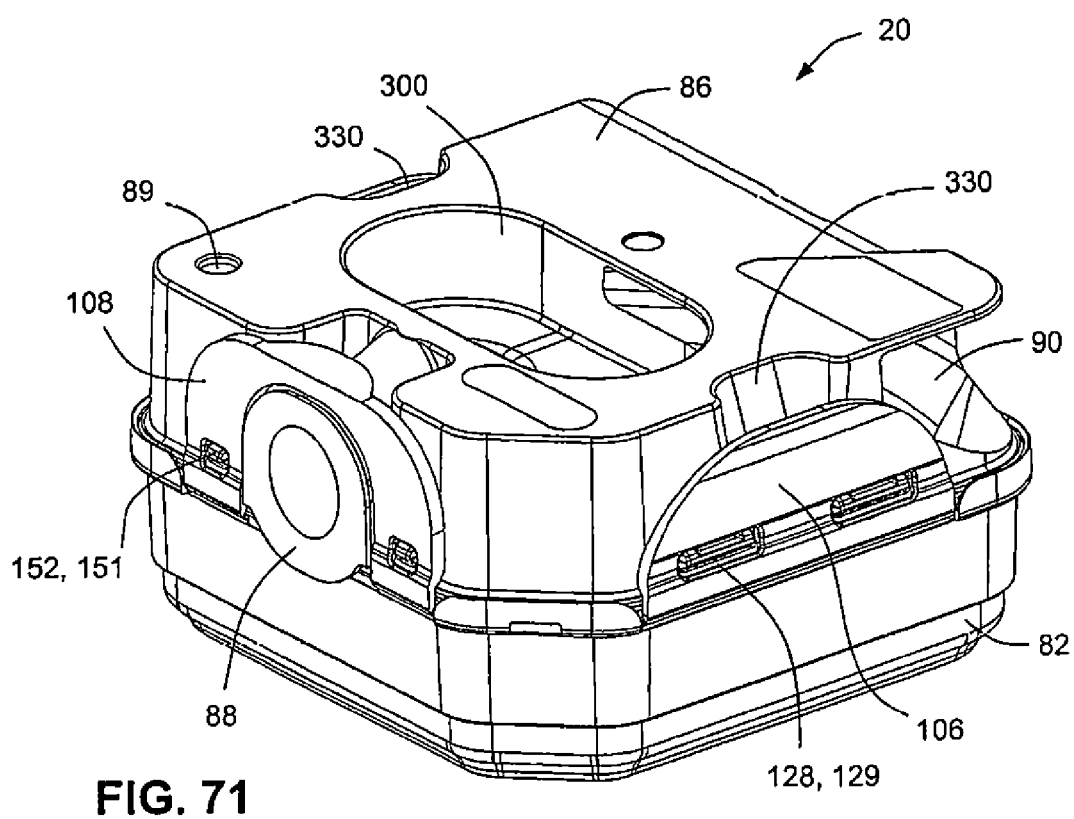
FIG. 71 schematically depicts another perspective view of the tub of FIGS. 68 and 69.
Figure 72:
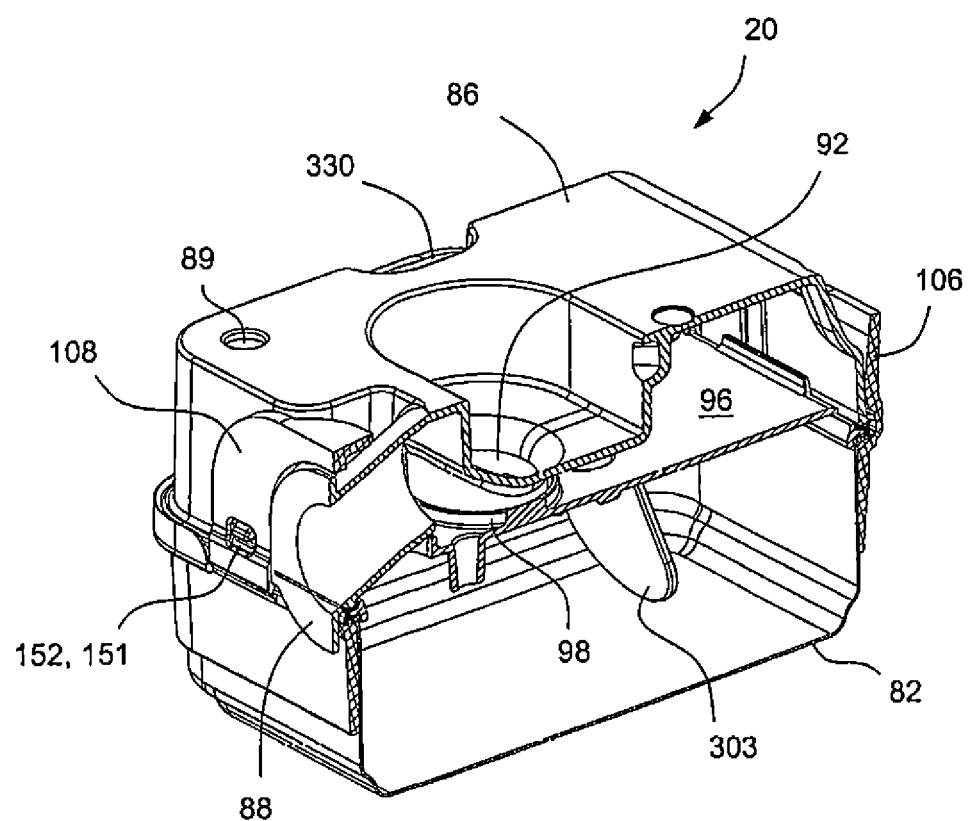
FIG. 72 schematically depicts a section of the tub of FIGS. 68-71.

The flow plate 84 is configured to be removable from the tub base 82 and it is not permanently secured to the tub base 82. As shown in FIGS. 65 and 67, the bridges 100 of the flow plate 84 include a wedge 114 that is connected to a seal 112. The seal 112 is forced into sealing engagement between a rim 120 of the tub lid 86 and the rim 118 of the tub base 82. The clip 106 is provided to clip the tub lid 86 to the tub base 82 with the seal 112 secured in between in sealing engagement. A first portion 124 of the clip 106 engages the tub base 82 up to the rim 118 and a second portion 126 of the clip 106 is configured to engage a projection 128 of the tub lid 86 to secure the tub lid 86 and the tub base 82 in engagement.

The humidifier 14 does not include any seals that are provided under the water supply of the tub base 82. The lid 18 comprises the seal 19 to allow for pressurizing of the humidifier chamber 16 with the flow provided by the flow generator 12 to reduce the pressure on the tub joints, including the disposable tub and the reusable, cleanable tub, thus reducing leaks. Pressurizing the humidifier chamber also reduces tolerances for insertion of the water tub with respect to seals on the inlet of the humidifier and the outlet tube 70 of the humidifier 14. The sealing ring 76 provided to the outlet tube 70 is provided on an outer surface of the humidifier cradle 32 and not provided under the water of the supply contained in the tub base 82.

Humidifier Tub-Reusable and Cleanable-Second Embodiment

Referring to FIGS. 68-72, a water tub 20 according to another sample embodiment is configured to be reusable and cleanable. The tub 20 may have a water level indicator 320 similar to the water level indicator described with respect to the previous embodiments. It should be appreciated that the tub 20 may be provided with any of the water level indicators described herein.

The tub lid 86 may include the cover portion 301 to cover the inlet region of the flow channel 90 adjacent to the inlet 22 of the humidifier 14 that is connected to the flow generator 12.

As shown in FIGS. 68-72, the tub lid 86 may be secured to the tub base 82 by a plurality of clips 106, 108. The clip 108 may have an aperture configured to accommodate the outlet 88 of the tub 20. The tub lid 86 may include projections 128 that are received in apertures 129 in the clips 106. The tub lid 86 may also include projections 152 that are received in apertures 151 provided in the clip 108.

As also shown in FIGS. 68-72, the tub lid 86 may include recesses 330 to accommodate the fingers of a user of the tub 20 to provide a space between the tub lid 86 and the clips 106 as the user inserts the tub lid 86 on to the tub base 82 so that the projections 128 are received in the apertures 129. The recesses 330 may also accommodate the fingers during removal of the lid 86 from the base 82, for example to allow the parts of the tub 20 to be disassembled and cleaned.

It should be appreciated that the reusable and cleanable tubs may include a water level indicator as discussed above with respect to the embodiments of the disposable tub. It should also be appreciated that the reusable and cleanable tubs may include more than one water level indicator as discussed above with respect to the embodiments discussed above. It should further be appreciated that the water level indicator, or indicators, or the tub may not include indicia to include a maximum water level.

Heated Tube

Figure 73:
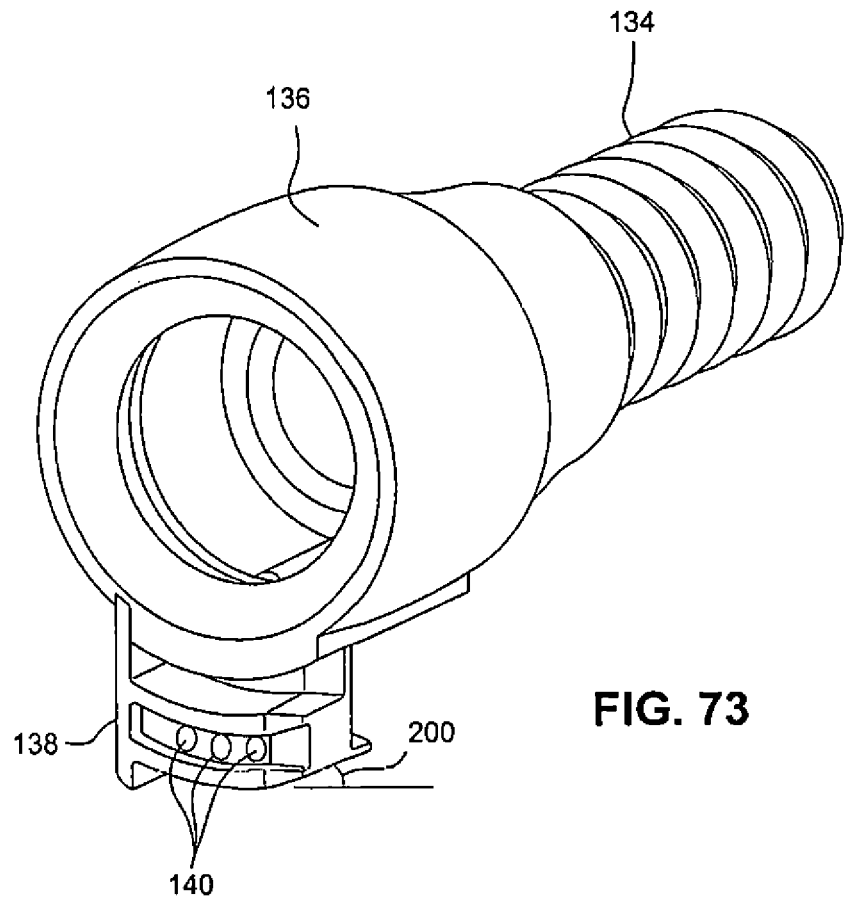
FIG. 73 schematically depicts a heated air delivery hose, tube, or conduit, including a cuff having a humidifier connector.

Referring to FIG. 73, a heated tube 134 is connectable to the outlet tube 70 of the humidifier 14. The heated tube 134 comprises a cuff 136 that includes a humidifier connector 138 that is configured to be connected to the tube connector 50 of the humidifier 14. The humidifier connector 138 comprises terminals 140 that are configured to receive the contacts 78 of the tube connector 50 when the humidifier connector 138 and the tube connector 50 are connected. The cuff 136 may be formed as described, for example, in U.S. application Ser. No. 11/936,822, the entire contents of which are incorporated herein by reference. The heated tube may include, for example, two or three wires and may transmit and receive signals to and from a controller in the humidifier and/or the flow generator as described in U.S. application Ser. No. 11/936,822. The end of the humidifier connector 138 that is configured for insertion into the tube connector 50 of FIG. 15 may include an angle 200 to facilitate insertion of the connector 138 into the tube connector 50. The angle 200 may be between about 15°-35°.

Figure 74:
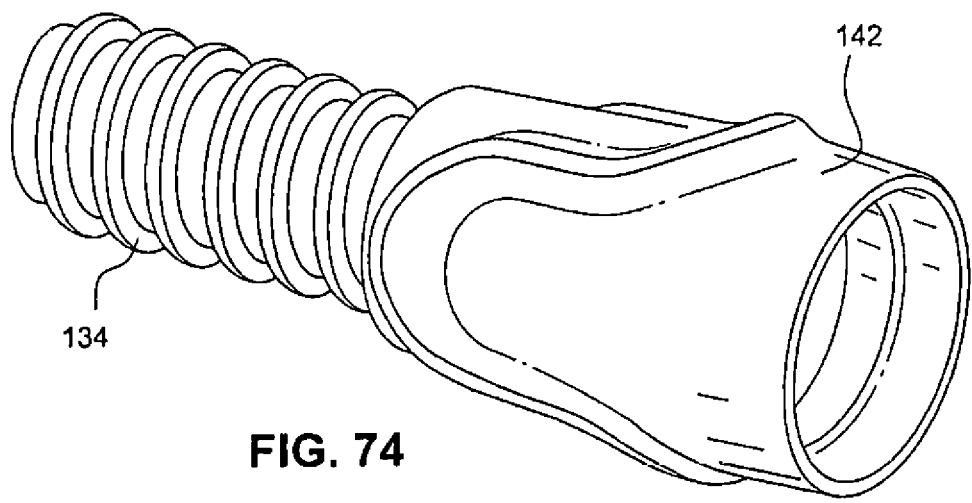
FIGS. 74 and 75 schematically depict the air delivery hose, tube, or conduit of FIG. 73 including a cuff to connect the hose, tube, or conduit to a patient interface, such as a mask.
Figure 75:
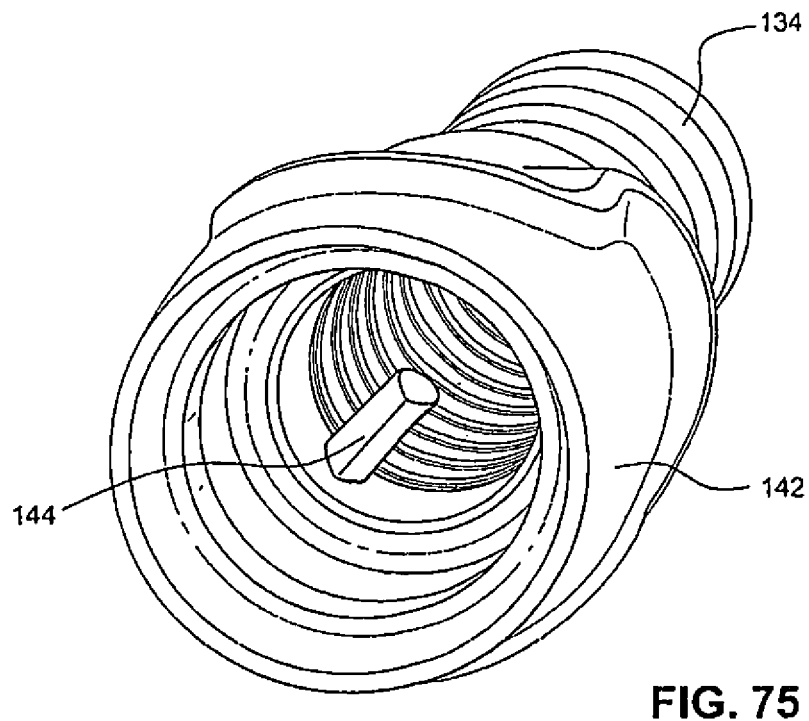
Figure 76:
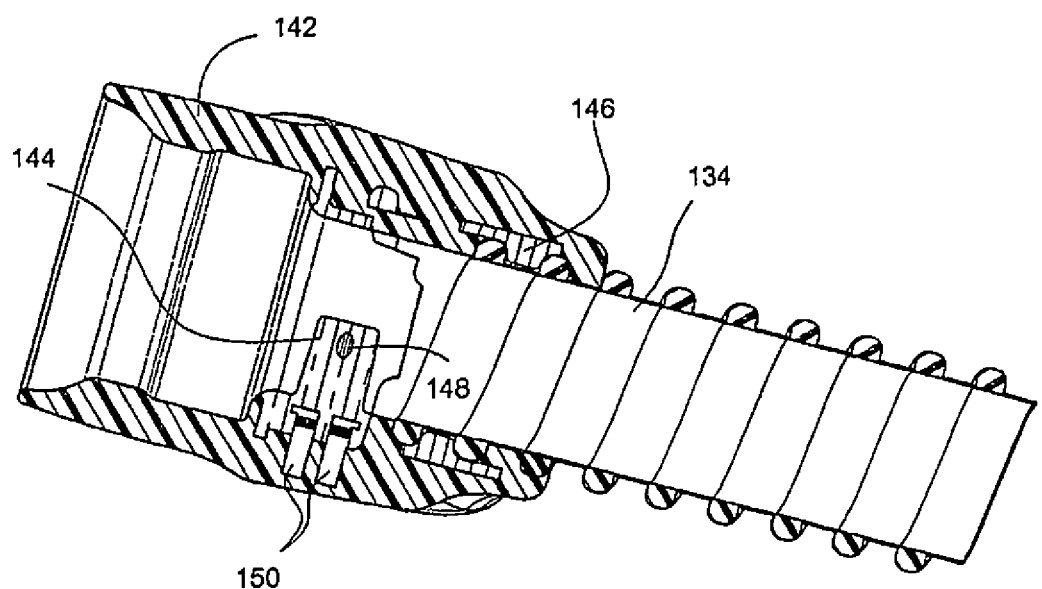
FIG. 76 schematically depicts a cross section of the hose, tube, or conduit and cuff of the FIGS. 56 and 57.

Referring to FIGS. 74-76, the heated tube 134 may be connected to a patient interface, e.g. a mask, by a cuff 142 provided at the end of the heated tube 134. An aerofoil fixture 144 is provided in the cuff 142 and includes a thermistor 148, as shown in FIG. 75. The shape of the aerofoil fixture 144 provides a smooth flow around the aerofoil fixture 144 so that the thermistor 148 provides a good reading of the temperature of the flow of breathable gas in the tube 134. The cuff 142 may be formed by, for example, overmolding on a pre-block 146, or any method disclosed, for example, in U.S. application Ser. No. 11/936,822. The thermistor 148 is connected to the wires in the heated tube 134 by lead frames 150. The temperature sensed by the thermistor 148 may be provided as a signal from the thermistor 148 through the lead frames 150 and the wires to a controller located in the humidifier and/or the flow generator.

The tube 134 may have a 15 mm internal diameter. The tube 134 may be heated using wires as described in U.S. application Ser. No. 11/936,822. A non-heated 15 mm air delivery tube my also be used. The 15 mm internal diameter tube may be connected to the tube connector 50 and the patient interface using a 22 mm isotaper connection.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features.

In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

It will further be understood that any reference herein to known prior art does not, unless the contrary indication appears, constitute an admission that such prior art is commonly known by those skilled in the art to which the invention relates.

What is claimed is:

1. A respiratory apparatus for providing a humidified flow of pressurised breathable gas to a patient, comprising:
    a flow generator to generate a flow of pressurised breathable gas to be delivered to a patient;
    a pressurisable humidifier chamber including a chamber inlet configured to receive the flow of pressurised breathable gas from the flow generator, the chamber having a rear wall comprising a chamber outlet, the chamber having a bottom support surface including a heating plate having a substantially upward-facing heating surface;
    a humidifier lid being hingedly attached to a wall of the chamber and pivotably movable between an open position and a closed position, an inside surface of the humidifier lid having a depending rib;
    a water tub configured to contain a supply of water, the tub having a tub base with a bottom adapted to contact the heating surface, a tub lid, and a tub seal sealing between the tub base and the tub lid and located above the supply of water, the tub lid having a tub inlet and a tub outlet, the tub outlet being provided on a rear wall of the tub and configured to deliver the flow of pressurised breathable gas with added humidity to the chamber outlet, the tub being constructed and dimensioned to be wholly positionable within the chamber;
    a chamber seal configured to seal the chamber such that the flow of pressurised breathable gas pressurises the chamber when the tub is wholly within the chamber and the humidifier lid is in the closed position, the chamber seal having a groove configured to receive the depending rib of the humidifier lid, the chamber seal having a sealing rim that extends around a perimeter of the chamber seal, the sealing rim having a perimeter that is larger than a perimeter of the tub lid so as to be positioned above and seal downwardly against a substantially upward-facing surface of the chamber when the humidifier lid is in the closed position; and
    a clip to force the tub seal into sealing engagement and to secure the tub lid and the tub base to one another.

2. The respiratory apparatus according to claim 1, further comprising an outlet seal to seal between the chamber outlet and the tub outlet.

3. The respiratory apparatus according to claim 2, wherein the outlet seal includes a lip that projects into the chamber, the lip being mounted on a flange that is seated in a recess provided in an inner surface of the rear wall.

4. The respiratory apparatus according to claim 1, further comprising mutually engaging surfaces of the chamber and the tub configured to urge the tub in a rearward horizontal direction towards the chamber outlet to facilitate sealing between the tub outlet and the chamber outlet.

5. The respiratory apparatus according to claim 1, wherein the sealing rim has a profile as seen in cross section that curves downward and inwardly towards the chamber, such that the sealing rim is structured to be exposed to the flow of pressurised breathable gas provided to the chamber.

6. The respiratory apparatus according to claim 1, wherein the tub inlet is spaced away from the chamber inlet by a distance when the tub is received in the chamber.

7. The respiratory apparatus according to claim 1, wherein the depending rib is spaced inwardly from an outermost border of the humidifier lid, at least a portion of the chamber seal being positioned substantially between the depending rib and the outermost border when the humidifier lid is in the closed position.

8. The respiratory apparatus according to claim 1, further comprising laterally spaced recesses formed in the tub lid to accommodate the fingers of a user for handling the tub.

9. The respiratory apparatus according to claim 1, wherein the chamber seal is selectively engageable with the tub lid.

10. The respiratory apparatus according to claim 1, wherein, when the humidifier lid is in the closed position with the tub in the chamber, the humidifier lid pushes the tub against the heating plate.

11. The respiratory apparatus according to claim 1, wherein the chamber seal comprises at least one first protrusion configured to engage the tub, wherein the at least one first protrusion is wedge-shaped.

12. The respiratory apparatus according to claim 11, wherein the chamber seal comprises at least one second protrusion configured to push against the tub lid when the humidifier lid is in the closed position.

13. The respiratory apparatus according to claim 1, wherein the tub has a substantially polygonal shape having four corners, three of which corners are similarly rounded corners and the fourth corner has a different shape compared to the three similarly rounded corners.

14. The respiratory apparatus according to claim 1, further comprising a user-operated lid closure member to maintain the humidifier lid in the closed position, the user-operated lid closure member comprising:
    at least one latch to selectively engage with a catch;
    a spring to bias the latch into engagement with the catch;
    a post to support the spring; and
    an opening member configured to be pushed against the bias of the spring to release the latch from the catch, thus allowing the humidifier lid to be pivoted to the open position.

15. The respiratory apparatus according to claim 1, further comprising a water level indicator to indicate a maximum fill level for the water tub, the water level indicator being suspended within the tub for direct exposure to water within the tub, the water level indicator having an angled wall having a first portion extending into the tub to a first depth and a second portion extending into the tub to a second depth that is different than the first depth, wherein as the water level of the tub base increases when filling the tub, the water level will initially contact the first portion of the angled wall of the water level indicator, and as the water level continues to increase, the water will then rise upwardly towards the second portion of the angled wall to contact indicia indicating the maximum fill level, the indicia on the angled wall being positioned so as to be visible when the water tub is viewed from above.

16. The respiratory apparatus according to claim 1, wherein the rear wall comprises an outlet tube, and the respiratory apparatus further comprises a gas delivery tube with a first end connectable to the outlet tube to receive the flow of breathable gas, and a second end including a cuff configured for connection to a patient interface.

17. The respiratory apparatus according to claim 1, wherein the tub lid has a water aperture, and the chamber seal further comprises an aperture seal projecting from an underside of the chamber seal to seal the water aperture.

18. The respiratory apparatus according to claim 1, wherein the tub is removable from the humidifier chamber and is configured to prevent water from flowing back into the flow generator.

19. The respiratory apparatus according to claim 1, wherein the clip is located along a lateral side of the tub.

20. The respiratory apparatus according to claim 19, wherein the clip is mounted for pivotable movement between an open position and a closed position, the clip being pivotable about an axis located at a proximal end of the clip, the clip having a slot configured to receive a projection of the tub when the clip is pivoted from the open position to the closed position, the slot and the projection extending parallel to the axis, and the slot being positioned closer to the proximal end of the clip as compared to a distal end of the clip.

21. The respiratory apparatus according to claim 1, wherein:
the respiratory apparatus further comprises an outlet seal to seal between the chamber outlet and the tub outlet,
the outlet seal includes a lip that projects into the chamber, the lip being mounted on a flange that is seated in a recess provided in an inner surface of the rear wall,
the sealing rim has a profile as seen in cross section that curves downward and inwardly towards the chamber, such that the sealing rim is structured to be exposed to the flow of pressurised breathable gas provided to the humidifier chamber,
the tub inlet is spaced away from the chamber inlet by a distance when the tub is received in the chamber,
the depending rib is spaced inwardly from an outermost border of the humidifier lid, at least a portion of the chamber seal being positioned substantially between the depending rib and the outermost border when the humidifier lid is in the closed position,
the respiratory apparatus further comprises laterally spaced recesses formed in the tub lid to accommodate the fingers of a user for handling the tub,
the chamber seal is selectively engageable with the tub lid,
when the humidifier lid is in the closed position with the tub in the chamber, the humidifier lid pushes the tub against the heating plate, wherein: the chamber seal comprises at least one first protrusion configured to engage the tub, wherein the at least one first protrusion is wedge-shaped, the chamber seal comprises at least one second protrusion configured to push against the tub lid when the humidifier lid is in the closed position,
the tub has a substantially polygonal shape having four corners, three of which corners are similarly rounded corners and the fourth corner has a different shape compared to the three similarly rounded corners,
further comprising a user-operated lid closure member to maintain the humidifier lid in the closed position, the user-operated lid closure member comprising:
at least one latch to selectively engage with a catch;
a spring to bias the latch into engagement with the catch; and
a post to support the spring;
wherein the catch and the latch are configured to be released from one another by pushing against the bias of the spring, thus allowing the humidifier lid to be pivoted to the open position,
the respiratory apparatus further comprises a water level indicator to indicate a maximum fill level for the water tub, the water level indicator being suspended within the tub for direct exposure to water within the tub, the water level indicator having an angled wall having a first portion extending into the tub to a first depth and a second portion extending into the tub to a second depth that is different than the first depth, wherein as the water level of the tub base increases when filling the tub, the water level will initially contact the first portion of the angled wall of the water level indicator, and as the water level continues to increase, the water will then rise upwardly towards the second portion of the angled wall to contact indicia indicating the maximum fill level, the indicia on the angled wall being positioned so as to be visible when the water tub is viewed from above,
the rear wall comprises an outlet tube, and the respiratory apparatus further comprises a gas delivery tube with a first end connectable to the outlet tube to receive the flow of breathable gas, and a second end including a cuff configured for connection to a patient interface,
the tub lid has a water aperture, and the chamber seal further comprises an aperture seal projecting from an underside of the chamber seal to seal the water aperture,
the tub is removable from the humidifier chamber and is configured to prevent water flowing out of the tub from flowing back into the flow generator,
the clip is located along a lateral side of the tub, and
the clip is mounted for pivotable movement between an open position and a closed position, the clip being pivotable about an axis located at a proximal end of the clip, the clip having a slot configured to receive a projection of the tub when the clip is pivoted from the open position to the closed position, the slot and the projection extending parallel to the axis, and the slot being positioned closer to the proximal end of the clip as compared to a distal end of the clip.

22. The respiratory apparatus according to claim 1, wherein:
the respiratory apparatus further comprises an outlet seal to seal between the chamber outlet and the tub outlet,
the outlet seal includes a lip that projects into the chamber, the lip being mounted on a flange that is seated in a recess provided in an inner surface of the rear wall,
the depending rib is spaced inwardly from an outermost border of the humidifier lid, at least a portion of the chamber seal being positioned substantially between the depending rib and the outermost border when the humidifier lid is in the closed position,
the respiratory apparatus further comprises laterally spaced recesses formed in the tub lid to accommodate the fingers of a user for handling the tub,
when the humidifier lid is in the closed position with the tub in the chamber, the humidifier lid pushes the tub against the heating plate, wherein: the chamber seal comprises at least one first protrusion configured to engage the tub, wherein the at least one first protrusion is wedge-shaped, and the chamber seal comprises at least one second protrusion configured to push against the tub lid when the humidifier lid is in the closed position, the tub has a substantially polygonal shape having four corners, three of which corners are similarly rounded corners and the fourth corner has a different shape compared to the three similarly rounded corners, the respiratory apparatus further comprises a latch and catch to maintain the humidifier lid in the closed position, the respiratory apparatus further comprises a water level indicator to indicate a maximum fill level for the water tub, the water level indicator being suspended within the tub for direct exposure to water within the tub, the water level indicator having an angled wall having a first portion extending into the tub to a first depth and a second portion extending into the tub to a second depth that is different than the first depth, wherein as the water level of the tub base increases when filling the tub, the water level will initially contact the first portion of the angled wall of the water level indicator, and as the water level continues to increase, the water will then rise upwardly towards the second portion of the angled wall to contact indicia indicating the maximum fill level, the indicia on the angled wall being positioned so as to be visible when the water tub is viewed from above, the rear wall comprises an outlet tube, and the respiratory apparatus further comprises a gas delivery tube with a first end connectable to the outlet tube to receive the flow of breathable gas, and a second end including a cuff configured for connection to a patient interface, and the clip is mounted for pivotable movement between an open position and a closed position, the clip being pivotable about an axis located at a proximal end of the clip, the clip having a slot configured to receive a projection of the tub when the clip is pivoted from the open position to the closed position, the slot and the projection extending parallel to the axis, and the slot being positioned closer to the proximal end of the clip as compared to a distal end of the clip.

23. The respiratory apparatus according to claim 1, wherein:

the respiratory apparatus further comprises an outlet seal to seal between the chamber outlet and the tub outlet, the outlet seal includes a lip that projects into the chamber, the lip being mounted on a flange that is seated in a recess provided in an inner surface of the rear wall, the depending rib is spaced inwardly from an outermost border of the humidifier lid, at least a portion of the chamber seal being positioned substantially between the depending rib and the outermost border when the humidifier lid is in the closed position, the respiratory apparatus further comprises laterally spaced recesses formed in the tub lid to accommodate the fingers of a user for handling the tub, when the humidifier lid is in the closed position with the tub in the chamber, the humidifier lid pushes the tub against the heating plate, the respiratory apparatus further comprises a user-operated lid closure member to maintain the humidifier lid in the closed position, the user-operated lid closure member comprising at least one latch to selectively engage with a catch;

a spring to bias the latch into engagement with the catch; and an opening member configured to be pushed against the bias of the spring to release the latch from the catch, thus allowing the humidifier lid to be pivoted to the open position, the respiratory apparatus further comprises a water level indicator to indicate a maximum fill level for the water tub, the water level indicator being suspended within the tub for direct exposure to water within the tub, the water level indicator having an angled wall having a first portion extending into the tub to a first depth and a second portion extending into the tub to a second depth that is different than the first depth, wherein as the water level of the tub base increases when filling the tub, the water level will initially contact the first portion of the angled wall of the water level indicator, and as the water level continues to increase, the water will then rise upwardly towards the second portion of the angled wall to contact indicia indicating the maximum fill level, the indicia on the angled wall being positioned so as to be visible when the water tub is viewed from above, the tub lid has a water aperture, and the chamber seal further comprises an aperture seal projecting from an underside of the chamber seal to seal the water aperture, and the clip is mounted for pivotable movement between an open position and a closed position, the clip being pivotable about an axis located at a proximal end of the clip, the clip having a slot configured to receive a projection of the tub when the clip is pivoted from the open position to the closed position, the slot and the projection extending parallel to the axis.

24. A respiratory apparatus for providing a humidified flow of pressurised breathable gas to a patient, comprising:

a flow generator to generate a flow of pressurised breathable gas to be delivered to a patient;

a pressurisable humidifier chamber including a chamber inlet configured to receive the flow of pressurised breathable gas from the flow generator, the chamber having a rear wall comprising a chamber outlet, the chamber having a bottom support surface including a heating plate having a substantially upward-facing heating surface;

a humidifier lid being hingedly attached to a wall of the chamber and pivotably movable between an open position and a closed position;

a water tub configured to contain a supply of water, the tub having a tub base with a bottom adapted to contact the heating surface, a tub lid, and a tub seal sealing between the tub base and the tub lid and located above the supply of water, the tub lid having a tub inlet and a tub outlet, the tub outlet being provided on a rear wall of the tub and configured to deliver the flow of pressurised breathable gas with added humidity to the chamber outlet, the tub being constructed and dimensioned to be wholly positionable within the chamber; and a seal including a central portion and an outer perimeter portion surrounding the central portion, wherein the outer perimeter portion has a chamber seal configured to seal the chamber such that the flow of breathable gas pressurises the chamber, wherein the central portion has 1) at least one first protrusion configured to engage the tub lid, wherein the at least one first protrusion is wedge-shaped, 2) at least one second protrusion configured to push against the tub lid when the humidifier lid is in the closed position, and 3) an aperture seal projecting from an underside of the seal to seal a water aperture of the tub lid.

25. The respiratory apparatus according to claim 24, further comprising a water level indicator to indicate a fill level for the water tub, the water level indicator being suspended within the tub for direct exposure to water within the tub, the water level indicator having an angled surface, wherein as the water level of the tub base increases when filling the tub, the water level will initially contact a bottom of the angled surface of the water level indicator, and as the water level continues to increase, the water will then contact indicia towards a top of the angled surface indicating the fill level.

26. The respiratory apparatus according to claim 24, further comprising a clip to secure the tub lid and the tub base to one another, the clip being located along a lateral side of the tub, the clip being mounted on the tub for pivotable movement about an axis located at a proximal end of the clip, the clip having a slot configured to receive a projection of the tub when the clip is pivoted to a secured position, the slot extending parallel to the axis and being positioned closer to the proximal end of the clip as compared to a distal end of the clip.

27. The respiratory apparatus according to claim 24, wherein:
the seal has a groove configured to receive an edge of the humidifier lid,
the chamber seal includes a sealing rim that extends about a perimeter of the seal, the sealing rim having a profile as seen in cross section that projects downwards from the humidifier lid and curves inwardly towards the chamber, the sealing rim extending beyond the edge of the tub lid along the entire perimeter of the tub lid, the sealing rim being adapted to engage an upwardly facing rim surrounding the chamber,
the tub lid includes a water opening and the seal includes a sealing ring to seal the water opening, the sealing ring projecting downwards from an underside of the seal, and
the tub lid has laterally spaced recesses to accommodate the fingers of a user for handling the tub.

28. A respiratory apparatus for providing a humidified flow of pressurized breathable gas to a patient, comprising:
a flow generator to generate a flow of pressurized breathable gas to be delivered to a patient;
a chamber configured to receive the flow of pressurized breathable gas, the chamber having a chamber inlet to deliver the pressurized breathable gas from the flow generator to the chamber, the chamber having a chamber outlet to deliver the flow of breathable gas to an outlet tube, the chamber having a bottom support surface having a heating plate;
a tube connector in fluid communication with the chamber outlet;
a tub configured to contain a supply of water, the tub being configured to be inserted into the chamber, the tub having a tub base, a tub lid and a tub seal between the tub lid and the tub base, the tub base having with a bottom adapted to contact the heating plate, the tub lid having a tub inlet and a tub outlet, the tub outlet being configured to deliver the humidified flow of breathable gas to the chamber outlet;
a latch engageable with a catch to maintain the tub within the chamber;
a user-operated opening member configured to be pushed to release the latch from the catch, thus allowing the tub to be removed from the chamber;
a clipping structure to force the tub seal into sealing engagement and to secure the tub lid and the tub base to one another, the clipping structure being located along a lateral side of the tub, the clipping structure including a clip mounted for movement towards and away from the lateral side of the tub, the clip having a pair of laterally spaced slots each configured to receive a projection of the tub when the clip is moved to a closed position, wherein the clipping structure is configured to force a rim of the tub lid into sealing engagement with a rim of the tub base; and
a water level indicator to indicate a maximum fill level for the water tub.

29. The respiratory apparatus according to claim 28, further comprising an outer rim, a circular inlet, and a plurality of bridges that connect the outer rim to the circular inlet, the tub seal being supported by the outer rim, the circular inlet being aligned with the tub inlet such that the flow of pressurized breathable gas is directed from the tub inlet to the circular inlet when the tub base, the tub lid and the tub seal are connected.

30. A respiratory apparatus for providing a humidified flow of pressurized breathable gas to a patient, comprising:
a flow generator to generate a flow of pressurized breathable gas to be delivered to a patient;
a pressurizable humidifier chamber including a chamber inlet configured to receive the flow of pressurized breathable gas from the flow generator, the chamber having a rear wall including an inner surface including a chamber outlet, the rear wall including an outlet tube protruding from an outer surface of the rear wall, the chamber having a bottom support surface including a heating plate;
a humidifier lid pivotable between an open position and a closed position, the humidifier lid having an outside surface and an inside surface, the inside surface having a depending rib, the humidifier lid comprising a hinge portion that is hingedly attached to a hinge portion provided on the rear wall of the chamber;
a water tub configured to contain water, the tub having a tub base with a bottom adapted to contact the heating plate, a tub lid, and a tub seal sealing between the tub base and the tub lid, the tub lid having a tub inlet and a tub outlet, the tub outlet being provided on a rear wall of the tub and configured to deliver the flow of pressurized breathable gas with added humidity to the chamber outlet, the tub lid having a water aperture;
a chamber seal between the humidifier lid and the tub lid when the tub is in the chamber and the humidifier lid is in the closed position, the chamber seal being configured to seal the chamber such that the flow of breathable gas pressurizes the chamber with the tub as a whole positioned therein, the chamber seal having a groove configured to receive the depending rib of the humidifier lid, the chamber seal having a sealing rim that extends around the perimeter of the chamber seal, the sealing rim positioned above and sealing downwardly against a substantially horizontal surface of the chamber when the humidifier lid is in the closed position, the chamber seal further comprising a circular sealing ring projecting from an underside of the chamber to seal the water aperture; and
a clipping structure to force the tub seal into sealing engagement and to secure the tub lid and the tub base to one another, the clipping structure being located along a lateral side of the tub, the clipping structure including a clip mounted for pivotable movement between an open position in which the tub lid may be lifted relative to the tub base and a closed position in which the tub lid is secured against relative movement relative to the tub base, the clip being pivotable about an axis located at a proximal end of the clip, the clip having a slot configured to receive a projection of the tub when the clip is pivoted from the open position to the closed position, the slot and the projection extending parallel to the axis, and the slot being positioned closer to the proximal end of the clip as compared to a distal end of the clip.

* * * * *